US012778939B2

(12) United States Patent
Harden et al.

(10) Patent No.: US 12,778,939 B2
(45) Date of Patent: Nov. 3, 2026

(54) IRAK4 INHIBITORS AND TOPICAL USES THEREOF

(71) Applicant: Dermira, Inc., Menlo Park, CA (US)

(72) Inventors: Jamie L. Harden, Menlo Park, CA (US); Delphine Imbert, Menlo Park, CA (US)

(73) Assignee: Dermira, Inc., Menlo Park, CA (US)

( * ) Notice: Subject to any disclaimer, the term of this patent is extended or adjusted under 35 U.S.C. 154(b) by 706 days.

(21) Appl. No.: 18/007,950

(22) PCT Filed: Jun. 29, 2021

(86) PCT No.: PCT/US2021/039646

§ 371 (c)(1),
(2) Date: Dec. 2, 2022

(87) PCT Pub. No.: WO2022/006129

PCT Pub. Date: Jan. 6, 2022

(65) Prior Publication Data

US 2023/0390265 A1 Dec. 7, 2023

Related U.S. Application Data

(60) Provisional application No. 63/046,531, filed on Jun. 30, 2020.

(51) Int. Cl.

| | |
|---|---|
| ***A61K 31/4439*** | (2006.01) |
| ***A61K 9/06*** | (2006.01) |
| ***A61K 47/06*** | (2006.01) |
| ***A61K 47/10*** | (2017.01) |
| ***A61K 47/12*** | (2006.01) |
| ***A61K 47/22*** | (2006.01) |
| ***A61K 47/32*** | (2006.01) |
| ***A61K 47/34*** | (2017.01) |
| ***A61P 17/00*** | (2006.01) |
| ***A61P 29/00*** | (2006.01) |

(52) U.S. Cl.

CPC ............ *A61K 31/4439* (2013.01); *A61K 9/06* (2013.01); *A61K 47/06* (2013.01); *A61K 47/10* (2013.01); *A61K 47/12* (2013.01); *A61K 47/22* (2013.01); *A61K 47/32* (2013.01); *A61K 47/34* (2013.01); *A61P 17/00* (2018.01); *A61P 29/00* (2018.01)

(58) Field of Classification Search

CPC ...... A61K 31/4439; A61K 9/06; A61K 47/06; A61K 47/10; A61K 47/12; A61K 47/22; A61K 47/32; A61K 47/34; A61K 9/0014; A61K 47/24; A61K 47/26; A61K 47/38; A61P 17/00; A61P 29/00; A61P 17/06; A61P 17/10; A61P 35/00; C07D 413/14

See application file for complete search history.

(56) References Cited

U.S. PATENT DOCUMENTS

| | | | | |
|---|---|---|---|---|
| 9,890,145 B2 | 2/2018 | Yoshida et al. | | |
| 2013/0072874 A1* | 3/2013 | Tokumoto | A61M 37/0015 | 604/173 |
| 2015/0133451 A1* | 5/2015 | Yoshida | A61P 37/08 | 514/369 |
| 2023/0125380 A1* | 4/2023 | Harden | A61P 29/00 | 514/341 |

FOREIGN PATENT DOCUMENTS

| | | |
|---|---|---|
| CN | 105899505 A | 8/2016 |
| CN | 116134038 A | 5/2023 |
| WO | WO 2018/095576 | 5/2018 |
| WO | WO 2018/129364 | 7/2018 |
| WO | WO 2019/143971 | 7/2019 |
| WO | WO 2019/191511 | 10/2019 |
| WO | WO 2019/246558 | 12/2019 |
| WO | WO 2020/028820 | 2/2020 |
| WO | WO 2021/092239 | 5/2021 |

OTHER PUBLICATIONS

Nola et al. The Use of Emollients as Sophisticated Therapy in Dermatology (Acta Dermatovenerol Croat. 2003, 11(2): 80-87). (Year: 2003).*

Dsouza et al. Polyethylene glycol (PEG): a versatile polymer for pharmaceutical applications (Expert Opinion on Drug Delivery, 13:9 , 1257-1275, 2016). (Year: 2016).*

Osborne et al. Skin Penetration and Permeation Properties of Transuctol-Neat or Diluted Mixtures (AAPS PharmSciTech, vol. 19, No. 8, 2018, 3512-3533). (Year: 2018).*

Medicherla et al., (2010) "Topical Alpha-Selective p38 MAP Kinase Inhibition Reduces Acute Skin 1-3 Inflammation 1 in Guinea Pig", Journal of Inflammation Research. 3, pp. 9-16.

Jeon et al., "Rhododendrin inhibits toll-like receptor-7-mediated psoriasis-like skin inflammation in mice", Exp Mol Med 49, e349 (2017).

* cited by examiner

*Primary Examiner* — Kamal A Saeed
*Assistant Examiner* — Meghan C Heasley
(74) *Attorney, Agent, or Firm* — Quarles & Brady, LLP

(57) ABSTRACT

This invention is directed to compositions including IRAK4 inhibitors useful for the treatment of dermatological disorders or conditions characterized by inflammation. This invention is also directed to methods for treating the dermatological disorders or conditions.

25 Claims, 2 Drawing Sheets

IRAK4 INHIBITORS AND TOPICAL USES THEREOF

CROSS-REFERENCE TO RELATED APPLICATIONS

This application claims the benefit of U.S. Provisional Application No. 63/046,531, filed Jun. 30, 2020, the disclosure of which is incorporated herein by reference.

BACKGROUND

Dermatological disorders associated with overactive innate inflammation, such as rosacea, psoriasis, and atopic dermatitis, are common dermatological conditions affecting many people. For example, rosacea is a common and chronic inflammatory skin disease that affects over 10 million Americans. Rosacea presents with at least one of the following symptoms: flushing (transient redness), non-transient redness, papules, pustules, and telangiectases (visible, small dilated blood vessels). Although the phenotypes of rosacea are clinically heterogeneous, they are all related by the presence of chronic facial skin inflammation. Until recently, the pathophysiology of this disease has been poorly understood and limited to descriptions of factors that exacerbate or improve this disorder. Recent molecular studies suggest that an altered innate immune response is involved in the pathogenesis of the vascular and inflammatory disease seen in patients with rosacea. Currently available treatments for rosacea include vasoconstrictors such as alpha blockers or beta blockers, antibiotics, light therapy, and laser therapy.

There is currently a need for a fast-acting, effective and safe dermatological therapy for dermatological disorders that are characterized by inflammation.

SUMMARY

Described herein are topical compositions comprising inhibitors of IRAK4 and TrkA, which may also have low inhibitory activity on VEGFR, and methods for using the IRAK4 inhibitors for the treatment of dermatological disorders or conditions characterized by inflammation, such as rosacea.

In one aspect, the present disclosure provides for a topical composition comprising a dermatologically acceptable excipient and a pharmaceutically effective amount of an IRAK4 inhibitor (e.g., a compound having the following Formula I, II (e.g., Compound 1, et seq.), or III (e.g., Compound 2, et seq.).

In a further aspect, the present disclosure provides for a method for treating a dermatological disorder, the method comprising topically administering to a subject in need thereof a topical composition having a therapeutically effective amount of an IRAK4 inhibitor of Formula I, II (e.g., Compound 1, et seq.), or III (e.g., Compound 2, et seq.); and a dermatologically acceptable excipient.

In a further aspect, the present disclosure provides a method for reducing inflammation in mammalian skin, the method comprising topically administering to the mammalian skin an effective amount of a topical composition including an IRAK4 inhibitor of compound of Formula I, II (e.g., Compound 1, et seq.), or III (e.g., Compound 2, et seq.) to a subject in need thereof.

In a further aspect, the present disclosure provides a method of reducing inflammation and vascular dysfunction in mammalian skin, the method comprising topically administering to the mammalian skin a therapeutically effective amount of a topical composition including an IRAK4 inhibitor a compound of Formula I, II (e.g., Compound 1, et seq.), or III (e.g., Compound 2, et seq.) to a subject in need thereof.

DETAILED DESCRIPTION

Figure 1:
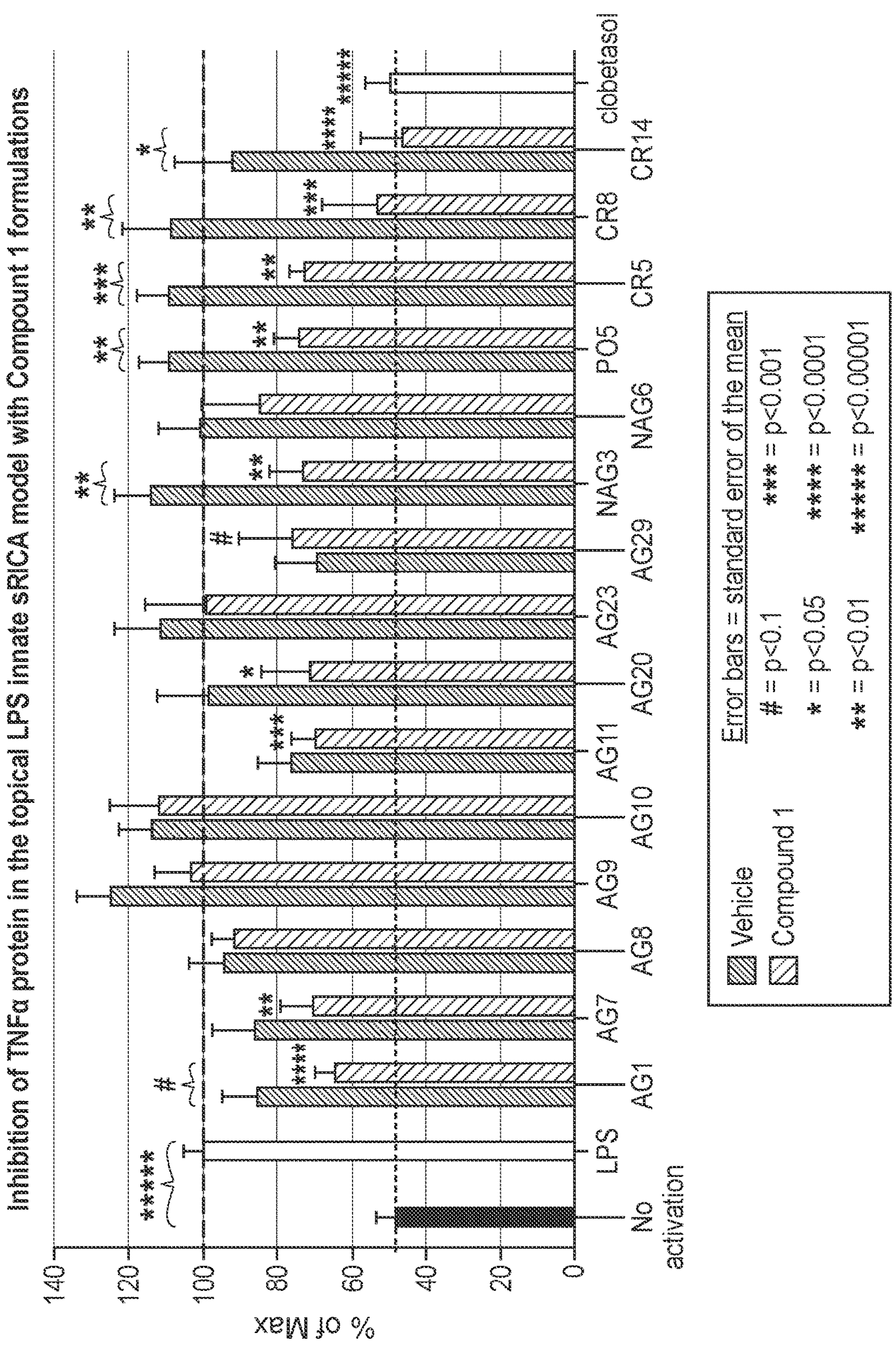
FIG. 1 illustrates the performance of a IRAK4 inhibitor (Compound 1) according to the present disclosure in various vehicle formulations in sRICA. The prepared vehicles are summarized in Tables 29-32.

Provided herein are topical compositions for treating dermatological conditions characterized by inflammation. In particular, the pharmaceutical compositions include compounds that are dual inhibitors of interleukin-1 receptor-associated kinase 4 (IRAK4) and tropomyosin receptor kinase A (TrkA). IRAK4 is a protein involved in signalling innate immune responses downstream from Toll-like receptors (except for TLR3) and IL-1 family cytokine receptors (all MyD88-dependent). TrkA is the high affinity catalytic receptor for nerve growth factor (NGF). While not wishing to be bound by theory, inhibition of IRAK4 and TrkA may potently reverse the overactive innate inflammatory state of the skin, as well as reduce skin vascular abnormality and sensitivity. The topical compositions of IRAK4/TrkA inhibitors are particularly capable of addressing all three key components rosacea pathology including innate inflammation, redness, and sensitivity.

Dual IRAK4 and TrkA Inhibitors

The present disclosure provides compositions comprising compounds having IRAK4 inhibitory properties that also target TrkA.

In one aspect, the present disclosure provides for a topical composition comprising a pharmaceutically effective amount of an IRAK4 inhibitor (e.g., an IRAK4 inhibitor of the present disclosure, e.g., a compound having the following Formula I, II (e.g., Compound 1, et seq.), or III (e.g., Compound 2, et seq.)); a solvent system comprising one or more solvents; and an antioxidant.

In some embodiments, the compound for use in the methods or compositions described herein have Formula I:

Formula I

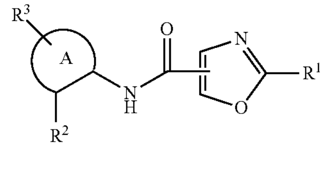

wherein

Ring A is monocyclic heteroaryl;

$R^1$ is optionally substituted monocyclic or bicyclic heteroaryl;

$R^2$ is —$CONH_2$, —CONH—$R^0$, —CONH—$R^{00}$—OH, phenyl, oxadiazolyl, tetrazolyl or the like;

$R^3$ is H, hetero cycloalkyl (optionally substituted by $R^0$, halogen and the like) or the like;

$R^{00}$ is lower alkyl; and $R^{00}$ is lower alkylene, in free or pharmaceutically acceptable salt form, including its racemates, enantiomers and diastereomers.

In some embodiments, the present disclosure provides for a topical composition comprising a compound [Compound 1] according to Formula II:

Formula II

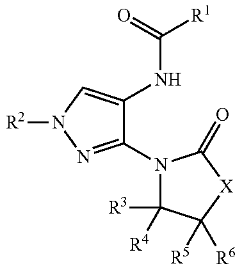

wherein:

$R^1$ is an optionally substituted aromatic heterocyclic group or an optionally substituted $C_{6-14}$ aryl group;

$R^2$ is a hydrogen atom or a substituent;

$R^3$ and $R^4$ are independently a hydrogen atom or a substituent, or $R^3$ and $R^4$ in combination optionally form an optionally substituted ring;

$R^5$ and $R^6$ are independently a hydrogen atom or a substituent, or $R^5$ and $R^6$ in combination optionally form an optionally substituted ring;

X is $CR^7R^8$, $NR^9$, O or S;

$R^7$ and $R^8$ are independently a hydrogen atom or a substituent, or $R^7$ and $R^8$ in combination optionally form an optionally substituted ring; and $R^9$ is a hydrogen atom or a substituent, in free or pharmaceutically acceptable salt form, including its racemates, enantiomers and diastereomers.

The disclosure further provides a compound of Formula II as follows:

1.1 Compound 1, wherein:

$R^1$ is an aromatic, heterocyclic group or a $C_{6-14}$ aryl group, each of which is optionally substituted by 1 to 3 substituents selected from a halogen atom, an optionally substituted $C_{1-6}$ alkyl group, an optionally substituted $C_{6-14}$ aryl group, an optionally substituted heterocyclic group, a $C_{3-10}$ cycloalkylsulfonyl group, a $C_{1-6}$ alkyl-carbonyl group, an aromatic heterocyclylsulfonyl group and a halogenated sulfanyl group;

$R^2$ is an optionally substituted $C_{1-6}$ alkyl group, an optionally substituted $C_{3-10}$ cycloalkyl group or an optionally substituted non-aromatic heterocyclic group;

$R^3$ and $R^4$ are independently a hydrogen atom or an optionally substituted $C_{1-6}$ alkyl group;

$R^5$ and $R^6$ are independently (1) a hydrogen atom, (2) a hydroxy group, (3) an optionally substituted $C_{1-6}$ alkyl group, (4) an optionally substituted $C_{1-6}$ alkoxy group, (5) an amino group optionally mono- or di-substituted by substituent(s) selected from (i) an optionally substituted $C_{1-6}$ alkyl group, (ii) an optionally substituted $C_{1-6}$ alkyl-carbonyl group, and (iii) an optionally substituted $C_{1-6}$ alkylsulfonyl group, (6) an optionally substituted non-aromatic heterocyclic group, (7) a carboxy group, or (8) a carbamoyl group optionally mono- or di-substituted by $C_{1-6}$ alkyl group(s), or $R^5$ and $R^6$ in combination optionally form an optionally substituted non-aromatic heterocycle or an optionally substituted $C_{3-10}$ cycloalkane;

X is $CR^7R^8$, $NR^9$, O or S;

$R^7$ and $R^8$ are independently a hydrogen atom, a cyano group, an optionally substituted $C_{1-6}$ alkyl group or a hydroxy group, or $R^7$ and $R^8$ in combination optionally form an optionally substituted $C_{3-10}$ cycloalkane or an optionally substituted non-aromatic heterocycle; and $R^9$ is a hydrogen atom, an optionally substituted $C_{1-6}$ alkyl group, an optionally substituted $C_{2-6}$ alkenyl group or an optionally substituted $C_{7-16}$ aralkyl group.

1.2 Compound 1 or 1.1, wherein

X is $CR^7R^8$ or $NR^9$; and $R^3$ and $R^4$ are both hydrogen atoms.

1.3 A compound according to Compound 1 or 1.1-1.2, wherein the compound is N-(3-(3-(2-Hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide or a salt thereof.

1.4 A compound according to Compound 1 or 1.1-1.2, wherein the compound is N-(1-Methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide or a salt thereof.

1.5 A compound according to Compound 1 or 1.1-1.2, wherein the compound is N-(1-Methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide or a salt thereof.

Each symbol in formula II is explained below.

$R^1$ is an optionally substituted aromatic heterocyclic group or an optionally substituted $C_{6-14}$ aryl group.

The "aromatic heterocyclic group" of the "optionally substituted aromatic heterocyclic group" and the "$C_{6-14}$ aryl group" of the "optionally substituted $C_{6-14}$ aryl group" for $R^1$ each optionally has 1 to 3 substituents at substitutable position(s). When the number of the substituents is plural, the respective substituents may be the same or different.

In one embodiment, examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include a halogen atom, a cyano group, a nitro group, an optionally substituted hydrocarbon group, an optionally substituted heterocyclic group (the "heterocyclic group" optionally has substituent(s) selected from Substituent Group A (the substituent is optionally further substituted by substituent(s) selected from Substituent Group A)), an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

Preferable examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include (1) an optionally substituted hydrocarbon group (e.g., a hydrocarbon group optionally having substituent(s) selected from Substituent Group A), (2) an optionally substituted heterocyclic group (e.g., a heterocyclic group optionally having substituent(s) selected from Substituent Group A (the substituent is optionally further substituted by substituent(s) selected from Substituent Group A)), and (3) an acyl group.

In another embodiment, examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include a halogen atom, a cyano group, a nitro group, an optionally substituted hydrocarbon group, an optionally substituted heterocyclic group (the "heterocyclic group" optionally has substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))), an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

Preferable examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include (1) a halogen atom, (2) an optionally substituted hydrocarbon group (e.g., a hydrocarbon group optionally having substituent(s) selected from Substituent Group A), (3) an optionally substituted heterocyclic group (e.g., a heterocyclic group optionally having substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))), (4) an acyl group, and (5) an optionally substituted sulfanyl (SH) group.

In one embodiment, $R^1$ is preferably an aromatic heterocyclic group (preferably a 5- to 14-membered aromatic heterocyclic group) or a $C_{6-14}$ aryl group, each of which is optionally substituted by 1 to 3 substituents selected from (1) an optionally substituted $C_{1-6}$ alkyl group (e.g., a $C_{1-6}$ alkyl group optionally having substituent(s) selected from Substituent Group A), (2) an optionally substituted $C_{6-14}$ aryl group (e.g., a $C_{6-14}$ aryl group optionally having substituent(s) selected from Substituent Group A), (3) an optionally substituted heterocyclic group (e.g., a heterocyclic group optionally having substituent(s) selected from Substituent Group A (the substituent is optionally further substituted by substituent(s) selected from Substituent Group A)), (4) a $C_{3-10}$ cycloalkylsulfonyl group, (5) a $C_{1-6}$ alkyl-carbonyl group, and (6) an aromatic heterocyclylsulfonyl group (preferably a 5- to 14-membered aromatic heterocyclylsulfonyl group).

$R^1$ is more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from (1) a $C_{1-6}$ alkyl group (e.g., methyl, ethyl, isopropyl) optionally substituted by 1 to 3 substituents selected from (i) a halogen atom (e.g., a fluorine atom), and (ii) a hydroxy group, (2) a $C_{5-14}$ aryl group (e.g., phenyl) optionally substituted by 1 to 3 halogen atoms (e.g., a fluorine atom), (3) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., ethyl) optionally substituted by 1 to 3 halogen atoms (e.g., a fluorine atom), (4) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl), (5) a $C_{3-10}$ cycloalkylsulfonyl group (e.g., cyclopentylsulfonyl), (6) a $C_{1-6}$ alkyl-carbonyl group (e.g., acetyl), and (7) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

$R^1$ is further more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from (i) a $C_{1-6}$ alkyl group (e.g., methyl, ethyl, isopropyl) optionally substituted by 1 to 3 substituents selected from (a) a halogen atom (e.g., a fluorine atom), and (b) a hydroxy group, (ii) a $C_{6-14}$ aryl group (e.g., phenyl) optionally substituted by 1 to 3 halogen atoms (e.g., a fluorine atom), (iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., ethyl) optionally substituted by 1 to 3 halogen atoms (e.g., a fluorine atom), (iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl), (v) a $C_{3-10}$ cycloalkylsulfonyl group (e.g., cyclopentylsulfonyl), and (vi) a $C_{1-6}$ alkyl-carbonyl group (e.g., acetyl), or (2) a $C_{6-14}$ aryl group (e.g., phenyl) optionally substituted by 1 to 3 substituents selected from (i) a $C_{1-6}$ alkyl group (e.g., methyl), (ii) a $C_{3-10}$ cycloalkylsulfonyl group (e.g., cyclopentylsulfonyl), and (iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

$R^1$ is particularly preferably an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 halogen atoms (e.g., a fluorine atom).

In another embodiment, $R^1$ is more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from (1) a $C_{1-6}$ alkyl group (e.g., methyl, ethyl, isopropyl) optionally substituted by 1 to 3 substituents selected from (i) a halogen atom (e.g., a fluorine atom), and (ii) a hydroxy group, (2) a $C_{6-14}$ aryl group (e.g., phenyl) optionally substituted by 1 to 3 halogen atoms (e.g., a fluorine atom), (3) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., methyl, ethyl) optionally substituted by 1 to 3 substituents selected from (i) a halogen atom (e.g., a fluorine atom), and (ii) a $C_{3-10}$ cycloalkyl group (e.g., cyclopropyl), (4) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl), (5) a $C_{3-10}$ cycloalkylsulfonyl group (e.g., cyclopentylsulfonyl), (6) a $C_{1-6}$ alkyl-carbonyl group (e.g., acetyl), and (7) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

$R^1$ is further more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from (i) a $C_{1-6}$ alkyl group (e.g., methyl, ethyl, isopropyl) optionally substituted by 1 to 3 substituents selected from (a) a halogen atom (e.g., a fluorine atom), and (b) a hydroxy group, (ii) a $C_{6-14}$ aryl group (e.g., phenyl) optionally substituted by 1 to 3 halogen atoms (e.g., a fluorine atom), (iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., methyl, ethyl) optionally substituted by 1 to 3 substituents selected from (a) a halogen atom (e.g., a fluorine atom), and (b) a $C_{3-10}$ cycloalkyl group (e.g., cyclopropyl), (iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl), (v) a $C_{3-10}$ cycloalkylsulfonyl group (e.g., cyclopentylsulfonyl), and (vi) a $C_{1-5}$ alkyl-carbonyl group (e.g., acetyl), or (2) a $C_{6-14}$ aryl group (e.g., phenyl) optionally substituted by 1 to 3 substituents selected from (i) a $C_{1-6}$ alkyl group (e.g., methyl), (ii) a $C_{3-10}$ cycloalkylsulfonyl group (e.g., cyclopentylsulfonyl), and (iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

In yet another embodiment, $R^1$ is preferably an aromatic heterocyclic group (preferably a 5- to 14-membered aromatic heterocyclic group) or a $C_{6-14}$ aryl group, each of which is optionally substituted by 1 to 3 substituents selected from (1) a halogen atom, (2) an optionally substituted $C_{1-6}$ alkyl group (e.g., a $C_{1-6}$ alkyl group optionally having substituent(s) selected from Substituent Group A), (3) an optionally substituted $C_{6-14}$ aryl group (e.g., a $C_{6-14}$ aryl group optionally having substituent(s) selected from Substituent Group A), (4) an optionally substituted heterocyclic group (e.g., a heterocyclic group optionally having substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))), (5) a $C_{3-10}$ cycloalkylsulfonyl group, (6) a $C_{1-6}$ alkyl-carbonyl group, (7) an aromatic heterocyclylsulfonyl group (preferably a 5- to 14-membered aromatic heterocyclylsulfonyl group), and (8) a halogenated sulfanyl group.

$R^1$ is more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from (1) a halogen atom (e.g., a fluorine atom), (2) a $C_{1-6}$ alkyl group (e.g., methyl, ethyl, isopropyl) optionally substituted by 1 to 3 substituents selected from (i) a halogen atom (e.g., a fluorine atom), and (ii) a hydroxy group, (3) a $C_{6-14}$ aryl group (e.g., phenyl) optionally substituted by 1 to 3 halogen atoms (e.g., a fluorine atom), (4) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., pyridyl, thienyl, pyrimidinyl, imidazolyl, pyrazolyl, tetrazolyl, benzimidazolyl (e.g., 1H-benzimidazolyl), thiazolyl) optionally substituted by 1 to 3 substituents selected from (i) an amino group optionally mono- or di-substituted by $C_{1-6}$ alkyl group(s) (e.g., methyl, ethyl) optionally substituted by 1 to 3 substituents selected from (a) a halogen atom (e.g., a fluorine atom), and (b) a $C_{3-10}$ cycloalkyl group (e.g., cyclopropyl), (ii) a halogen atom (e.g., a chlorine atom), (iii) a $C_{1-6}$ alkoxy group (e.g., methoxy), (iv) a cyano group, (v) a $C_{1-6}$ alkyl group (e.g., methyl, ethyl) optionally substituted by 1 to 3 substituents selected from (a) an azido group, (b) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl), (c) a hydroxy group, and (d) a halogen atom (e.g., a fluorine atom), (vi) a formyl group, (vii) a carboxy group, (viii) a carbamoyl group, (ix) a $C_{3-10}$ cycloalkyl group (e.g., cyclopropyl), and (x) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)), (5) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from (i) a $C_{1-6}$ alkyl group (e.g., methyl, ethyl) optionally substituted by 1 to 3 substituents selected from (a) a hydroxy group, (b) an amino group optionally mono- or di-substituted by $C_{1-6}$ alkyl group(s) (e.g., methyl), (c) a cyano group, and (d) a $C_{6-14}$ aryl group (e.g., phenyl), (ii) an oxo group, (iii) a hydroxy group, (iv) a carbamoyl group, and (v) a thioxo group, (6) a $C_{3-10}$ cycloalkylsulfonyl group (e.g., cyclopentylsulfonyl), (7) a $C_{1-6}$ alkyl-carbonyl group (e.g., acetyl), (8) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl), and (9) a halogenated thio group (e.g., pentafluorothio).

$R^1$ is further more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from (i) a $C_{1-6}$ alkyl group (e.g., methyl, ethyl, isopropyl) optionally substituted by 1 to 3 substituents selected from (a) a halogen atom (e.g., a fluorine atom), and (b) a hydroxy group, (ii) a $C_{6-14}$ aryl group (e.g., phenyl) optionally substituted by 1 to 3 halogen atoms (e.g., a fluorine atom), (iii) an aromatic heterocyclic group (preferably a 5- to 14-membered aromatic heterocyclic group, more preferably a 5- to 6-membered monocyclic aromatic heterocyclic group) (e.g., pyridyl, thienyl, pyrimidinyl, pyrazolyl, thiazolyl, imidazolyl) optionally substituted by 1 to 3 substituents selected from (a) an amino group optionally mono- or di-substituted by $C_{1-6}$ alkyl group(s) (e.g., methyl, ethyl) optionally substituted by 1 to 3 substituents selected from (I) a halogen atom (e.g., a fluorine atom), and (II) a $C_{3-10}$ cycloalkyl group (e.g., cyclopropyl), (b) a halogen atom (e.g., a chlorine atom), (c) a $C_{1-6}$ alkoxy group (e.g., methoxy), (d) a cyano group, (e) a $C_{1-6}$ alkyl group (e.g., methyl, ethyl) optionally substituted by 1 to 3 substituents selected from (I) an azido group, (II) an amino group optionally mono- or di-substituted by $C_{1-6}$ alkyl group(s) (e.g., methyl, ethyl)

optionally substituted by 1 to 3 substituents selected from a halogen atom (e.g., a fluorine atom) and a $C_{3-10}$ cycloalkyl group (e.g., cyclopropyl),
(III) a hydroxy group, and
(IV) a halogen atom (e.g., a fluorine atom),
(f) a formyl group,
(g) a carboxy group,
(h) a carbamoyl group,
(i) a $C_{3-10}$ cycloalkyl group (e.g., cyclopropyl), and
(j) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)),
(iv) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from
(a) a $C_{1-6}$ alkyl group (e.g., methyl, ethyl) optionally substituted by 1 to 3 substituents selected from
(I) a hydroxy group,
(II) an amino group optionally mono- or di-substituted by $C_{1-6}$ alkyl group(s) (e.g., methyl),
(III) a cyano group, and
(IV) a $C_{6-14}$ aryl group (e.g., phenyl),
(b) an oxo group,
(c) a hydroxy group,
(d) a carbamoyl group, and
(e) a thioxo group,
(v) a $C_{3-10}$ cycloalkylsulfonyl group (e.g., cyclopentylsulfonyl), and
(vi) a $C_{1-6}$ alkyl-carbonyl group (e.g., acetyl), or
(2) a $C_{6-14}$ aryl group (e.g., phenyl) optionally substituted by 1 to 3 substituents selected from
(i) a halogen atom (e.g., a fluorine atom),
(ii) a $C_{1-6}$ alkyl group (e.g., methyl),
(iii) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., imidazolyl, pyrazolyl, tetrazolyl, benzimidazolyl (e.g., 1H-benzimidazolyl)),
(iv) a $C_{3-10}$ cycloalkylsulfonyl group (e.g., cyclopentylsulfonyl),
(v) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl),
(vi) a halogenated thio group (e.g., pentafluorothio), and
(vii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
(a) a $C_{1-6}$ alkyl group (e.g., methyl) optionally substituted by 1 to 3 amino groups, and
(b) an oxo group.

$R^1$ is still more preferably an aromatic heterocyclic group (preferably a 5- to 14-membered aromatic heterocyclic group, more preferably a 5- to 6-membered monocyclic aromatic heterocyclic group) (e.g., oxazolyl, pyridyl; pyrazolyl) optionally substituted by 1 to 3 substituents selected from
(i) a $C_{1-6}$ alkyl group (e.g., methyl) optionally substituted by 1 to 3 halogen atoms (e.g., a fluorine atom),
(ii) an aromatic heterocyclic group (preferably a 5- to 14-membered aromatic heterocyclic group, more preferably a 5- to 6-membered monocyclic aromatic heterocyclic group) (e.g., pyridyl, pyrazolyl) optionally substituted by 1 to 3 substituents selected from
(a) an amino group optionally mono- or di-substituted by $C_{1-6}$ alkyl group(s) (e.g., methyl, ethyl) optionally substituted by 1 to 3 substituents selected from
(I) a halogen atom (e.g., a fluorine atom), and
(II) a $C_{3-10}$ cycloalkyl group (e.g., cyclopropyl), and
(b) a $C_{1-6}$ alkyl group (e.g., methyl) optionally substituted by 1 to 3 amino groups, and
(iii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
(a) a $C_{1-6}$ alkyl group (e.g., methyl) optionally substituted by 1 to 3 amino groups, and
(b) an oxo group, or
(2) a $C_{6-14}$ aryl group (e.g., phenyl) optionally substituted by 1 to 3 $C_{1-6}$ alkyl groups (e.g., methyl).

$R^1$ is particularly preferably an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 substituents selected from
(1) a halogen atom (e.g., a fluorine atom), and
(2) a $C_{3-10}$ cycloalkyl group (e.g., cyclopropyl).

$R^2$ is a hydrogen atom or a substituent.

In one embodiment, examples of the "substituent" for $R^2$ include those similar to the "substituent" exemplified in the present specification.

The "substituent" for $R^2$ is preferably an optionally substituted hydrocarbon group (e.g., a hydrocarbon group optionally having substituent(s) selected from Substituent Group A), more preferably an optionally substituted $C_{1-6}$ alkyl group (e.g., a $C_{1-6}$ alkyl group optionally having substituent(s) selected from Substituent Group A).

In another embodiment, examples of the "substituent" for $R^2$ include a halogen atom, a cyano group, a nitro group, an optionally substituted hydrocarbon group (the "hydrocarbon group" optionally has substituent(s) selected from Substituent Group A, and a non-aromatic heterocyclic group having oxo group(s)), an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

The "substituent" for $R^2$ is preferably an optionally substituted hydrocarbon group (e.g., a hydrocarbon group optionally having substituent(s) selected from Substituent Group A, and a non-aromatic heterocyclic group having oxo group(s)), or an optionally substituted heterocyclic group (e.g., a heterocyclic group optionally having substituent(s) selected from Substituent Group A), more preferably (1) an optionally substituted $C_{1-6}$ alkyl group (e.g., a $C_{1-6}$ alkyl group optionally having substituent(s) selected from Substituent Group A, and a non-aromatic heterocyclic group (preferably a 3- to 14-membered non-aromatic heterocyclic group) having oxo group(s)), (2) an optionally substituted $C_{3-10}$ cycloalkyl group (e.g., a $C_{3-10}$ cycloalkyl group optionally having substituent (s) selected from Substituent Group A), or (3) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

In one embodiment, $R^2$ is preferably an optionally substituted $C_{1-6}$ alkyl group (e.g., a $C_{1-6}$ alkyl group optionally having substituent(s) selected from Substituent Group A).

In another embodiment, $R^2$ is preferably an optionally substituted $C_{1-6}$ alkyl group (e.g., a $C_{1-6}$ alkyl group optionally having substituent(s) selected from Substituent Group A, and a non-aromatic heterocyclic group (preferably a 3- to 14-membered non-aromatic heterocyclic group) having oxo group(s)), (2) an optionally substituted $C_{3-10}$ cycloalkyl group (e.g., a $C_{3-10}$ cycloalkyl group optionally having substituent (s) selected from Substituent Group A), or (3) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

$R^2$ is more preferably a $C_{1-6}$ alkyl group (e.g., methyl, ethyl) optionally substituted by 1 to 3 substituents selected from (i) a $C_{1-6}$ alkoxy-carbonyl group (e.g., methoxycarbonyl),
(ii) a $C_{1-6}$ alkylsulfonyl group (e.g., methylsulfonyl),
(iii) a carbamoyl group,
(iv) a cyano group,
(v) a non-aromatic heterocyclic group (preferably a 3- to 14-membered non-aromatic heterocyclic group, more preferably a 3- to 8-membered monocyclic non-aromatic heterocyclic group) (e.g., pyrrolidinyl, tetrahydrofuryl, oxetanyl) optionally substituted by 1 to 3 oxo groups, and
(vi) a halogen atom (e.g., a fluorine atom), (2) a $C_{3-10}$ cycloalkyl group (e.g., cyclopentyl) optionally substituted by 1 to 3 hydroxy groups, or (3) anon-aromatic heterocyclic group (preferably a 3- to 14-membered non-aromatic heterocyclic group, more preferably a 3- to 8-membered monocyclic non-aromatic heterocyclic group) (e.g., oxetanyl).

$R^2$ is further more preferably a $C_{1-6}$ alkyl group (e.g., methyl).

$R^3$ and $R^4$ are independently a hydrogen atom or a substituent, or $R^3$ and $R^4$ in combination optionally form an optionally substituted ring.

Examples of the "substituent" for $R^3$ or $R^4$ include those similar to the "substituent" exemplified in the present specification.

The "substituent" for $R^3$ or $R^4$ is preferably an optionally substituted hydrocarbon group (e.g., a hydrocarbon group optionally having substituent(s) selected from Substituent Group A), more preferably an optionally substituted $C_{1-6}$ alkyl group (e.g., a $C_{1-6}$ alkyl group optionally having substituent(s) selected from Substituent Group A).

Examples of the "ring" of the "optionally substituted ring" formed by $R^3$ and $R^4$ include a $C_{3-10}$ cycloalkane, a $C_{3-10}$ cycloalkene and a non-aromatic heterocycle (preferably a 3- to 14-membered non-aromatic heterocycle).

The "ring" of the "optionally substituted ring" formed by $R^3$ and $R^4$ optionally has 1 to 3 substituents selected from Substituent Group A at substitutable position(s). When the number of the substituents is plural, the respective substituents may be the same or different.

$R^3$ and $R^4$ are preferably independently a hydrogen atom or a substituent.

$R^3$ and $R^4$ are more preferably independently a hydrogen atom or an optionally substituted $C_{1-6}$ alkyl group (e.g., a $C_{1-6}$ alkyl group optionally having substituent(s) selected from Substituent Group A).

In one embodiment, $R^3$ and $R^4$ are further more preferably independently a hydrogen atom or a $C_{1-6}$ alkyl group (e.g., methyl).

In another embodiment, $R^3$ and $R^4$ are further more preferably independently (1) a hydrogen atom, or
(2) a $C_{1-6}$ alkyl group (e.g., methyl) optionally substituted by 1 to 3 substituents selected from an amino group optionally mono- or di-substituted by $C_{1-6}$ alkyl group (s) (e.g., methyl).

Still more preferably, one of $R^3$ and $R^4$ is a hydrogen atom, and the other is (1) a hydrogen atom, or
(2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl).

Still further more preferably, one of $R^3$ and $R^4$ is a hydrogen atom, and the other is a hydrogen atom or a $C_{1-6}$ alkyl group (e.g., methyl).

$R^3$ and $R^4$ are particularly preferably both hydrogen atoms.

$R^5$ and $R^6$ are independently a hydrogen atom or a substituent, or $R^5$ and $R^6$ in combination optionally form an optionally substituted ring.

In one embodiment, examples of the "substituent" for $R^5$ or $R^6$ include those similar to the "substituent" exemplified in the present specification.

The "substituent" for $R^5$ or $R^6$ is preferably (1) an optionally substituted hydroxy group,
(2) an optionally substituted hydrocarbon group (e.g., a hydrocarbon group optionally having substituent(s) selected from Substituent Group A),
(3) an optionally substituted amino group, or (4) an optionally substituted heterocyclic group (e.g., a heterocyclic group optionally having substituent(s) selected from Substituent Group A), more preferably (1) a hydroxy group, (2) an optionally substituted $C_{1-6}$ alkyl group (e.g., a C1-6 alkyl group optionally having substituent(s) selected from Substituent Group A), (3) an optionally substituted $C_{1-6}$ alkoxy group (e.g., a $C_{1-6}$ alkoxy group optionally having substituent(s) selected from Substituent Group A), (4) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), or (5) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

In another embodiment, examples of the "substituent" for $R^5$ or $R^6$ include a halogen atom, a cyano group, a nitro group, an optionally substituted hydrocarbon group (the "hydrocarbon group" is optionally substituted by substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group), an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

The "substituent" for $R^5$ or $R^6$ is preferably (1) an optionally substituted hydroxy group, (2) an optionally substituted hydrocarbon group (e.g., a hydrocarbon group optionally having substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group), (3) an optionally substituted amino group, (4), an optionally substituted heterocyclic group (e.g., a heterocyclic group optionally having substituent(s) selected from Substituent Group A), or (5) an acyl group, more preferably (1) a hydroxy group, (2) an optionally substituted $C_{1-6}$ alkyl group (e.g., a $C_{1-6}$ alkyl group optionally having substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group), (3) an optionally substituted $C_{1-6}$ alkoxy group (e.g., a $C_{1-6}$ alkoxy group optionally having substituent(s) selected from Substituent Group A), (4) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), (5) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A), (6) a carboxy group, or (7) a carbamoyl group optionally mono- or di-substituted by $C_{1-6}$ alkyl group(s);

Examples of the "ring" of the "optionally substituted ring" formed by $R^5$ and $R^6$ include a $C_{3-10}$ cycloalkane, a $C_{3-10}$ cycloalkene and a non-aromatic heterocycle (preferably a 3- to 14-membered non-aromatic heterocycle), and preferable examples thereof include a $C_{3-10}$ cycloalkane and a non-aromatic heterocycle (preferably a 3- to 14-membered non-aromatic heterocycle).

The "ring" of the "optionally substituted ring" formed by $R^5$ and $R^6$ optionally has 1 to 3 substituents selected from Substituent Group A at substitutable position(s). When the number of the substituents is plural, the respective substituents may be the same or different.

In one embodiment, $R^5$ and $R^6$ are preferably independently a hydrogen atom or a substituent.

$R^5$ and $R^6$ are more preferably independently (1) a hydrogen atom, (2) a hydroxy group, (3) an optionally substituted $C_{1-6}$ alkyl group (e.g., a C1-6 alkyl group optionally having substituent(s) selected from Substituent Group A), (4) an optionally substituted C1-6 alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), or (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

$R^5$ and $R^6$ are further more preferably independently (1) a hydrogen atom, (2) a hydroxy group, (3) a $C_{1-6}$ alkyl group (e.g., methyl) optionally substituted by 1 to 3 substituents selected from (i) a hydroxy group, and (ii) an amino group optionally mono- or di-substituted by $C_{1-6}$ alkyl group(s) (e.g., methyl, ethyl), (4) a $C_{1-6}$ alkoxy group (e.g., methoxy), (5) an amino group optionally mono- or di-substituted by substituent(s) selected from (i) a $C_{1-6}$ alkyl group (e.g., methyl, ethyl), (ii) a $C_{1-6}$ alkyl-carbonyl group (e.g., acetyl), and (iii) a $C_{1-6}$ alkylsulfonyl group (e.g., methylsulfonyl), or (6) a non-aromatic heterocyclic group (preferably a 3- to 14-membered non-aromatic heterocyclic group, more preferably a 3- to 8-membered monocyclic non-aromatic heterocyclic group) (e.g., morpholinyl).

Still more preferably, one of $R^5$ and $R^6$ is a hydrogen atom, and the other is (1) a hydrogen atom, (2) a hydroxy group, (3) a $C_{1-6}$ alkyl group (e.g., methyl) optionally substituted by 1 to 3 substituents selected from (i) a hydroxy group, and (ii) an amino group optionally mono- or di-substituted by $C_{1-6}$ alkyl group(s) (e.g., methyl, ethyl), (4) a $C_{1-6}$ alkoxy group (e.g., methoxy), (5) an amino group optionally mono- or di-substituted by substituent(s) selected from (i) a $C_{1-6}$ alkyl group (e.g., methyl, ethyl), (ii) a $C_{1-6}$ alkyl-carbonyl group (e.g., acetyl), and (iii) a $C_{1-6}$ alkylsulfonyl group (e.g., methylsulfonyl), or (6) a non-aromatic heterocyclic group (preferably a 3- to 14-membered non-aromatic heterocyclic group, more preferably a 3- to 8-membered monocyclic non-aromatic heterocyclic group) (e.g., morpholinyl).

Particularly preferably, one of $R^5$ and $R^6$ is a hydrogen atom, and the other is (1) a hydrogen atom, (2) a hydroxy group, (3) a C1-6 alkyl group (e.g., methyl) optionally substituted by amino group(s) optionally mono- or di-substituted by $C_{1-6}$ alkyl group(s) (e.g., methyl), or (4) an amino group optionally mono- or di-substituted by $C_{1-6}$ alkyl group(s) (e.g., methyl).

In another embodiment, $R^5$ and $R^6$ are preferably independently (1) a hydrogen atom, (2) a hydroxy group, (3) an optionally substituted $C_{1-6}$ alkyl group (e.g., a $C_{1-6}$ alkyl group optionally having substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a C1-6 alkylsulfonyl group, and (e) a $C_{3-10}$ cycloalkyl-carbonyl group), (4) an optionally substituted C1-6 alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A), (7) a carboxy group, or (8) a carbamoyl group optionally mono- or di-substituted by $C_{1-6}$ alkyl group(s), or $R^5$ and $R^6$ in combination optionally form.

(1) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A), or (2) an optionally substituted $C_{3-10}$ cycloalkane (e.g., a $C_{3-10}$ cycloalkane optionally having substituent(s) selected from Substituent Group A).

$R^5$ and $R^6$ are more preferably independently (1) a hydrogen atom, (2) a hydroxy group, (3) a $C_{1-6}$ alkyl group (e.g., methyl) optionally substituted by 1 to 3 substituents selected from (i) a hydroxy group, (ii) an amino group optionally mono- or di-substituted by substituent(s) selected from (a) a $C_{1-6}$ alkyl group (e.g., methyl, ethyl) optionally substituted by 1 to 3 halogen atoms (e.g., a fluorine atom), (b) a $C_{3-13}$ cycloalkyl group (e.g., cyclopropyl, cyclobutyl) optionally substituted by 1 to 3 halogen atoms (e.g., a fluorine atom), (c) a non-aromatic heterocyclic group (preferably a 3- to 14-membered non-aromatic heterocyclic group, more preferably a 3- to 8-membered monocyclic non-aromatic heterocyclic group) (e.g., oxetanyl), (d) a $C_{1-6}$ alkylsulfonyl group (e.g., methylsulfonyl), (e) a $C_{1-6}$ alkyl-carbonyl group (e.g., acetyl), and (f) a $C_{3-10}$ cycloalkyl-carbonyl group (e.g., cyclopropylcarbonyl), (iii) a halogen atom (e.g., a fluorine atom), (iv) a $C_{1-6}$ alkylsulfanyl group (e.g., methylsulfanyl), (v) a $C_{1-6}$ alkylsulfinyl group (e.g., methylsulfinyl), and (vi) a $C_{1-6}$ alkylsulfonyl group (e.g., methylsulfonyl), (4) a $C_{1-6}$ alkoxy group (e.g., methoxy), (5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane).

Further more preferably, one of $R^5$ and $R^6$ is a hydrogen atom or a $C_{1-6}$ alkyl group (e.g., methyl), and the other is
(1) a hydrogen atom,
(2) a hydroxy group,
(3) a $C_{1-6}$ alkyl group (e.g., methyl) optionally substituted by 1 to 3 substituents selected from
(i) a hydroxy group,
(ii) an amino group optionally mono- or di-substituted by substituent(s) selected from
(a) a $C_{1-6}$ alkyl group (e.g., methyl, ethyl) optionally substituted by 1 to 3 halogen atoms (e.g., a fluorine atom),
(b) a $C_{3-10}$ cycloalkyl group (e.g., cyclopropyl, cyclobutyl) optionally substituted by 1 to 3 halogen atoms (e.g., a fluorine atom),
(c) a non-aromatic heterocyclic group (preferably a 3- to 14-membered non-aromatic heterocyclic group, more preferably a 3- to 8-membered monocyclic non-aromatic heterocyclic group) (e.g., oxetanyl),
(d) a $C_{1-6}$ alkylsulfonyl group (e.g., methylsulfonyl),
(e) a $C_{1-6}$ alkyl-carbonyl group (e.g., acetyl), and
(f) a $C_{3-10}$ cycloalkyl-carbonyl group (e.g., cyclopropylcarbonyl),
(iii) a halogen atom (e.g., a fluorine atom),
(iv) a $C_{1-6}$ alkylsulfanyl group (e.g., methylsulfanyl),
(v) a $C_{1-6}$ alkylsulfinyl group (e.g., methylsulfinyl), and
(vi) a $C_{1-6}$ alkylsulfonyl group (e.g., methylsulfonyl),
(4) a $C_{1-6}$ alkoxy group (e.g., methoxy),
(5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane).

Still more preferably, one of $R^5$ and $R^6$ is a hydrogen atom, and the other is (1) a hydrogen atom,
(2) a hydroxy group,
(3) a C1-6 alkyl group (e.g., methyl) optionally substituted by 1 to 3 substituents selected from
(i) an amino group optionally mono- or di-substituted by $C_{1-6}$ alkyl group(s) (e.g., methyl), and
(ii) a hydroxy group, or
(4) an amino group optionally mono- or di-substituted by $C_{1-6}$ alkyl group(s) (e.g., methyl).

Particularly preferably, one of $R^5$ and $R^6$ is a hydrogen atom, and the other is
(1) a hydrogen atom,
(2) a $C_{1-6}$ alkyl group (e.g., methyl) optionally substituted by amino group(s) optionally mono- or di-substituted by $C_{1-6}$ alkyl group(s) (e.g., methyl), or
(3) an amino group optionally mono- or di-substituted by $C_{1-6}$ alkyl group(s) (e.g., methyl).

Especially, $R^5$ and $R^6$ are particularly preferably both hydrogen atoms.

X is $CR^7R^8$, $NR^9$, O or S.

X is preferably $CR^7R^8$, $NR^9$ or O.

X is more preferably $CR^7R^8$ or $NR^9$.

In one embodiment, X is further more preferably $CR^7R^8$.

In another embodiment, X is further more preferably $NR^9$.

$R^7$ and $R^8$ are independently a hydrogen atom or a substituent, or $R^7$ and $R^8$ in combination optionally form an optionally substituted ring.

Examples of the "substituent" for $R^7$ or $R^8$ include those similar to the "substituent" exemplified in the present specification.

In one embodiment, the "substituent" for $R^7$ or $R^8$ is preferably
(1) a cyano group, or
(2) an optionally substituted hydrocarbon group (e.g., a hydrocarbon group optionally having substituent(s) selected from Substituent Group A),
more preferably
(1) a cyano group, or
(2) an optionally substituted $C_{1-6}$ alkyl group (e.g., a $C_{1-6}$ alkyl group optionally having substituent(s) selected from Substituent Group A).

In another embodiment, the "substituent" for $R^7$ or $R^8$ is preferably
(1) a cyano group,
(2) an optionally substituted hydrocarbon group (e.g., a hydrocarbon group optionally having substituent(s) selected from Substituent Group A), or
(3) an optionally substituted hydroxy group,
more preferably
(1) a cyano group,
(2) an optionally substituted $C_{1-6}$ alkyl group (e.g., a $C_{1-6}$ alkyl group optionally having substituent(s) selected from Substituent Group A), or
(3) a hydroxy group.

Examples of the "ring" of the "optionally substituted ring" formed by $R^7$ and $R^8$ include a $C_{3-10}$ cycloalkane, a $C_{3-10}$ cycloalkene and a non-aromatic heterocycle (preferably a 3- to 14-membered non-aromatic heterocycle), and preferable examples thereof include a $C_{3-10}$ cycloalkane and a non-aromatic heterocycle (preferably a 3- to 14-membered non-aromatic heterocycle).

In one embodiment, the "ring" of the "optionally substituted ring" formed by $R^7$ and $R^8$ optionally has 1 to 3 substituents selected from Substituent Group A at substitutable position(s). When the number of the substituents is plural, the respective substituents may be the same or different.

In another embodiment, the "ring" of the "optionally substituted ring" formed by $R^7$ and $R^8$ optionally has 1 to 3 substituents selected from Substituent Group A and a $C_{7-16}$ aralkyl group at substitutable position(s). When the number of the substituents is plural, the respective substituents may be the same or different.

In one embodiment, $R^7$ and $R^8$ are preferably independently a hydrogen atom or a substituent.

$R^7$ and $R^8$ are more preferably independently
(1) a hydrogen atom,
(2) a cyano group, or
(3) an optionally substituted $C_{1-6}$ alkyl group (e.g., a $C_{1-6}$ alkyl group optionally having substituent(s) selected from Substituent Group A).

$R^7$ and $R^8$ are further more preferably independently
(1) a hydrogen atom,
(2) a cyano group, or
(3) a $C_{1-6}$ alkyl group (e.g., methyl, ethyl).

In another embodiment, $R^7$ and $R^8$ are preferably independently
(1) a hydrogen atom,
(2) a cyano group,
(3) an optionally substituted $C_{1-6}$ alkyl group (e.g., a C1-6 alkyl group optionally having substituent(s) selected from Substituent Group A), or
(4) a hydroxy group, or
$R^7$ and $R^8$ in combination optionally form
(1) an optionally substituted $C_{3-10}$ cycloalkane (e.g., a $C_{3-10}$ cycloalkane optionally having substituent(s) selected from Substituent Group A), or
(2) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A and a $C_{7-16}$ aralkyl group).

$R^7$ and $R^8$ are more preferably independently
(1) a hydrogen atom,
(2) a cyano group,
(3) a $C_{1-6}$ alkyl group (e.g., methyl, ethyl) optionally substituted by 1 to 3 hydroxy groups, or
(4) a hydroxy group, or
$R^7$ and $R^8$ in combination optionally form
(1) a $C_{3-10}$ cycloalkane (e.g., cyclohexane) optionally substituted by 1 to 3 substituents selected from
(i) an oxo group, and
(ii) a hydroxy group, or
(2) a non-aromatic heterocycle (preferably a 3- to 14-membered non-aromatic heterocycle, more preferably a 3- to 8-membered monocyclic non-aromatic heterocycle) (e.g., pyrrolidine, piperidine) optionally substituted by 1 to 3 $C_{7-15}$ aralkyl groups (e.g., benzyl).

$R^7$ and $R^8$ are further more preferably independently
(1) a hydrogen atom, or
(2) a $C_{1-6}$ alkyl group (e.g., methyl).

$R^9$ is a hydrogen atom or a substituent.

Examples of the "substituent" for $R^9$ include those similar to the "substituent" exemplified in the present specification.

In one embodiment, the "substituent" for $R^9$ is preferably an optionally substituted hydrocarbon group (e.g., a hydrocarbon group optionally having substituent(s) selected from Substituent Group A), more preferably an optionally substituted $C_{1-6}$ alkyl group (e.g., a $C_{1-6}$ alkyl group optionally having substituent(s) selected from Substituent Group A).

In another embodiment, the "substituent" for $R^9$ is preferably an optionally substituted hydrocarbon group, more preferably
(1) an optionally substituted $C_{1-6}$ alkyl group (e.g., a $C_{1-6}$ alkyl group optionally having substituent(s) selected from Substituent Group A),
(2) an optionally substituted $C_{2-6}$ alkenyl group (e.g., a $C_{2-6}$ alkenyl group optionally having substituent(s) selected from Substituent Group A), or
(3) an optionally substituted $C_{7-16}$ aralkyl group (e.g., a $C_{7-16}$ aralkyl group optionally having substituent(s) selected from Substituent Group A).

In one embodiment, $R^9$ is preferably an optionally substituted $C_{1-6}$ alkyl group (e.g., a $C_{1-6}$ alkyl group optionally having substituent(s) selected from Substituent Group A).

$R^9$ is more preferably a $C_{1-6}$ alkyl group (e.g., methyl, ethyl) optionally substituted by 1 to 3 substituents selected from
(1) a hydroxy group, and
(2) a $C_{1-6}$ alkoxy group (e.g., methoxy) optionally substituted by 1 to 3 $C_{6-14}$ aryl groups (e.g., phenyl).

In another embodiment, $R^9$ is preferably a hydrogen atom or an optionally substituted $C_{1-6}$ alkyl group (e.g., a $C_{1-6}$ alkyl group optionally having substituent(s) selected from Substituent Group A).

$R^9$ is more preferably
(1) a hydrogen atom, or
(2) a $C_{1-6}$ alkyl group (e.g., methyl, ethyl) optionally substituted by 1 to 3 substituents selected from
(i) a hydroxy group, and
(ii) a $C_{1-6}$ alkoxy group (e.g., methoxy) optionally substituted by 1 to 3 $C_{6-14}$ aryl groups (e.g., phenyl).

In yet another embodiment, $R^9$ is preferably
(1) a hydrogen atom,
(2) an optionally substituted $C_{1-6}$ alkyl group (e.g., a $C_{1-6}$ alkyl group optionally having substituent(s) selected from Substituent Group A),
(3) an optionally substituted $C_{2-6}$ alkenyl group (e.g., a $C_{2-6}$ alkenyl group optionally having substituent(s) selected from Substituent Group A), or
(4) an optionally substituted $C_{7-16}$ aralkyl group (e.g., a $C_{7-16}$ aralkyl group optionally having substituent(s) selected from Substituent Group A).

$R^9$ is more preferably
(1) a hydrogen atom, or
(2) a $C_{1-6}$ alkyl group (e.g., methyl, ethyl, propyl, isopropyl) optionally substituted by 1 to 3 substituents selected from
(i) a hydroxy group,
(ii) a $C_{1-6}$ alkoxy group (e.g., methoxy) optionally substituted by 1 to 3 $C_{6-14}$ aryl groups (e.g., phenyl), and
(iii) an amino group optionally mono- or di-substituted by $C_{1-6}$ alkyl group(s) (e.g., methyl),
(3) a $C_{2-6}$ alkenyl group (e.g., allyl), or
(4) a $C_{7-16}$ aralkyl group (e.g., benzyl) optionally substituted by 1 to 3 $C_{1-6}$ alkoxy groups (e.g., methoxy).

$R^9$ is further more preferably
(1) a hydrogen atom, or
(2) a $C_{1-6}$ alkyl group (e.g., methyl, ethyl, propyl, preferably methyl, ethyl) optionally substituted by 1 to 3 hydroxy groups.

Preferable examples of compound (1) include the following compounds:

[Compound A-1]

Compound (I) wherein $R^1$ is an aromatic heterocyclic group (preferably a 5- to 14-membered aromatic heterocyclic group) or a $C_{6-14}$ aryl group, each of which is optionally substituted by 1 to 3 substituents selected from (1) an optionally substituted $C_{1-6}$ alkyl group (e.g., a $C_{1-6}$ alkyl group optionally having substituent(s) selected from Substituent Group A), (2) an optionally substituted $C_{6-14}$ aryl group (e.g., a $C_{6-14}$ aryl group optionally having substituent(s) selected from Substituent Group A), (3) an optionally substituted heterocyclic group (e.g., a heterocyclic group optionally having substituent(s) selected from Substituent Group A (the substituent is optionally further substituted by substituent(s) selected from Substituent Group A)), (4) a $C_{3-10}$ cycloalkylsulfonyl group, (5) a $C_{1-6}$ alkyl-carbonyl group, and (6) an aromatic heterocyclylsulfonyl group (preferably a 5- to 14-membered aromatic heterocyclylsulfonyl group);

$R^2$ is an optionally substituted $C_{1-6}$ alkyl group (e.g., a $C_{1-6}$ alkyl group optionally having substituent(s) selected from Substituent Group A);

$R^3$ and $R^4$ are independently a hydrogen atom or an optionally substituted $C_{1-6}$ alkyl group (e.g., a $C_{1-6}$ alkyl group optionally having substituent(s) selected from Substituent Group A);

$R^5$ and $R^6$ are independently (1) a hydrogen atom, (2) a hydroxy group, (3) an optionally substituted $C_{1-6}$ alkyl group (e.g., a $C_{1-6}$ alkyl group optionally having substituent(s) selected from Substituent Group A), (4) an optionally substituted $C_{1-6}$ alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), or (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A);

X is $CR^7R^8$, $NR^9$ or O;

$R^7$ and $R^8$ are independently (1) a hydrogen atom, (2) a cyano group, or (3) an optionally substituted $C_{1-6}$ alkyl group (e.g., a $C_{1-6}$ alkyl group optionally having substituent(s) selected from Substituent Group A); and $R^9$ is an optionally substituted $C_{1-6}$ alkyl group (e.g., a $C_{1-6}$ alkyl group optionally having substituent(s) selected from Substituent Group A).

[Compound A-2]

Compound (I) wherein $R^1$ is an aromatic heterocyclic group (preferably a 5- to 14-membered aromatic heterocyclic group) or a $C_{6-14}$ aryl group, each of which is optionally substituted by 1 to 3 substituents selected from (1) an optionally substituted $C_{1-6}$ alkyl group (e.g., a $C_{1-6}$ alkyl group optionally having substituent(s) selected from Substituent Group A), (2) an optionally substituted $C_{6-14}$ aryl group (e.g., a $C_{6-14}$ aryl group optionally having substituent(s) selected from Substituent Group A), (3) an optionally substituted heterocyclic group (e.g., a heterocyclic group optionally having substituent(s) selected from Substituent Group A (the substituent is optionally further substituted by substituent(s) selected from Substituent Group A)), (4) a $C_{3-10}$ cycloalkylsulfonyl group, (5) a $C_{1-6}$ alkyl-carbonyl group, and (6) an aromatic heterocyclylsulfonyl group (preferably a 5- to 14-membered aromatic heterocyclylsulfonyl group);

$R^2$ is an optionally substituted $C_{1-6}$ alkyl group (e.g., a $C_{1-6}$ alkyl group optionally having substituent(s) selected from Substituent Group A);

$R^3$ and $R^4$ are independently a hydrogen atom or an optionally substituted $C_{1-6}$ alkyl group (e.g., a $C_{1-6}$ alkyl group optionally having substituent(s) selected from Substituent Group A);

$R^5$ and $R^6$ are independently (1) a hydrogen atom, (2) a hydroxy group, (3) an optionally substituted $C_{1-6}$ alkyl group (e.g., a $C_{1-6}$ alkyl group optionally having substituent(s) selected from Substituent Group A), (4) an optionally substituted $C_{1-6}$ alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), or (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A);

X is $CR^7R^6$, $NR^9$ or O;

$R^7$ and $R^8$ are independently (1) a hydrogen atom, (2) a cyano group, or (3) an optionally substituted $C_{1-6}$ alkyl group (e.g., a $C_{1-6}$ alkyl group optionally having substituent(s) selected from Substituent Group A); and $R^9$ is a hydrogen atom or an optionally substituted $C_{1-6}$ alkyl group (e.g., a $C_{1-6}$ alkyl group optionally having substituent(s) selected from Substituent Group A).

[Compound A-3]

Compound (I) wherein $R^1$ is an aromatic heterocyclic group (preferably a 5- to 14-membered aromatic heterocyclic group) or a $C_{6-14}$ aryl group, each of which is optionally substituted by 1 to 3 substituents selected from (1) a halogen-atom, (2) an optionally substituted $C_{1-6}$ alkyl group (e.g., a $C_{1-6}$ alkyl group optionally having substituent(s) selected from Substituent Group A), (3) an optionally substituted $C_{6-14}$ aryl group (e.g., a $C_{6-14}$ aryl group optionally having substituent(s) selected from Substituent Group A), (4) an optionally substituted heterocyclic group (e.g., a heterocyclic group optionally having substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))), (5) a $C_{3-10}$ cycloalkylsulfonyl group, (6) a $C_{1-6}$ alkyl-carbonyl group, (7) an aromatic heterocyclylsulfonyl group (preferably a 5- to 14-membered aromatic heterocyclylsulfonyl group), and (8) a halogenated sulfanyl group;

$R^2$ is (1) an optionally substituted $C_{1-6}$ alkyl group (e.g., a $C_{1-6}$ alkyl group optionally having substituent(s) selected from Substituent Group A, and a non-aromatic heterocyclic group (preferably a 3- to 14-membered non-aromatic heterocyclic group) having oxo group(s)), (2) an optionally substituted $C_{3-10}$ cycloalkyl group (e.g., a $C_{3-10}$ cycloalkyl group optionally having substituent(s) selected from Substituent Group A), or (3) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A); $R^3$ and $R^4$ are independently a hydrogen atom or an optionally substituted $C_{1-6}$ alkyl group (e.g., a $C_{1-6}$ alkyl group optionally having substituent(s) selected from Substituent Group A);

$R^5$ and $R^6$ are independently (1) a hydrogen atom, (2) a hydroxy group, (3) an optionally substituted $C_{1-6}$ alkyl group (e.g., a $C_{1-6}$ alkyl group optionally having substituent(s) selected from (1) Substituent Group A, and (2) an amino group mono- or di-substituted by substituent (s) selected, from (a) a $C_{1-5}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group), (4) an optionally substituted $C_{1-6}$ alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A), (7) a carboxy group, or (8) a carbamoyl group optionally mono- or di-substituted by $C_{1-6}$ alkyl group(s), or $R^5$ and $R^6$ in combination optionally form (1) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A), or (2) an optionally substituted $C_{3-10}$ cycloalkane (e.g., a $C_{3-10}$ cycloalkane optionally having substituent(s) selected from Substituent Group A);

X is $CR^7R^8$, $NR^9$, O or S;

$R^7$ and $R^8$ are independently (1) a hydrogen atom, (2) a cyano group, (3) an optionally substituted $C_{1-6}$ alkyl group (e.g., a $C_{1-6}$ alkyl group optionally having substituent(s) selected from Substituent Group A), or (4) a hydroxy group, or $R^7$ and $R^8$ in combination optionally form (1) an optionally substituted $C_{3-10}$ cycloalkane (e.g., a $C_{3-10}$ cycloalkane optionally having substituent(s) selected from Substituent Group A), or (2) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A and a $C_{7-16}$ aralkyl group); and $R^9$ is (1) a hydrogen atom, (2) an optionally substituted $C_{1-6}$ alkyl group (e.g., a $C_{1-6}$ alkyl group optionally having substituent(s) selected from Substituent Group A), (3) an optionally substituted $C_{2-6}$ alkenyl group (e.g., a $C_{2-6}$ alkenyl group optionally having substituent(s) selected from Substituent Group A), or (4) an optionally substituted $C_{7-16}$ aralkyl group (e.g., a $C_{7-16}$ aralkyl group optionally having substituent(s) selected from Substituent Group A).

[Compound B-1]

Compound (I) wherein $R^1$ is (1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo [1,2-b]pyridazinyl), pyrazolopyrimidinyl (e.g., pyrazolo[1,5-a]pyrimidinyl)) optionally substituted by 1 to 3 substituents selected from (i) a $C_{1-6}$ alkyl group (e.g., methyl, ethyl, isopropyl) optionally substituted by 1 to 3 substituents selected from (a) a halogen atom (e.g., a fluorine atom), and
(b) a hydroxy group,
(ii) a $C_{6-14}$ aryl group (e.g., phenyl) optionally substituted by 1 to 3 halogen atoms (e.g., a fluorine atom),
(iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., ethyl) optionally substituted by 1 to 3 halogen atoms (e.g., a fluorine atom),
(iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl),
(v) a $C_{3-10}$ cycloalkylsulfonyl group (e.g., cyclopentylsulfonyl), and
(vi) a $C_{1-6}$ alkyl-carbonyl group (e.g., acetyl), or
(2) a $C_{6-14}$ aryl group (e.g., phenyl) optionally substituted by 1 to 3 substituents selected from
(i) a $C_{1-6}$ alkyl group (e.g., methyl),
(ii) a $C_{3-10}$ cycloalkylsulfonyl group (e.g., cyclopentylsulfonyl), and
(iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl);
$R^2$ is a $C_{1-6}$ alkyl group (e.g., methyl);
$R^3$ and $R^4$ are independently a hydrogen atom or a $C_{1-6}$ alkyl group (e.g., methyl);
$R^5$ and $R^6$ are independently
(1) a hydrogen atom,
(2) a hydroxy group,
(3) a $C_{1-6}$ alkyl group (e.g., methyl) optionally substituted by 1 to 3 substituents selected from
(i) a hydroxy group, and
(ii) an amino group optionally mono- or di-substituted by $C_{1-6}$ alkyl group(s) (e.g., methyl, ethyl),
(4) a $C_{1-6}$ alkoxy group (e.g., methoxy),
(5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl), or
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl);
X is $CR^7R^8$, $NR^9$ or O;
$R^7$ and $R^8$ are independently
(1) a hydrogen atom,
(2) a cyano group, or
(3) a $C_{1-6}$ alkyl group (e.g., methyl, ethyl); and
$R^9$ is a $C_{1-6}$ alkyl group (e.g., methyl, ethyl) optionally substituted by 1 to 3 substituents selected from
(1) a hydroxy group, and
(2) a $C_{1-6}$ alkoxy group (e.g., methoxy) optionally substituted by 1 to 3 $C_{6-14}$ aryl groups (e.g., phenyl).

[Compound B-2]
Compound (I) wherein
$R^1$ is
(1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
(i) a $C_{1-6}$ alkyl group (e.g., methyl, ethyl, isopropyl) optionally substituted by 1 to 3 substituents selected from
(a) a halogen atom (e.g., a fluorine atom), and
(b) a hydroxy group,
(ii) a $C_{6-14}$ aryl group (e.g., phenyl) optionally substituted by 1 to 3 halogen atoms (e.g., a fluorine atom),
(iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., methyl, ethyl) optionally substituted by 1 to 3 substituents selected from
(a) a halogen atom (e.g., a fluorine atom), and
(b) a $C_{3-10}$ cycloalkyl group (e.g., cyclopropyl),
(iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-5}$ alkyl groups (e.g., methyl),
(v) a $C_{3-10}$ cycloalkylsulfonyl group (e.g., cyclopentylsulfonyl), and
(vi) a $C_{1-6}$ alkyl-carbonyl group (e.g., acetyl), or
(2) a $C_{6-14}$ aryl group (e.g., phenyl) optionally substituted by 1 to 3 substituents selected from
(i) a $C_{1-6}$ alkyl group (e.g., methyl),
(ii) a $C_{3-10}$ cycloalkylsulfonyl group (e.g., cyclopentylsulfonyl), and
(iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl);
$R^2$ is a $C_{1-6}$ alkyl group (e.g., methyl);
$R^3$ and $R^4$ are independently a hydrogen atom or a $C_{1-6}$ alkyl group (e.g., methyl);
$R^5$ and $R^6$ are independently
(1) a hydrogen atom,
(2) a hydroxy group,
(3) a $C_{1-6}$ alkyl group (e.g., methyl) optionally substituted by 1 to 3 substituents selected from
(i) a hydroxy group, and
(ii) an amino group optionally mono- or di-substituted by $C_{1-6}$ alkyl group(s) (e.g., methyl, ethyl),
(4) a $C_{1-6}$ alkoxy group (e.g., methoxy),
(5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl), or
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl);

X is $CR^7R^8$, $NR^9$ or O;

$R^7$ and $R^8$ are independently (1) a hydrogen atom, (2) a cyano group, or (3) a $C_{1-6}$ alkyl group (e.g., methyl, ethyl); and $R^9$ is (1) a hydrogen atom, or (2) a $C_{1-6}$ alkyl group (e.g., methyl, ethyl) optionally substituted by 1 to 3 substituents selected from (i) a hydroxy group, and (ii) a $C_{1-6}$ alkoxy group (e.g., methoxy) optionally substituted by 1 to 3 $C_{6-14}$ aryl groups (e.g., phenyl).

[Compound B-3]

Compound (I) wherein $R^1$ is an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from (1) a halogen atom (e.g., a fluorine atom), (2) a $C_{1-6}$ alkyl group (e.g., methyl, ethyl, isopropyl) optionally substituted by 1 to 3 substituents selected from (i) a halogen atom (e.g., a fluorine atom), and (ii) a hydroxy group, (3) a $C_{6-14}$ aryl group (e.g., phenyl) optionally substituted by 1 to 3 halogen atoms (e.g., a fluorine atom), (4) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., pyridyl, thienyl, pyrimidinyl, imidazolyl, pyrazolyl, tetrazolyl, benzimidazolyl (e.g., 1H-benzimidazolyl), thiazolyl) optionally substituted by 1 to 3 substituents selected from (i) an amino group optionally mono- or di-substituted by $C_{1-6}$ alkyl group(s) (e.g., methyl, ethyl) optionally substituted by 1 to 3 substituents selected from (a) a halogen atom (e.g., a fluorine atom), and (b) a $C_{3-10}$ cycloalkyl group (e.g., cyclopropyl), (ii) a halogen atom (e.g., a chlorine atom), (iii) a $C_{1-6}$ alkoxy group (e.g., methoxy), (iv) a cyano group, (v) a $C_{1-6}$ alkyl group (e.g., methyl, ethyl) optionally substituted by 1 to 3 substituents selected from (a) an azido group, (b) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl), (c) a hydroxy group, and (d) a halogen atom (e.g., a fluorine atom), (vi) a formyl group, (vii) a carboxy group, (viii) a carbamoyl group, (ix) a $C_{3-10}$ cycloalkyl group (e.g., cyclopropyl), and (x) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)), (5) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from (i) a $C_{1-6}$ alkyl group (e.g., methyl, ethyl) optionally substituted by 1 to 3 substituents selected from (a) a hydroxy group, (b) an amino group optionally mono- or di-substituted by $C_{1-6}$ alkyl group(s) (e.g., methyl), (c) a cyano group, and (d) a $C_{6-14}$ aryl group (e.g., phenyl), (ii) an oxo group, (iii) a hydroxy group, (iv) a carbamoyl group, and (v) a thioxo group, (6) a $C_{3-10}$ cycloalkylsulfonyl group (e.g., cyclopentylsulfonyl), (7) a $C_{1-6}$ alkyl-carbonyl group (e.g., acetyl), (8) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl), and (9) a halogenated thio group (e.g., pentafluorothio);

$R^2$ is (1) a $C_{1-6}$ alkyl group (e.g., methyl, ethyl) optionally substituted by 1 to 3 substituents selected from (i) a $C_{1-6}$ alkoxy-carbonyl group (e.g., methoxycarbonyl), (ii) a $C_{1-6}$ alkylsulfonyl group (e.g., methylsulfonyl), (iii) a carbamoyl group, (iv) a cyano group, (v) a non-aromatic heterocyclic group (preferably a 3- to 14-membered non-aromatic heterocyclic group, more preferably a 3- to 8-membered monocyclic non-aromatic heterocyclic group) (e.g., pyrrolidinyl, tetrahydrofuryl, oxetanyl) optionally substituted by 1 to 3 oxo groups, and (vi) a halogen atom (e.g., a fluorine atom), (2) a $C_{3-10}$ cycloalkyl group (e.g., cyclopentyl) optionally substituted by 1 to 3 hydroxy groups, or (3) a non-aromatic heterocyclic group (preferably a 3- to 14-membered non-aromatic heterocyclic group, more preferably a 3- to 8-membered monocyclic non-aromatic heterocyclic group) (e.g., oxetanyl);

$R^3$ and $R^4$ are independently
(1) a hydrogen atom, or
(2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl);
$R^5$ and $R^6$ are independently
(1) a hydrogen atom,
(2) a hydroxy group,
(3) a $C_{1-6}$ alkyl group (e.g., methyl) optionally substituted by 1 to 3 substituents selected from
(i) a hydroxy group,
(ii) an amino group optionally mono- or di-substituted by substituent(s) selected from
(a) a $C_{1-6}$ alkyl group (e.g., methyl, ethyl) optionally substituted by 1 to 3 halogen atoms (e.g., a fluorine atom),
(b) a $C_{3-10}$ cycloalkyl group (e.g., cyclopropyl, cyclobutyl) optionally substituted by 1 to 3 halogen atoms (e.g., a fluorine atom),
(c) a non-aromatic heterocyclic group (preferably a 3- to 14-membered non-aromatic heterocyclic group, more preferably a 3- to 8-membered monocyclic non-aromatic heterocyclic group) (e.g., oxetanyl),
(d) a $C_{1-6}$ alkylsulfonyl group (e.g., methylsulfonyl),
(e) a $C_{1-6}$ alkyl-carbonyl group (e.g., acetyl), and
(f) a $C_{3-10}$ cycloalkyl-carbonyl group (e.g., cyclopropylcarbonyl),
(iii) a halogen atom (e.g., a fluorine atom),
(iv) a $C_{1-6}$ alkylsulfanyl group (e.g., methylsulfanyl),
(v) a $C_{1-6}$ alkylsulfinyl group (e.g., methylsulfinyl), and
(vi) a $C_{1-6}$ alkylsulfonyl group (e.g., methylsulfonyl),
(4) a $C_{1-6}$ alkoxy group (e.g., methoxy),
(5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane);
X is $CR^7R^9$, $NR^9$, O or S;
$R^7$ and $R^8$ are independently
(1) a hydrogen atom,
(2) a cyano group,
(3) a 01-6 alkyl group (e.g., methyl, ethyl) optionally substituted by 1 to 3 hydroxy groups, or
(4) a hydroxy group, or
$R^7$ and $R^8$ in combination optionally form
(1) a $C_{3-10}$ cycloalkane (e.g., cyclohexane) optionally substituted by 1 to 3 substituents selected from
(i) an oxo group, and
(ii) a hydroxy group, or
(2) a non-aromatic heterocycle (preferably a 3- to 14-membered non-aromatic heterocycle, more preferably a 3- to 8-membered monocyclic non-aromatic heterocycle) (e.g., pyrrolidine, piperidine) optionally substituted by 1 to 3 $C_{7-16}$ aralkyl groups (e.g., benzyl); and
$R^9$ is
(1) a hydrogen atom, or
(2) a $C_{1-6}$ alkyl group (e.g., methyl, ethyl, propyl, isopropyl) optionally substituted by 1 to 3 substituents selected from
(i) a hydroxy group,
(ii) a $C_{1-6}$ alkoxy group (e.g., methoxy) optionally substituted by 1 to 3 $C_{6-14}$ aryl groups (e.g., phenyl), and
(iii) an amino group optionally mono- or di-substituted by $C_{1-6}$ alkyl group(s) (e.g., methyl),
(3) a $C_{2-6}$ alkenyl group (e.g., allyl), or
(4) a $C_{7-16}$ aralkyl group (e.g., benzyl) optionally substituted by 1 to 3 $C_{1-6}$ alkoxy groups (e.g., methoxy).

[Compound B-4]
Compound (I) wherein
$R^1$ is
(1) an aromatic heterocyclic group (preferably a 5- to 14 membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
(i) a $C_{1-6}$ alkyl group (e.g., methyl, ethyl, isopropyl) optionally substituted by 1 to 3 substituents selected from
(a) a halogen atom (e.g., a fluorine atom), and
(b) a hydroxy group,
(ii) a $C_{6-14}$ aryl group (e.g., phenyl) optionally substituted by 1 to 3 halogen atoms (e.g., a fluorine atom),
(iii) an aromatic heterocyclic group (preferably a 5- to 14-membered aromatic heterocyclic group, more preferably a 5- to 6-membered monocyclic aromatic heterocyclic group) (e.g., pyridyl, thienyl, pyrimidinyl, pyrazolyl, thiazolyl, imidazolyl) optionally substituted by 1 to 3 substituents selected from
(a) an amino group optionally mono- or di-substituted by $C_{1-6}$ alkyl group(s) (e.g., methyl, ethyl) optionally substituted by 1 to 3 substituents selected from
(I) a halogen atom (e.g., a fluorine atom), and
(II) a $C_{3-10}$ cycloalkyl group (e.g., cyclopropyl),
(b) a halogen atom (e.g., a chlorine atom),
(c) a $C_{1-6}$ alkoxy group (e.g., methoxy),
(d) a cyano group,
(e) a $C_{1-6}$ alkyl group (e.g., methyl, ethyl) optionally substituted by 1 to 3 substituents selected from
(I) an azido group,
(II) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl),
(III) a hydroxy group, and
(IV) a halogen atom (e.g., a fluorine atom),
(f) a formyl group,
(g) a carboxy group,
(h) a carbamoyl group, (i) a $C_{3-10}$ cycloalkyl group (e.g., cyclopropyl), and (j) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)), (iv) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from (a) a $C_{1-6}$ alkyl group (e.g., methyl, ethyl) optionally substituted by 1 to 3 substituents selected from (I) a hydroxy group, (II) an amino group optionally mono- or di-substituted by $C_{1-6}$ alkyl group(s) (e.g., methyl), (III) a cyano group, and (IV) a $C_{6-14}$ aryl group (e.g., phenyl), (b) an oxo group, (c) a hydroxy group, (d) a carbamoyl group, and (e) a thioxo group, (v) a $C_{3-10}$ cycloalkylsulfonyl group (e.g., cyclopentylsulfonyl), and (vi) a $C_{1-6}$ alkyl-carbonyl group (e.g., acetyl), or (2) a $C_{6-14}$ aryl group (e.g., phenyl) optionally substituted by 1 to 3 substituents selected from (i) a halogen atom (e.g., a fluorine atom), (ii) a $C_{1-6}$ alkyl group (e.g., methyl), (iii) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., imidazolyl, pyrazolyl, tetrazolyl, benzimidazolyl (e.g., 1H-benzimidazolyl)), (iv) a $C_{3-10}$ cycloalkylsulfonyl group (e.g., cyclopentylsulfonyl), (v) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl), (vi) a halogenated thio group (e.g., pentafluorothio), and (vii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from (a) a $C_{1-6}$ alkyl group (e.g., methyl) optionally substituted by 1 to 3 amino groups, and (b) an oxo group;

$R^2$ is (1) a $C_{1-6}$ alkyl group (e.g., methyl, ethyl) optionally substituted by 1 to 3 substituents selected from (i) a $C_{1-6}$ alkoxy-carbonyl group (e.g., methoxycarbonyl), (ii) a $C_{1-6}$ alkylsulfonyl group (e.g., methylsulfonyl), (iii) a carbamoyl group, (iv) a cyano group, (v) a non-aromatic heterocyclic group (preferably a 3- to 14-membered non-aromatic heterocyclic group, more preferably a 3- to 8-membered monocyclic non-aromatic heterocyclic group) (e.g., pyrrolidinyl, tetrahydrofuryl, oxetanyl) optionally substituted by 1 to 3 oxo groups, and (vi) a halogen atom (e.g., a fluorine atom), (2) a $C_{3-10}$ cycloalkyl group (e.g., cyclopentyl) optionally substituted by 1 to 3 hydroxy groups, or (3) a non-aromatic heterocyclic group (preferably a 3- to 14-membered non-aromatic heterocyclic group, more preferably a 3- to 8-membered monocyclic non-aromatic heterocyclic group) (e.g., oxetanyl);

one of $R^3$ and $R^4$ is a hydrogen atom, and the other is (1) a hydrogen atom, or (2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl);

one of $R^5$ and $R^6$ is a hydrogen atom or a $C_{1-6}$ alkyl group (e.g., methyl), and the other is (1) a hydrogen atom, (2) a hydroxy group, (3) a $C_{1-6}$ alkyl group (e.g., methyl) optionally substituted by 1 to 3 substituents selected from (i) a hydroxy group, (ii) an amino group optionally mono- or di-substituted by substituent(s) selected from (a) a $C_{1-6}$ alkyl group (e.g., methyl, ethyl) optionally substituted by 1 to 3 halogen atoms (e.g., a fluorine atom), (b) a $C_{3-10}$ cycloalkyl group (e.g., cyclopropyl, cyclobutyl) optionally substituted by 1 to 3 halogen atoms (e.g., a fluorine atom), (c) a non-aromatic heterocyclic group (preferably a 3- to 14-membered non-aromatic heterocyclic group, more preferably a 3- to 8-membered monocyclic non-aromatic heterocyclic group) (e.g., oxetanyl), (d) a $C_{1-6}$ alkylsulfonyl group (e.g., methylsulfonyl), (e) a $C_{1-6}$ alkyl-carbonyl group (e.g., acetyl), and (f) a $C_{3-10}$ cycloalkyl-carbonyl group (e.g., cyclopropylcarbonyl), (iii) a halogen atom (e.g., a fluorine atom), (iv) a $C_{1-6}$ alkylsulfanyl group (e.g., methylsulfanyl), (v) a $C_{1-6}$ alkylsulfinyl group (e.g., methylsulfinyl), and (vi) a $C_{1-6}$ alkylsulfonyl group (e.g., methylsulfonyl), (4) a $C_{1-6}$ alkoxy group (e.g., methoxy), (5) an amino group optionally mono- or di-substituted by substituent(s) selected from (i) a $C_{1-6}$ alkyl group (e.g., methyl, ethyl), (ii) a $C_{1-6}$ alkyl-carbonyl group (e.g., acetyl), and (iii) a $C_{1-6}$ alkylsulfonyl group (e.g., methylsulfonyl), (6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane);
X is $CR^7R^8$, $NR^9$, O or S;
$R^7$ and $R^8$ are independently
(1) a hydrogen atom,
(2) a cyano group,
(3) a $C_{1-6}$ alkyl group (e.g., methyl, ethyl) optionally substituted by 1 to 3 hydroxy groups, or
(4) a hydroxy group, or
$R^7$ and R in combination optionally form
(1) a $C_{3-10}$ cycloalkane (e.g., cyclohexane) optionally substituted by 1 to 3 substituents selected from
(i) an oxo group, and
(ii) a hydroxy group, or
(2) a non-aromatic heterocycle (preferably a 3- to 14-membered non-aromatic heterocycle, more preferably a 3- to 8-membered monocyclic non-aromatic heterocycle) (e.g., pyrrolidine, piperidine) optionally substituted by 1 to 3 $C_{7-16}$ aralkyl groups (e.g., benzyl); and
$R^9$ is
(1) a hydrogen atom, or
(2) a $C_{1-6}$ alkyl group (e.g., methyl, ethyl, propyl, isopropyl) optionally substituted by 1 to 3 substituents selected from
(i) a hydroxy group,
(ii) a $C_{1-6}$ alkoxy group (e.g., methoxy) optionally substituted by 1 to 3 $C_{6-14}$ aryl groups (e.g., phenyl), and
(iii) an amino group optionally mono- or di-substituted by $C_{1-6}$ alkyl group(s) (e.g., methyl),
(3) a $C_{2-6}$ alkenyl group (e.g., allyl), or
(4) a $C_{7-16}$ aralkyl group (e.g., benzyl) optionally substituted by 1 to 3 $C_{1-6}$ alkoxy groups (e.g., methoxy).

[Compound C-1]
Compound (I) wherein
$R^1$ is
(1) an aromatic heterocyclic group (preferably a 5- to 14-membered aromatic heterocyclic group, more preferably a 5- to 6-membered monocyclic aromatic heterocyclic group) (e.g., oxazolyl, pyridyl, pyrazolyl) optionally substituted by 1 to 3 substituents selected from
(i) a $C_{1-6}$ alkyl group (e.g., methyl) optionally substituted by 1 to 3 halogen atoms (e.g., a fluorine atom),
(ii) an aromatic heterocyclic group (preferably a 5- to 14-membered aromatic heterocyclic group, more preferably a 5- to 6-membered monocyclic aromatic heterocyclic group) (e.g., pyridyl, pyrazolyl) optionally substituted by 1 to 3 substituents selected from
(a) an amino group optionally mono- or di-substituted by $C_{1-6}$ alkyl group(s) (e.g., methyl, ethyl) optionally substituted by 1 to 3 substituents selected from
(I) a halogen atom (e.g., a fluorine atom), and
(II) a $C_{3-10}$ cycloalkyl group (e.g., cyclopropyl), and
(b) a $C_{1-6}$ alkyl group (e.g., methyl) optionally substituted by 1 to 3 amino groups, and
(iii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
(a) a $C_{1-6}$ alkyl group (e.g., methyl) optionally substituted by 1 to 3 amino groups, and
(b) an oxo group, or
(2) a $C_{6-14}$ aryl group (e.g., phenyl) optionally substituted by 1 to 3 $C_{1-6}$ alkyl groups (e.g., methyl);
$R^2$ is a $C_{1-6}$ alkyl group (e.g., methyl);
one of $R^3$ and $R^4$ is a hydrogen atom, and the other is a hydrogen atom or a $C_{1-6}$ alkyl group (e.g., methyl);
one of R and $R^6$ is a hydrogen atom, and the other is
(1) a hydrogen atom,
(2) a hydroxy group,
(3) a $C_{1-6}$ alkyl group (e.g., methyl) optionally substituted by 1 to 3 substituents selected from
(i) an amino group optionally mono- or di-substituted by $C_{1-6}$ alkyl group(s) (e.g., methyl), and
(ii) a hydroxy group, or
(4) an amino group optionally mono- or di-substituted by $C_{1-6}$ alkyl group(s) (e.g., methyl);
X is $CR^7R^9$, $NR^9$ or O;
$R^7$ and $R^8$ are independently
(1) a hydrogen atom, or
(2) a $C_{1-6}$ alkyl group (e.g., methyl); and
$R^9$ is
(1) a hydrogen atom, or
(2) a $C_{1-6}$ alkyl group (e.g., methyl, ethyl, propyl) optionally substituted by 1 to 3 hydroxy groups.

[Compound D-1]
Compound (I) wherein
$R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., ethyl) optionally substituted by 1 to 3 halogen atoms (e.g., a fluorine atom);
$R^2$ is a $C_{1-6}$ alkyl group (e.g., methyl);
$R^3$ and $R^4$ are both hydrogen atoms;
one of $R^5$ and $R^6$ is a hydrogen atom, and the other is
(1) a hydrogen atom,
(2) a hydroxy group,
(3) a $C_{1-6}$ alkyl group (e.g., methyl) optionally substituted by amino group(s) optionally mono- or di-substituted by $C_{1-6}$ alkyl group(s) (e.g., methyl), or
(4) an amino group optionally mono- or di-substituted by $C_{1-6}$ alkyl group(s) (e.g., methyl);
X is $CR^7R^8$; and
$R^7$ and $R^8$ are independently
(1) a hydrogen atom, or
(2) a $C_{1-6}$ alkyl group (e.g., methyl).

[Compound D-2]

Compound (I) wherein $R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 substituents selected from (1) a halogen atom (e.g., a fluorine atom), and (2) a $C_{3-10}$ cycloalkyl group (e.g., cyclopropyl);

$R^2$ is a $C_{1-6}$ alkyl group (e.g., methyl);

$R^3$ and $R^4$ are both hydrogen atoms;

one of $R^5$ and $R^6$ is a hydrogen atom, and the other is (1) a hydrogen atom, (2) a $C_{1-6}$ alkyl group (e.g., methyl) optionally substituted by amino group(s) optionally mono- or di-substituted by $C_{1-6}$ alkyl group(s) (e.g., methyl), or (3) an amino group optionally mono- or di-substituted by $C_{1-6}$ alkyl group(s) (e.g., methyl);

X is $CR^7R^8$ or $NR^9$;

$R^7$ and $R^8$ are independently (1) a hydrogen atom, or (2) a $C_{1-6}$ alkyl group (e.g., methyl); and $R^9$ is (1) a hydrogen atom, or (2) a $C_{1-6}$ alkyl group (e.g., methyl, ethyl) optionally substituted by 1 to 3 hydroxy groups.

[Compound E-1]

Compound (I) wherein $R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 halogen atoms (e.g., a fluorine atom);

$R^2$ is a $C_{1-6}$ alkyl group (e.g., methyl);

$R^3$ and $R^4$ are both hydrogen atoms;

$R^5$ and $R^6$ are both hydrogen atoms;

X is $CR^7R^8$ or $NR^9$;

$R^7$ and $R^8$ are independently (1) a hydrogen atom, or (2) a $C_{1-6}$ alkyl group (e.g., methyl); and $R^9$ is (1) a hydrogen atom, or (2) a $C_{1-6}$ alkyl group (e.g., methyl, ethyl) optionally substituted by 1 to 3 hydroxy groups.

[Compound F-1]

Compound (I) wherein $R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 halogen atoms (e.g., a fluorine atom);

$R^2$ is a $C_{1-6}$ alkyl group (e.g., methyl);

$R^3$ and $R^4$ are both hydrogen atoms;

$R^5$ and $R^6$ are both hydrogen atoms;

X is $NR^9$; and $R^9$ is (1) a hydrogen atom, or (2) a $C_{1-6}$ alkyl group (e.g., methyl, ethyl) optionally substituted by 1 to 3 hydroxy groups.

[Compound G-1]

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide or a salt thereof; or N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide or a salt thereof. [Compound H-1]

N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide or a salt thereof.

In one embodiment, the present disclosure provides a topical composition comprising a compound [Compound 2] of Formula (III) having the following structure:

Formula (III)

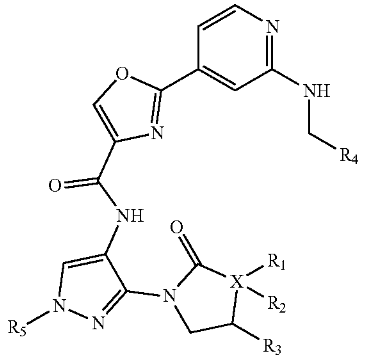

or a stereoisomer, solvates, tautomers, or pharmaceutically acceptable salts thereof, wherein:

$R_1$ and $R_2$ are independently selected from H, $C_{1-6}$ alkyl optionally substituted with hydroxyl;

$R_3$ is H, OH, —O—$C_{1-3}$ alkyl, or $CH_2NR_6R_7$;

$R_4$ is an optionally halogenated $C_{1-6}$ alkyl group (e.g., $CF_3$), an optionally halogenated $C_{3-10}$ cycloalkyl group, an optionally substituted non-aromatic heterocyclic group, an optionally substituted aromatic heterocyclic group, or an optionally substituted $C_{6-14}$ aryl group;

$R_5$ is $C_{1-6}$ alkyl, an optionally halo-substituted $C_{3-10}$ cycloalkyl group, or a non-aromatic heterocyclic group;

$R_6$ and $R_7$ are independently selected from H, $C_{1-6}$ alkyl and a $C_{3-10}$ cycloalkyl group;

X is N or C; and n is 0, 1 or 2, wherein when X is N, then $R_2$ is not present.

The disclosure further provides a compound of Formula III as follows:

2.1 Compound 2, wherein X is C and at least one of $R_1$ and $R_2$ is $C_{1-3}$ alkyl.

2.2 Compound 2, wherein X is C and at least one of $R_1$ and $R_2$ is H.
2.3 Compound 2, wherein X is C and $R_1$ is H and $R_2$ is $C_{1-3}$ alkyl.
2.4 Compound 2, wherein X is C and $R_1$ and $R_2$ are both $C_{1-3}$ alkyl.
2.5 Compound 2, wherein X is C and $R_1$ and $R_2$ are both H.
2.6 Compound 2, wherein X is N.
2.7 Compound 2.6, wherein $R_1$ is H.
2.8 Compound 2.6, wherein $R_1$ is $C_{1-3}$ alkyl.
2.9 Compound 2.6 or 2.8, wherein $R_1$ is methyl or propyl.
2.10 Compound 2.6, wherein $R_1$ is $C_{1-6}$ alkyl substituted with hydroxyl.
2.11 Compound 2.6 or 2.10, wherein $R_1$ is hydroxyethyl or hydroxypropyl (e.g., 2-hydroxyethyl or 2-hydroxypropyl).
2.12 Any of compounds 2 or 2.1-2.11, wherein $R_3$ is H.
2.13 Any of compounds 2 or 2.1-2.11, wherein $R_3$ is OH.
2.14 Any of compounds 2 or 2.1-2.11, wherein $R_3$ is $CH_2NR_6R_7$ and at least one of $R_6$ and $R_7$ are H.
2.15 Any of compounds 2 or 2.1-2.11, wherein $R_3$ is $CH_2NR^6R_7$ and at least one of $R_6$ and $R_7$ are $C_{1-6}$ alkyl.
2.16 Any of compounds 2 or 2.1-2.11, wherein $R_3$ is $CH_2NR^6R_7$ and at least one of $R_6$ and $R_7$ are a $C_{3-10}$ cycloalkyl group (e.g., cyclopropyl).
2.17 Any of compounds 2 or 2.1-2.11, wherein $R_3$ is $CH_2NR^6R_7$ and $R_6$ is H and $R_7$ is $C_{1-6}$ alkyl (e.g., methyl).
2.18 Any of compounds 2 or 2.1-2.11, wherein $R_3$ is $CH_2NR^6R_7$ and both $R_6$ and $R_7$ are $C_{1-6}$ alkyl (e.g., methyl).
2.19 Any of compounds 2 or 2.1-2.18, wherein $R_4$ is a halogenated $C_{1-6}$ alkyl group.
2.20 Any of compounds 2 or 2.1-2.19, wherein $R_4$ is $CF_3$.
2.21 Any of compounds 2 or 2.1-2.18, wherein $R_4$ is an optionally halogenated $C_{3-10}$ cycloalkyl group (e.g., cyclopropyl).
2.22 Any of compounds 2 or 2.1-2.21, wherein $R_5$ is $C_{1-6}$ alkyl.
2.23 Any of the preceding compounds, wherein $R_5$ is methyl.
2.24 Any of compounds 2 or 2.1-2.21, wherein $R_5$ is a non-aromatic heterocyclic group.
2.25 Any of compounds 2 or 2.1-2.21 or 2.24, wherein $R_5$ is a 3- to 14-membered non-aromatic heterocyclic group.
2.26 Any of compounds 2 or 2.1-2.21 or 2.24-2.25, wherein $R_5$ is a 4-membered non-aromatic heterocyclic group.
2.27 Any of compounds 2 or 2.1-2.21 or 2.24-2.26, wherein $R_5$ is oxetanyl.
2.28 Any of the preceding compounds, wherein the compound of Formula III has one of the following structures:

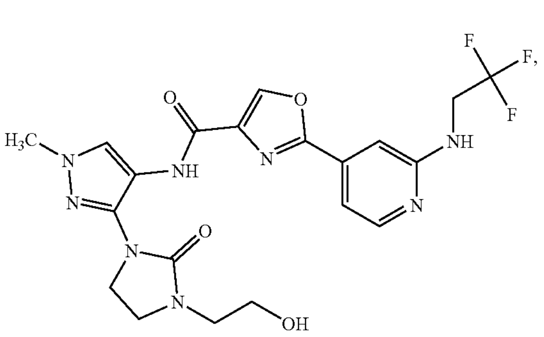

-continued

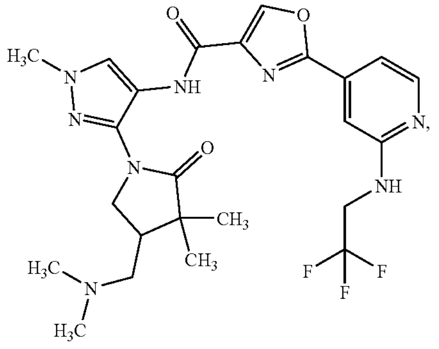

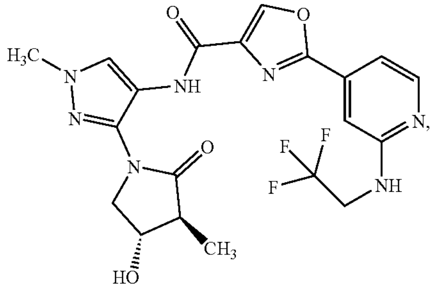

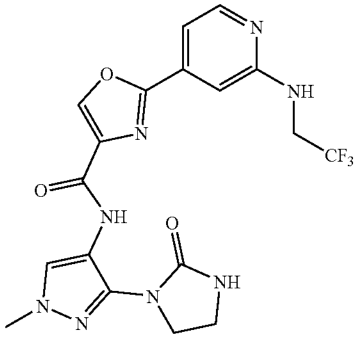

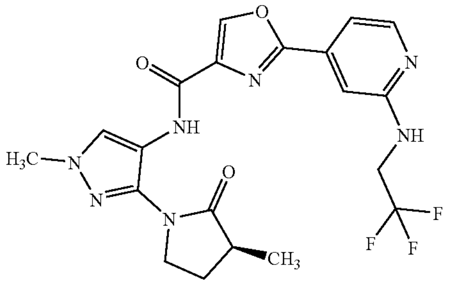

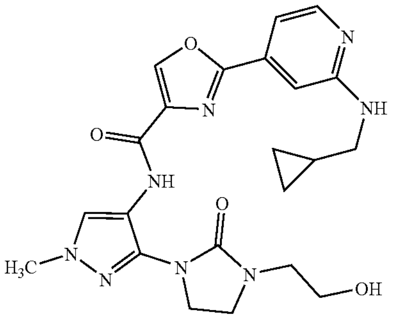

-continued

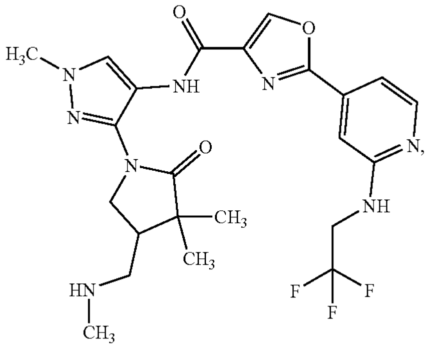

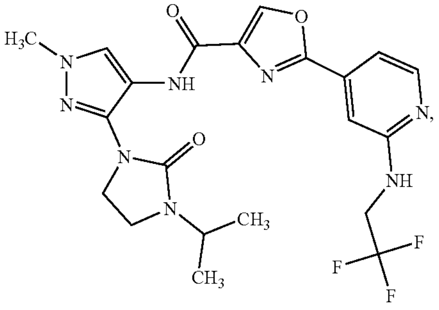

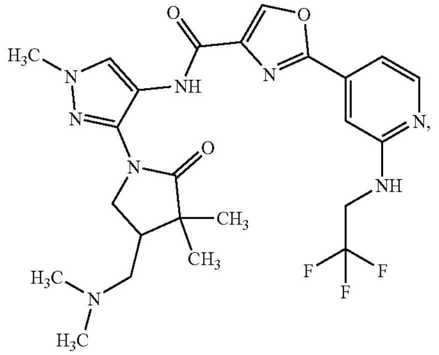

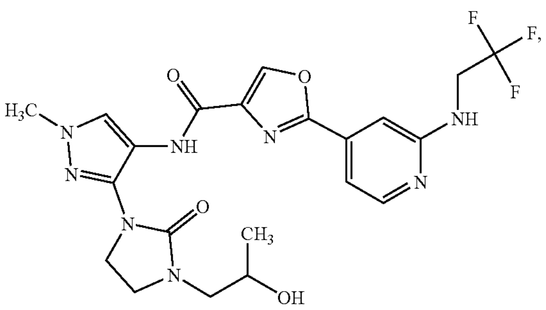

-continued

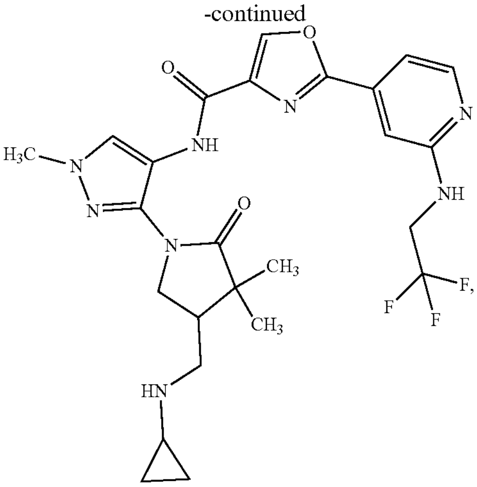

or

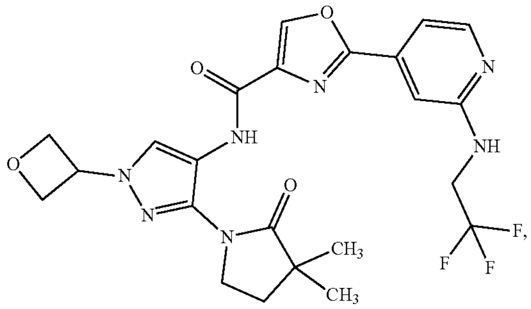

or a stereoisomer, solvates, tautomers, or pharmaceutically acceptable salts thereof.

2.29 Any of the preceding compounds, wherein the compound of Formula III is selected from the following:

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, 2-(2-((2,2-difluoroethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide, N-(3-((3S,4S)-4-hydroxy-3-methyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide, N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide, 2-(2-((cyclopropylmethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide, N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3-isopropyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3-(2-hydroxypropyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((cyclopropylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, and N-(3-(3,3-dimethyl-2-oxopyrrolidin-1-yl)-1-(oxetan-3-yl)-1H-pyrazol-4-yl)-2-(2-((2,2,2-trifluoroethyl)amino)pyridin-4-yl)-1,3-oxazole-4-carboxamide, or a stereoisomer, solvates, tautomers, or pharmaceutically acceptable salts thereof 2.30 Compound 2.28, wherein the compounds of Formula III has the following structure:

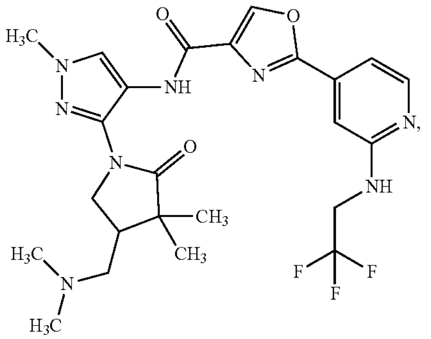 [SMILES: CN(C)CC1CN(c2nn(C)cc2NC(=O)c2coc(-c3ccnc(NCC(F)(F)F)c3)n2)C(=O)C1(C)C]

or a stereoisomer, solvates, tautomers, or pharmaceutically acceptable salts thereof.

2.31 Compound 2.28, wherein the compounds of Formula III has the following structure:

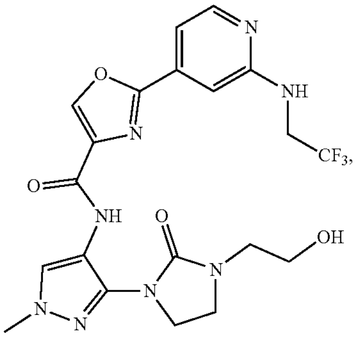 [SMILES: Cn1cc(NC(=O)c2coc(-c3ccnc(NCC(F)(F)F)c3)n2)c(N2CCN(CCO)C2=O)n1]

or a stereoisomer, solvates, tautomers, or pharmaceutically acceptable salts thereof.

2.32 Compound 2.28, wherein the compounds of Formula III has the following structure:

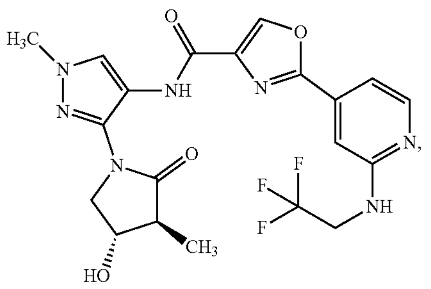 [SMILES: C[C@@H]1C(=O)N(c2nn(C)cc2NC(=O)c2coc(-c3ccnc(NCC(F)(F)F)c3)n2)C[C@H]1O]

or a stereoisomer, solvates, tautomers, or pharmaceutically acceptable salts thereof.

2.33 Compound 2.28, wherein the compounds of Formula III has the following structure:

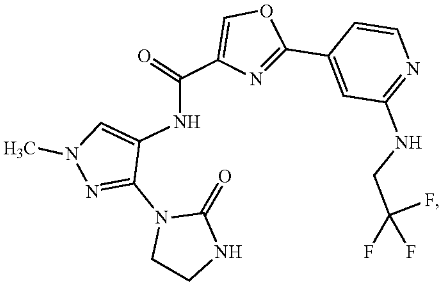 [SMILES: Cn1cc(NC(=O)c2coc(-c3ccnc(NCC(F)(F)F)c3)n2)c(N2CCNC2=O)n1]

or a stereoisomer, solvates, tautomers, or pharmaceutically acceptable salts thereof.

2.34 Compound 2.28, wherein the compounds of Formula III has the following structure:

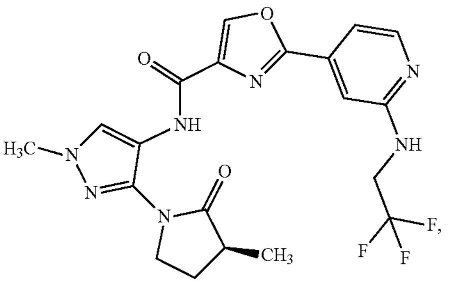 [SMILES: C[C@H]1CCN(c2nn(C)cc2NC(=O)c2coc(-c3ccnc(NCC(F)(F)F)c3)n2)C1=O]

or a stereoisomer, solvates, tautomers, or pharmaceutically acceptable salts thereof.

2.35 Compound 2.28, wherein the compounds of Formula III has the following structure:

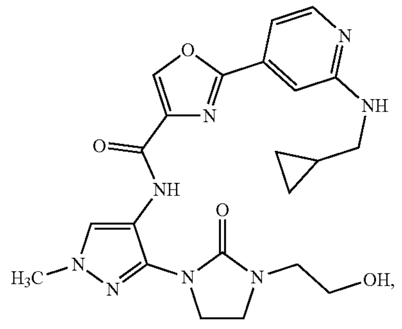 [SMILES: Cn1cc(NC(=O)c2coc(-c3ccnc(NCC4CC4)c3)n2)c(N2CCN(CCO)C2=O)n1]

or a stereoisomer, solvates, tautomers, or pharmaceutically acceptable salts thereof.

2.36 Compound 2.28, wherein the compounds of Formula III has the following structure:

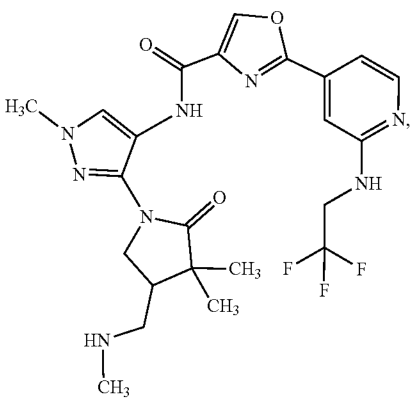 [SMILES: CNCC1CN(c2nn(C)cc2NC(=O)c2coc(-c3ccnc(NCC(F)(F)F)c3)n2)C(=O)C1(C)C]

or a stereoisomer, solvates, tautomers, or pharmaceutically acceptable salts thereof.

2.37 Compound 2.28, wherein the compounds of Formula III has the following structure:

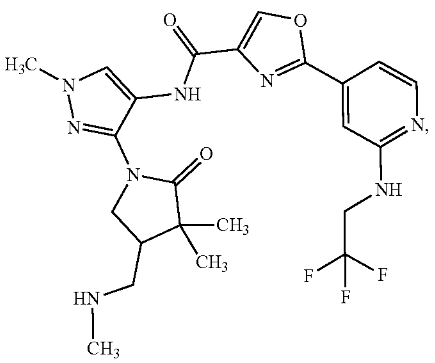 [SMILES: CNCC1CN(c2nn(C)cc2NC(=O)c2coc(-c3ccnc(NCC(F)(F)F)c3)n2)C(=O)C1(C)C]

or a stereoisomer, solvates, tautomers, or pharmaceutically acceptable salts thereof.

2.38 Compound 2.28, wherein the compounds of Formula III has the following structure:

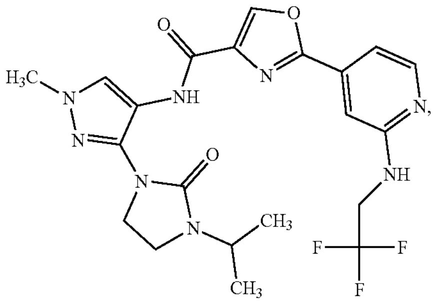 [SMILES: CC(C)N1CCN(c2nn(C)cc2NC(=O)c2coc(-c3ccnc(NCC(F)(F)F)c3)n2)C1=O]

or a stereoisomer, solvates, tautomers, or pharmaceutically acceptable salts thereof.

2.39 Compound 2.28, wherein the compounds of Formula III has the following structure:

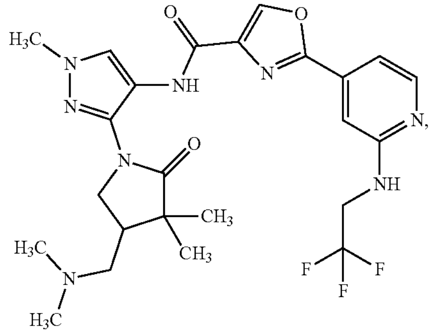 [SMILES: CN(C)CC1CN(c2nn(C)cc2NC(=O)c2coc(-c3ccnc(NCC(F)(F)F)c3)n2)C(=O)C1(C)C]

or a stereoisomer, solvates, tautomers, or pharmaceutically acceptable salts thereof.

2.40 Compound 2.28, wherein the compounds of Formula III has the following structure:

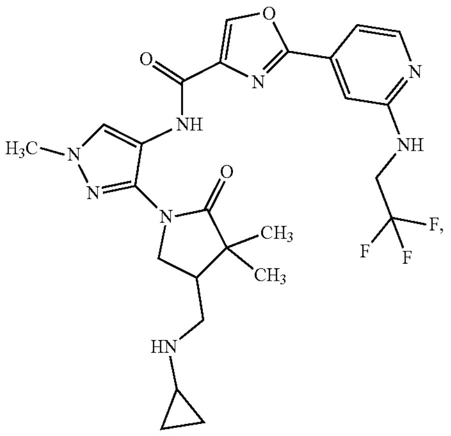 [SMILES: Cn1cc(NC(=O)c2coc(-c3ccnc(NCC(F)(F)F)c3)n2)c(N2CC(CNC3CC3)C(C)(C)C2=O)n1]

or a stereoisomer, solvates, tautomers, or pharmaceutically acceptable salts thereof.

2.41 Compound 2.28, wherein the compounds of Formula III has the following structure:

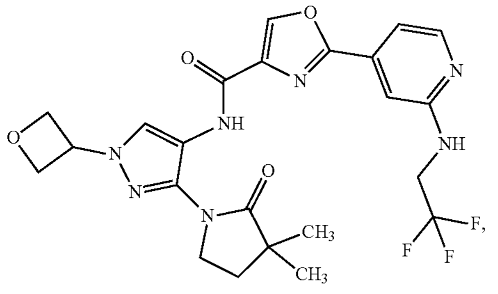 [SMILES: CC1(C)CCN(c2nn(C3COC3)cc2NC(=O)c2coc(-c3ccnc(NCC(F)(F)F)c3)n2)C1=O]

or a stereoisomer, solvates, tautomers, or pharmaceutically acceptable salts thereof.

2.42 Any of the preceding compounds, wherein the compound of Formula III has one of the following structures:

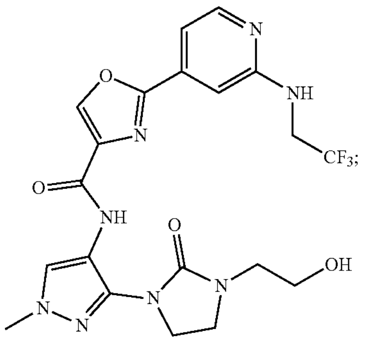

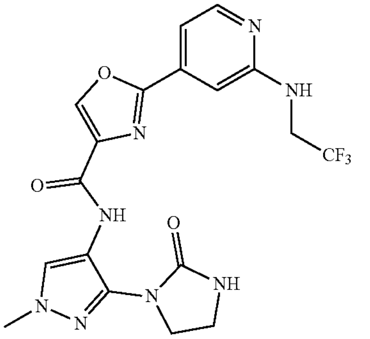

or

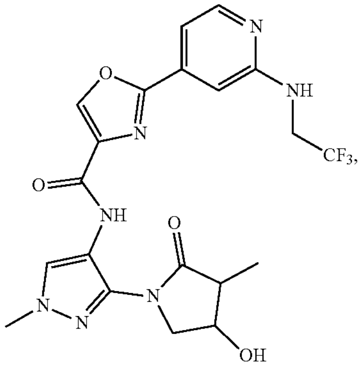

or a stereoisomer, solvates, tautomers, or pharmaceutically acceptable salts thereof.

2.43 Compound 2.42, wherein the compound of Formula III has the following structure:

Formula (Ia)

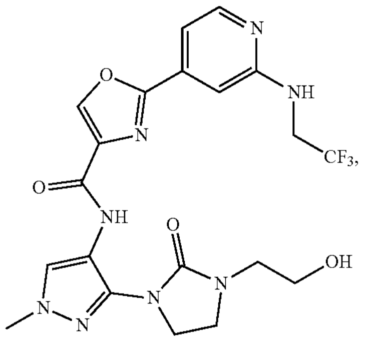

or is a stereoisomer, solvate, tautomer, or a pharmaceutically acceptable salt thereof.

2.44 Compound 2.42, wherein the compound of Formula III has the following structure:

Formula (Ib)

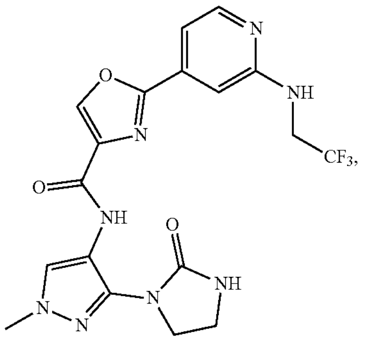

or is a stereoisomer, solvate, tautomer, or a pharmaceutically acceptable salt thereof.

2.45 Compound 2.42, wherein the compound of Formula III has the following structure:

Formula (Ic)

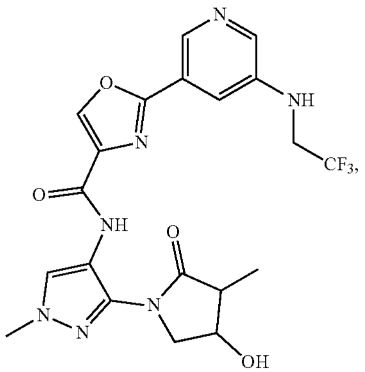

or is a stereoisomer, solvate, tautomer, or a pharmaceutically acceptable salt thereof.

In a further aspect, the present disclosure further provides a dermatological composition [Composition 1] comprising: a pharmaceutically effective amount of an IRAK4 inhibitor of the present disclosure, i.e., a compound of Formula I, II (e.g., Compound 1, et seq.), or III (e.g., Compound 2, et seq.);

a solvent system comprising one or more solvents; and an antioxidant.

The present disclosure further provides compositions as follows:

1.1 Composition 1, wherein the IRAK4 inhibitor is selected from the following:

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, 2-(2-((2,2-difluoroethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide, N-(3-((3S,4S)-4-hydroxy-3-methyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide, N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide, 2-(2-((cyclopropylmethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide, N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3-isopropyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3-(2-hydroxypropyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((cyclopropylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, and N-(3-(3,3-dimethyl-2-oxopyrrolidin-1-yl)-1-(oxetan-3-yl)-1H-pyrazol-4-yl)-2-(2-((2,2,2-trifluoroethyl)amino)pyridin-4-yl)-1,3-oxazole-4-carboxamide, or a stereoisomer, tautomers, or pharmaceutically acceptable salts thereof;

1.2 Any of the preceding compositions, wherein the solvent system comprises one or more solvents selected from a polyether, a polyethylene glycol (e.g., PEG 400), a polyether alcohol (e.g., diethylene glycol monoethyl ether; Transcutol® P), an ether, and an alcohol;

1.3 Any of the preceding compositions, wherein the solvent system comprises one or more solvents selected from a polyethylene glycol having a molecular weight about 300 to about 600, a polyether alcohol having a molecular weight less than 200 daltons, (e.g., diethylene glycol monoethyl ether; Transcutol® P), an alcohol (e.g., benzyl alcohol or phenoxyethanol), and an ether (e.g., dimethyl isosorbide);

1.4 Any of the preceding compositions, wherein the solvent system comprises a polyethylene glycol (e.g., PEG 400) and a polyether alcohol;

1.5 Any of the preceding compositions, wherein the solvent system comprises PEG 400 and diethylene glycol monoethyl ether (Transcutol® P);

1.6 Composition 1.5, wherein the solvent system further comprises one or more preservatives;

1.7 Composition 1.6, wherein the preservative is present in an amount of from about 0.01% to about 20% by weight of the composition, or about 0.1% to about 10% by weight of the composition; or about 0.5% to about 5% by weight of the composition, or about 1% to about 3% by weight of the composition, or about 2% by weight of the composition;

1.8 Composition 1.6, wherein the preservative is an alcohol, for example selected from benzyl alcohol and phenoxyethanol;

1.9 Any of the preceding compositions, wherein the solvent system is present in an amount of from about 50% to about 90% by weight of the composition, or about 75% to about 90% by weight of the composition; or about 80% to about 90% by weight of the composition, or about 85% to about 90% by weight of the composition, or about 55% to about 65% by weight of the composition; or about 55% to about 60% by weight of the composition;

1.10 Any of the preceding compositions, wherein the solvent system is present in an amount of from about 80% to about 90% by weight of the composition, or about 50% to about 65% by weight of the composition; or about 60%, or about 65% by weight of the composition;

1.11 Any preceding composition, wherein the solvent system comprises PEG 400 in an amount of from about 20% to about 70% by weight of the composition, or about 35% to about 70% by weight of the composition; or about 35% to about 50% by weight of the composition, or about 40% to about 45% by weight of the composition, or about 55% to about 65% by weight of the composition; or about 40%, about 45%, about 50%, about 55%, or about 60% by weight of the composition;

1.12 Any preceding composition, wherein the solvent system comprises diethylene glycol monoethyl ether (Transcutol® P) in an amount of from about 10% to about 45% by weight of the composition, or about 10% to about 20% by weight of the composition; or about 20% to about 30% by weight of the composition, or about 10%, about 15%, about 20%, about 25%, about 30%, about 35%, about 40% or about 45% by weight of the composition;

1.13 Any of the preceding compositions, wherein the antioxidant is selected from one or more of butylated hydroxytoluene (BHT), sodium metabisulfite, ascorbic acid, propyl gallate, and/or alpha tocopherol (Vitamin E);

1.14 Any of the preceding compositions, wherein the antioxidant is present in an amount of about 0.001 wt. % to about 1 wt. %, based on the total weight of the composition.

1.15 Any of the preceding compositions, wherein the antioxidant comprises or consists of butylated hydroxytoluene in an amount of about 0.01 wt. % to about 1 wt. %, e.g., about 0.2 wt. %, or about 0.1 wt. %, based on the total weight of the composition;

1.16 Any of the preceding compositions, wherein the composition further comprises a nonsolvent;

1.17 Composition 1.16, wherein the nonsolvent is water, a silicone oil (e.g., dimethicone 350), or a mixture thereof;

1.18 Composition 1.17, wherein the water is present in an amount of from about 5% to about 30% by weight of the composition, or about 5% to about 15% by weight of the composition; or about 15% to about 25% by weight of the composition, or about 10%, or about 15%, or about 20% by weight of the composition;

1.19 Composition 1.17, wherein the silicone oil is dimethicone 350, and is present in an amount of from about 0.01% to about 2% by weight of the composition, or about 0.1% to about 1.5% by weight of the composition; or about 0.5% to about 1% by weight of the composition, or about 0.75% by weight of the composition;

1.20 Any of the preceding compositions, wherein the composition further comprises a gelling agent.

1.21 Any of the preceding compositions, wherein the composition further comprises a gelling agent;

1.22 Composition 1.20 or 1.21, wherein the gelling agent is a polymer;

1.23 Composition 1.20 or 1.21, wherein the gelling agent comprises one or more of a crosslinked polyacrylic acid and a non-ionic cellulose ether;

1.24 Composition 1.20 or 1.21, wherein the gelling agent comprises one or more of a Carbopol polymer and a hydroxypropylcellulose;

1.25 Composition 1.20 or 1.21, wherein the gelling agent comprises one or more of Carbopol 980 NF and HPC HF;

1.26 Any of the preceding compositions 1.20-1.25, wherein the gelling agent is present in an amount of from 0.01% to about 5% by weight of the composition, or about 0.1% to about 3% by weight of the composition; or about 0.5% to about 2% by weight of the composition, or about 0.75% to about 1.25% by weight of the composition or about 1% by weight of the composition;

1.27 Any of the preceding compositions, further comprising a skin conditioner;

1.28 Composition 1.27, wherein the skin conditioner is selected from diisopropyl adipate and a silicone oil;

1.29 Composition 1.28 wherein the silicone oil is dimethicone 350;

1.30 Any of the preceding compositions 1.27-1.29, wherein the skin conditioner is present in an amount of from 0.1% to about 15% by weight of the composition, or about 0.1% to about 5% by weight of the composition; or about 0.1% to about 2% by weight of the composition, or about 5% to about 15% by weight of the composition, or about 1% by weight of the composition, or about 10% by weight of the composition;

1.31 Any of the preceding compositions, further comprising an emollient;

1.32 Composition 1.30, wherein the emollient is a triglyceride, e.g., a medium chain triglyceride;

1.33 Composition 1.30 or 1.31, the emollient is Crodamol GTCC;

1.34 Any of the preceding compositions 1.31-1.33, wherein the emollient is present in an amount of from 0.1% to about 15% by weight of the composition, or about 0.1% to about 5% by weight of the composition; or about 0.1% to about 2% by weight of the composition, or about 5% to about 15% by weight of the composition, or about 1% by weight of the composition, or about 10% by weight of the composition;

1.35 Any of the preceding compositions, further comprising a viscosity enhancing agent;

1.36 Composition 1.35, wherein the viscosity enhancing agent is selected from one or more $C_{14}$-$C_{30}$ fatty alcohols, a cellulose, an acrylate polymer or crosspolymers, or a carbomer;

1.37 Composition 1.35, wherein the viscosity enhancing agent is selected from hydroxypropyl cellulose, hydroxymethyl cellulose, hydroxypropylmethyl cellulose (e.g., Benecel E4M), cetostearyl alcohol, poloxamer (Pluronic PF127), carbomers (e.g., carbomer 980, carbomer 1342 and carbomer 940), more specifically hydroxypropyl cellulose (e.g., hydroxypropyl cellulose having a molecular weight between 850,000-1,150,000 daltons Klucel® EF, GF, MF and/or HF), Pluronic PF127, carbomer 980 and/or carbomer 1342 (Pemulen® TR-1, TR-2 and/or Carbopol® ETD 2020).

1.38 Composition 1.35, wherein the viscosity enhancing agent is cetostearyl alcohol;

1.39 Any of the preceding compositions 1.35-1.38, wherein the viscosity enhancing agent is present in an amount of from 0.1% to about 15% by weight of the composition, or about 1% to about 10% by weight of the composition; or about 3% to about 7% by weight of the composition, or about 5% by weight of the composition, or about 1% to about 5% by weight of the composition, or about 1% by weight of the composition, or about 2% by weight of the composition, or about 3% by weight of the composition, or about 4% by weight of the composition, or about 5% by weight of the composition;

1.40 Any of the preceding compositions, further comprising a surfactant;

1.41 Composition 1.40, wherein the surfactant is selected from one or more of polyoxyethylene fatty ethers; nonoxynols, polysorbates, polyoxylene alcohols, polyoxylene fatty acid esters, sodium lauryl sulfate, and sorbitan monostearate;

1.42 Composition 1.40 or 1.41, wherein the surfactant is selected from Brij S2 and Brij S 20;

1.43 Any of the preceding compositions 1.40-1.42, wherein the surfactant is present in an amount of from 0.1% to about 15% by weight of the composition, or about 1% to about 5% by weight of the composition; or about 1% to about 4% by weight of the composition; or about 1%, about 2%, about 3%, about 4%, about 5%, about 7%, or about 10% by weight of the composition;

1.44 Any of the preceding compositions, further comprising an additional excipient;

1.45 Composition 1.44, wherein the additional excipient is selected from alcohols (e.g., $C_{1-20}$ alkanols (e.g., oleyl alcohol, cetyl alcohol, octyldodecanol, cetostearyl alcohol, benzyl alcohol), a saturated or unsaturated fatty acid ester, a saturated or unsaturated fatty acid ester, a polyoxythylene fatty ether, a polyoxylene fatty acid esters, diethylene glycol monoethyl ether, 1,3-dimethyl-2-imidazolidinone and/or dimethyl isosorbide;

1.46 Composition 1.44, wherein the additional excipient is selected from oleyl alcohol, cetyl alcohol, octyldodecanol, cetostearyl alcohol, mineral oil, benzyl alcohol, isopropyl myristate, diisopropyl adipate, ethylhexyl hydroxystearate, Steareth-2 (Brij S2), Steareth-20 (Brij S20), glyceryl stearate, stearic acid, magnesium stearate, diethylene glycol monoethyl ether, 1,3-dimethyl-2-imidazolidinone and/or dimethyl isosorbide;

1.47 Composition 1.44, wherein the additional excipient is selected from one or more of propylene glycol, oleyl alcohol, diisopropyl adipate and isopropyl myristate;

1.48 Compositions 1.44, wherein the additional excipient comprises propylene glycol;

1.49 Any of the preceding compositions 1.44-1.48, wherein the additional excipient is present in an amount of from 0.1% to about 20% by weight of the composition, or about 1% to about 15% by weight of the composition; or about 5% to about 15% by weight of the composition, or about 10% by weight of the composition;

1.50 Any of the preceding compositions, wherein the composition is in the form of a cream, a lotion, a foam, an aqueous gel, a non-aqueous gel, a spray or an ointment (e.g., a polyethylene glycol-based ointment).

1.51 Any preceding composition, wherein the composition is an aqueous gel;

1.52 Any preceding composition, wherein the composition is a non-aqueous gel;

1.53 Any preceding composition, wherein the composition is a cream;

1.54 Any preceding composition, wherein the composition is an ointment (e.g., a polyethylene glycol-based ointment);

1.55 Any of the preceding compositions, wherein the composition has an apparent pH of about 3:5 to about 7.5, about 4 to about 7, about 4.5 to about 6.5 or about 5 to about 6.5, or about 5.5 to about 6.5, or about 6;

1.56 Any of the preceding compositions, wherein the composition is applied to a patient's skin three times daily, twice daily, once daily, every other day, weekly, or monthly;

1.57 Any of the preceding compositions, wherein the composition is applied to a patient's skin twice daily;

1.58 Any of the preceding compositions, wherein the composition is applied to a patient's skin three times or more daily;

1.59 Any of the preceding compositions, wherein the composition is administered to a patient suffering from a dermatological condition characterized by inflammation.

1.60 Composition 1.59, wherein the dermatological condition is selected from rosacea, psoriasis, atopic dermatitis, hidradenitis suppurativa, seborrheic dermatitis, contact dermatitis, urticaria, dermatitis herpetiformis, nummular dermatitis, lichen planus, *Pityriasis rosea*, cutaneous lupus, acne, cancers of the skin (e.g. cutaneous T-cell lymphoma), and miliaria;

1.61 Composition 1.59, wherein the dermatological disorder is rosacea;

1.62 Composition 1.59, wherein the rosacea is papulopustular rosacea;

1.63 Composition 1.59, wherein the dermatological disorder is psoriasis;

1.64 Composition 1.59, wherein the dermatological disorder is atopic dermatitis;

1.65 Composition 1.59, wherein the dermatological disorder is hidradenitis suppurativa;

1.66 Composition 1.59, wherein the dermatological disorder is psoriasis.

1.67 Any of the preceding compositions, wherein the skin is mammalian skin (e.g., human skin).

1.68 Any of the preceding compositions, wherein the topical composition is an aqueous gel; the solvent system comprises PEG 400 and Transcutol® P wherein the w/w ratio of PEG 400/Transcutol® P is from about 0.7 to about 1.1, for example from about 0.8 to about 1.0, for example about 0.9;

1.69 Any of the preceding compositions, wherein the topical composition is a non-aqueous gel; the solvent system comprises PEG 400 and Transcutol® P wherein the w/w ratio of PEG 400/Transcutol® P is from about 2.2 to about 2.6, for example from about 2.3 to about 2.5, for example about 2.4;

1.70 Any of the preceding compositions, wherein the topical composition is a cream;

the solvent system comprises PEG 400 and Transcutol® P wherein the w/w ratio of PEG 400/Transcutol® P is from about 2.6 to about 3.2, for example from about 2.7 to about 3.1, for example about 2.9;

1.71 Any of the preceding compositions, wherein the topical composition is an ointment; the solvent system comprises PEG 400 and Transcutol® P wherein the w/w ratio of PEG 400/Transcutol® P is from about 3.5 to about 4.5, for example from about 3.8 to about 4.2, for example about 4;

The IRAK4 inhibitors described herein may be prepared according to the methods disclosed in, for example, U.S. Pat. Nos. 9,890,145 and 9,321,757, which patents are incorporated by reference in their entireties.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy, group" include a $C_{1-6}$ alkoxy group optionally having 1 to 7, preferably 1 to 5 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5 halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-40}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),

(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, pi-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, ietrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include-quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_3$-10 cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include $—CH_2—$, $—(CH_2)_2—$, $—(CH_2)_3—$, $—(CH_2)_4—$, $—(CH_2)_5—$, $—(CH_2)_6—$, $—CH(CH_3)—$, $—C(CH_3)_2—$, $—CH(C_2H_5)—$, $—CH(C_3H_7)—$, $—CH(CH(CH_3)_2)—$, $—(CH(CH_3))_2—$, $—CH_2—CH(CH_3)—$, $—CH(CH_3)—CH_2—$, $—CH_2—CH_2—C(CH_3)_2—$, $—C(CH_3)_2—CH_2—CH_2—$, $—CH_2—CH_2—CH_2—C(CH_3)_2—$ and $—C(CH_3)_2—CH_2—CH_2—CH_2—$.

In the present specification, examples of the "$C_{2-6}$ alkenylene group" include $—CH{=}CH—$, $—CH_2—CH{=}CH—$, $—CH{=}CH—CH_2—$, $—C(CH_3)_2—CH{=}CH—$, $—CH{=}CH—C(CH_3)_2—$, $—CH_2—CH{=}CH—CH_2—$, $—CH_2—CH_2—CH{=}CH—$, $—CH{=}CH—CH_2—CH_2—$, $—CH{=}CH—CH{=}CH—$, $—CH{=}CH—CH_2—CH_2—CH_2—$ and $—CH_2—CH_2—CH_2—CH{=}CH—$.

In the present specification, examples of the "$C_{2-6}$ alkynylene group" include $—C{\equiv}C—$, $—CH_2—C{\equiv}C—$, $—C{\equiv}C—CH_2—$, $—C(CH_3)_2—C{\equiv}C—$, $—C{\equiv}C—C(CH_3)_2—$, $—CH_2—C{\equiv}C—CH_2—$, $—CH_2—CH_2—C{\equiv}C—$, $—C{\equiv}C—CH_2—CH_2—$, $—C{\equiv}C—C{\equiv}C—$, $—C{\equiv}C—CH_2—CH_2—CH_2—$ and $—CH_2—CH_2—CH_2—C{\equiv}C—$.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-44}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In one embodiment, preferable examples of the "non-aromatic heterocyclic group" include a 7- to 14-membered spiro heterocyclic group such as triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl) and the like, in addition to the above-mentioned "3- to 8-membered monocyclic non-aromatic heterocyclic group" and "9- to 14-membered fused polycyclic (preferably bi- or tri-cyclic) non-aromatic heterocyclic group".

As used herein, "topical composition" refers to a formulation of a compound of the invention and a medium generally accepted in the art for the delivery of the biologically active compound to mammalian skin, e.g., human skin. Such a medium includes all dermatologically acceptable carriers, diluents or excipients therefor.

"Stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

"Solvate" refers to a form of a compound complexed by solvent molecules.

"Tautomers" refers to two molecules that are structural isomers that readily interconvert.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

The chemical naming protocol and structure diagrams used herein are a modified form of the I.U.P.A.C. nomenclature system, using the ChemDraw Version 10 software naming program (CambridgeSoft). In chemical structure diagrams, all bonds are identified, except for some carbon atoms, which are assumed to be bonded to sufficient hydrogen atoms to complete the valency.

"Dermatologically acceptable excipient" includes without limitation any adjuvant, carrier, vehicle, excipient, glidant, sweetening agent, diluent, preservative, dye/colorant, flavor enhancer, surfactant, wetting agent, dispersing agent, suspending agent, stabilizer, isotonic agent, solvent, or emulsifier, including those approved by the United States Food and Drug Administration as being acceptable for dermatological use on humans or domestic animals, or which are known, or are suitable for use in dermatological compositions.

"Optional" or "optionally" means that the subsequently described event of circumstances may or may not occur, and that the description includes instances where said event or circumstance occurs and instances in which it does not. When a functional group is described as "optionally substituted," and in turn, substituents on the functional group are also "optionally substituted" and so on, for the purposes of this invention, such iterations are limited to five, preferably such iterations are limited to two.

Treatment of Dermatological Disorders

In one embodiment, the present disclosure provides for a method [Method 1] for treating a dermatological disorder, the method comprising topically administering to a subject in need thereof a topical composition according to any of Compositions 1 or 1.1-1.71 above.

The present disclosure provides additional embodiments of Method 1 as follows:

1.1 Method 1, wherein the IRAK4 inhibitor is a dual IRAK4/TrkA inhibitor.

1.2 Any of the preceding methods, wherein the IRAK4 inhibitor is a compound according to Compound 1, et seq. or Compound 2, et seq.

1.3 Any of the preceding methods, wherein the dermatological disorder is an inflammatory dermatological disorder.

1.4 The preceding method, wherein the inflammatory dermatological disorder is rosacea, psoriasis, atopic dermatitis, hidradenitis suppurativa, seborrheic dermatitis, contact dermatitis, urticaria, dermatitis herpetiformis, nummular dermatitis, lichen planus, *Pityriasis rosea*, cutaneous lupus, acne, cancers of the skin (e.g. cutaneous T-cell lymphoma), or miliaria.

1.5 Any of Method 1 or 1.3-1.4, wherein the inflammatory dermatological disorder is rosacea.

1.6 The preceding method, wherein the rosacea is papulopustular rosacea.

1.7 Method 1 or 1.1-1.4, wherein the inflammatory dermatological disorder is psoriasis.

1.8 Method 1 or 1.1-1.4, wherein the inflammatory dermatological disorder is atopic dermatitis.

1.9 Method 1 or 1.1-1.4, wherein inflammatory dermatological disorder is hidradenitis suppurativa.

1.10 Method 1 or 1.1-1.4, wherein inflammatory dermatological disorder is cutaneous lupus.

1.11 Method 1 or 1.1-1.4, wherein inflammatory dermatological disorder is acne.

1.12 Method 1 or 1.1-1.4, wherein inflammatory dermatological disorder is a cancer of the skin (e.g., cutaneous T-cell lymphoma).

1.13 Any of the preceding methods, the subject is a human.

Another embodiment provides a method [Method 2] for reducing inflammation in mammalian skin, the method comprising topically administering to the mammalian skin an effective amount of a topical composition according to any of Compositions 1 or 1.1-1.71 above to a subject in need thereof.

The present disclosure provides additional embodiments of Method 2 as follows:

2.1 Method 2, wherein the IRAK4 inhibitor is a dual IRAK4/TrkA inhibitor.

2.2 Any of the preceding methods, wherein the IRAK4 inhibitor is a compound according to Compound 1, et seq. or Compound 2, et seq.

2.3 Any of the preceding methods, wherein the subject is suffering from a dermatological disorder.

2.4 Method 2.3, wherein the dermatological disorder is an inflammatory dermatological disorder.

2.5 The preceding method, wherein the inflammatory dermatological disorder is rosacea, psoriasis, atopic dermatitis, hidradenitis suppurativa, seborrheic dermatitis, contact dermatitis, urticaria, dermatitis herpetiformis, nummular dermatitis, lichen planus, *Pityriasis rosea*, cutaneous lupus, acne, cancers of the skin (e.g. cutaneous T-cell lymphoma), or miliaria.

2.6 Any of Methods 2.3-2.5, wherein the inflammatory dermatological disorder is rosacea.

2.7 The preceding method, wherein the rosacea is papulopustular rosacea.

2.8 Any of Methods 2.3-2.5, wherein the inflammatory dermatological disorder is psoriasis.

2.9 Any of Methods 2.3-2.5, wherein the inflammatory dermatological disorder is atopic dermatitis.

2.10 Any of Methods 2.3-2.5, wherein inflammatory dermatological disorder is hidradenitis suppurativa.

2.11 Any of Methods 2.3-2.5, wherein inflammatory dermatological disorder is cutaneous lupus.

2.12 Any of Methods 2.3-2.5, wherein inflammatory dermatological disorder is acne.

2.13 Any of Methods 2.3-2.5, wherein inflammatory dermatological disorder is a cancer of the skin (e.g., cutaneous T-cell lymphoma).

2.14 Any of the preceding methods, the subject is a human.

2.15 Any of the preceding methods, wherein the mammalian skin is human skin.

A further embodiment provides a method [Method 3] of reducing inflammation and vascular dysfunction in mammalian skin, the method comprising topically administering to the mammalian skin a therapeutically effective amount of a topical composition a topical composition according to any of Compositions 1 or 1.1-1.71 above to a subject in need thereof.

The present disclosure provides additional embodiments of Method 3 as follows:

3.1 Method 3, wherein the IRAK4 inhibitor is a dual IRAK4/TrkA inhibitor.

3.2 Any of the preceding methods, wherein the IRAK4 inhibitor is a compound according to Compound 1, et seq. or Compound 2, et seq.

3.3 Any of the preceding methods, wherein the subject is suffering from a dermatological disorder.

3.4 Method 3.3, wherein the dermatological disorder is an inflammatory dermatological disorder.

3.5 The preceding method, wherein the inflammatory dermatological disorder is rosacea, psoriasis, atopic dermatitis, hidradenitis suppurativa, seborrheic dermatitis, contact dermatitis, urticaria, dermatitis herpetiformis, nummular dermatitis, lichen planus, *Pityriasis rosea*, cutaneous lupus, acne, cancers of the skin (e.g. cutaneous T-cell lymphoma), or miliaria.

3.6 Any of Methods 3.3-3.5, wherein the inflammatory dermatological disorder is rosacea.

3.7 The preceding method, wherein the rosacea is papulopustular rosacea.

3.8 Any of Methods 3.3-3.5, wherein the inflammatory dermatological disorder is psoriasis.

3.9 Any of Methods 3.3-3.5, wherein the inflammatory dermatological disorder is atopic dermatitis.

3.10 Any of Methods 3.3-3.5, wherein inflammatory dermatological disorder is hidradenitis suppurativa.

3.11 Any of Methods 3.3-3.5, wherein inflammatory dermatological disorder is cutaneous lupus.

3.12 Any of Methods 3.3-3.5, wherein inflammatory dermatological disorder is acne.

3.13 Any of Methods 3.3-3.5, wherein inflammatory dermatological disorder is a cancer of the skin (e.g., cutaneous T-cell lymphoma).

3.14 Any of the preceding methods, the subject is a human.

3.15 Any of the preceding methods, wherein the mammalian skin is human skin.

As used herein, "inflammatory dermatological disorder" refers to disorders involving skin inflammation including, for example, rosacea, psoriasis, atopic dermatitis, hidradenitis suppurativa, seborrheic dermatitis, contact dermatitis, urticaria, dermatitis herpetiformis, nummular dermatitis, lichen planus, *Pityriasis rosea*, cutaneous lupus, acne, cancers of the skin (e.g. cutaneous T-cell lymphoma), and miliaria. Skin inflammation is typically characterized by redness/flushing, pain, pustules, sensation of heat, and/or swelling.

"Lesional skin" of a human having rosacea refers to a site on the skin having active rosacea, such as an active site of erythematotelangiectatic rosacea (e.g., with flushing or visible blood vessels), or an active site of papulopustular rosacea (e.g., skin having an active acne-like breakout of swollen red bumps).

"Mammal" or "mammalian" includes humans and both domestic animals such as laboratory animals and household pets, (e.g., cats, dogs, swine, cattle, sheep, goats, horses, rabbits), and non-domestic animals such as wildlife and the like.

"Therapeutically effective amount" refers to that amount of a compound of the invention which, when administered to a mammal, preferably a human, is sufficient to effect treatment of the disease or condition of interest in a mammal, preferably a human, having the disease or condition. The amount of a compound of the invention which constitutes a "therapeutically effective amount" will vary depending on the compound, the disease or condition and its severity, the manner of administration, and the age of the mammal to be treated, but can be determined routinely by one of ordinary skill in the art having regard to his own knowledge and to this disclosure. Preferably, for purposes of this invention, a "therapeutically effective amount" is that amount of a compound of invention which is sufficient to inhibit inflammation of the skin.

"Treating" or "treatment", as used herein, covers the treatment of the disease or condition of interest in a mammal, preferably a human, and includes:

(i) preventing the disease or condition from occurring in the mammal;

(ii) inhibiting the disease or condition in the mammal, i.e., arresting its development;

(iii) relieving the disease or condition in the mammal, i.e., causing regression of the disease or condition; or (iv) relieving the symptoms of the disease or condition in the mammal, i.e., relieving the symptoms without addressing the underlying disease or condition; or As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Locally reducing inflammation" refers to a decrease or reduction of local inflammation at the site of topical administration of the pharmaceutical composition. Administering a topical composition as described herein may reduce inflammation at the site of the body where the pharmaceutical composition is topically administered. A reduction in local inflammation may be evidenced by decreased redness, decreased swelling, deceased pain or irritation, a decrease in a sensation of heat, and/or decreased expression of one or more inflammation markers such as interleukin-6 (IL-6), C-C motif chemokine ligand 3 (CCL3, or MIP-1alpha).

In the present description, the term "about" means ±20% of the indicated range, value, or structure, unless otherwise indicated.

Any suitable amount of a compound of Formula I, II (e.g., Compound 1, et seq.), or III (e.g., Compound 2, et seq.) can be employed in the dermatological compositions of the present disclosure, provided the amount effectively reduces local inflammation and/or vascular dysfunction, and remains stable in the composition over a prolonged period of time. Preferably, the stability is over a prolonged period of time, e.g., up to about 3 years, up to 1 year, or up to about 6 months, which is typical in the manufacturing, packaging, shipping and/or storage of dermatologically acceptable compositions. A compound of Formula I, II (e.g., Compound 1, et seq.), or III (e.g., Compound 2, et seq.) can be in solution, partially in solution with an undissolved portion or completely undissolved suspension.

In some embodiments, the IRAK4 inhibitor of Formula I, II (e.g., Compound 1, et seq.), or III (e.g., Compound 2, et seq.) is present in the topical composition of the present disclosure at a concentration of about 0.005% to about 20% by weight, e.g., a concentration of about 0.005% to about 15% by weight, or 0.005% to about 10% by weight, or 0.005% to about 5% by weight. In some embodiments, the IRAK4 inhibitor of Formula I, II (e.g., Compound 1, et seq.), or III (e.g., Compound 2, et seq.) is present in the topical composition at a concentration of about 0.01% to about 5% by weight, or about 0.1% to about 5% by weight, about 0.1% to about 1% by weight, about 1% to about 2% by weight, about 2% to about 3% by weight, about 3% to about 4% by weight, or about 4% to about 5% by weight. In some embodiments, the IRAK4 inhibitor of Formula I, II (e.g., Compound 1, et seq.), or III (e.g., Compound 2, et seq.) is present in the topical composition at a concentration of about 0.1%, 0.2%, 0.3%, 0.4%, 0.5%, 0.6%, 0.7%, 0.8%, 0.9% or about 1% by weight; or about 1.5%, 2%, 2.5%, 3%, 3.5%, 4%, 4.5% or about 5% by weight, or a concentration of about 1%, 2%, 3%, 4%, 5%, 6%, 7%, 8%, 9%, 10%, 11%, 12%, 135, 14% or 15% by weight.

In some embodiments, a therapeutically effective dosage should be from about 0.0001 mg to about 1000 mg per day. In some embodiments, a therapeutically effective dosage can be from about 0.001-50 mg of active ingredient (Compound of Formula I as described herein) per kilogram of body weight per day, delivered topically as descried herein. In some embodiments, the Compound of Formula I is administered at a dosage of up to 1500 mg/day, for example 1200 mg/day, 900 mg/day, 850 mg/day, 800 mg/day, 750 mg/day, 700 mg/day, 650 mg/day, 600 mg/day, 550 mg/day, 500 mg/day, 450 mg/day, 400 mg/day, 350 mg/day, 300 mg/day, 250 mg/day, 200 mg/day, 150 mg/day, 1000 mg/day, 50 mg/day, 25 mg/day, 10 mg/day, or 9, 8, 7, 6, 5, 4, 3, 2, 1, 0.75, 0.5, 0.25, 0.10, 0.05 or 0.01 mg/day.

In certain embodiments, the pharmaceutical compositions described herein further include one or more additional dermatologically acceptable excipients. The additional excipients may be one or more solvents that solubilize and/or stabilize the active ingredient (e.g., IRAK4 inhibitors) contained therein, and may include viscosity enhancers, pH adjusters, film forming agents and the like. Non-limiting examples of the suitable additional excipients include, but are not limited to, alcohols such as alkanols with one to twenty carbons, such as oleyl alcohol, cetyl alcohol, octyldodecanol, cetostearyl alcohol, benzyl alcohol, butylene glycol, diethylene glycol, glycofurol, glycerides, glycerin, glycerol, phenethyl alcohol, polypropylene glycol, polyvinyl alcohol, phenoxyethanol and phenol; amides, such as N-butyl-N-dodecylacetamide, crotamiton, N,N-dimethylformamide, N,N-dimethylacetamide, N-methyl formamide, and urea; amino acids, such as L-α-amino acids and water soluble proteins; azone and azone-like compounds, such as azacycloalkanes; essential oils, such as almond oil, amyl butyrate, apricot kernel oil, avocado oil, camphor, castor oil, 1-carvone, coconut oil, corn oil, cotton seed oil, eugenol, menthol, oil of anise, oil of clove, orange oil, peanut oil, peppermint oil, rose oil, safflower oil, sesame oil, shark liver oil (squalene), soybean oil, sunflower oil, and walnut oil; vitamins and herbs, such as aloe, allantoin, black walnut extract, chamomile extract, panthenol, papain, tocopherol, and vitamin A palmitate; waxes, such as candelilla wax, carnuba wax, ceresin wax, beeswax, lanolin wax, jojoba oil, petrolatum; mixes, such as primary esters of fractionated vegetable oil fatty acids with glycerine or propylene glycol, and interesterified medium chain triglyceride oils; fatty acids and fatty acid esters, such as amyl caproate, butyl acetate, caprylic acid, cetyl ester, diethyl sebacate, dioctyl malate, elaidic acid ethyl caprylate, ethyl glycol palmitostearate, glyceryl beheate, glucose glutamate, isobutyl acetate, laureth-4, lauric acid, malic acid, methyl caprate, mineral oil, myristic acid, oleic acid, palmitic acid, PEG fatty esters, polyoxylene sorbitan monooleate, polypropylene glycols, propylene glycols, saccharose disterate, salicylic acid, sodium citrate, stearic acid, soaps, and caproic-, caprylic-, capric-, and lauric-triglycerides; macrocylics, such as butylated hydroxyanisole, cyclopentadecanolide, cyclodextrins; phospholipids and phosphates, such as dialkylphosphates, ditetradecyl phosphate, lecithin, 2-pyrrolidone derivatives, such as alkyl pyrrolidone-5-carboxylate esters, pyroglutamic acid esters, N-methyl pyrrolidone, dioxane derivatives and dioxolane derivatives; sulphoxides, such as dimethyl sulphoxide and decylmethyl sulphoxide; acids, such as alginic acid, sorbic acid, and succinic acid; cyclic amines; imidazolinones; imidazoles; ketones, such as acetone, dimethicone, methyl ethyl ketone, and pentanedione; lanolin derivatives, such as lanolin alcohol, PEG 16 lanolin, and acetylated lanolin; oxazolines; oxazolindinones; proline esters; pyrroles, urethanes; and surfactants, such as nonoxynols, polysorbates, polyoxylene alcohols, polyoxylene fatty acid esters, sodium lauryl sulfate, and sorbitan monostearate, a saturated or unsaturated fatty acid ester, a saturated or unsaturated fatty acid ester, a polyoxythylene fatty ether, a polyoxylene fatty acid esters, diethylene glycol monoethyl ether, 1,3-dimethyl-2-imidazolidinone and/or dimethyl isosorbide, PEG 200, ethanol, glycerol, Transcutol P (diethylene glycol monoethyl ether), propylene glycol, 1,3-dimethyl-2-imidazolidinone (DMI), sodium metabisulfite, butylated hydroxytoluene (BHT), benzyl alcohol, sodium benzoate, isopropyl myristate, diisopropyl adipate, crodamol OHS (ethylhexyl hydroxystearate), mineral oil, Betadex, TWEEN 20, (polyoxyethylene (20) stearyl ether), silicones (eg. dimethicone, cylcomethicone etc), Steareth-2 (Brij S2), Steareth-20 (Brij S20), glyceryl stearate, stearic acid, magnesium stearate, diethylene glycol monoethyl ether, 1,3-dimethyl-2-imidazolidinone.

In some embodiments, the dermatological compositions of the present disclosure include a solvent system that comprises one or more solvents for the IRAK4 inhibitor of the present disclosure. In some embodiments, the solvent system includes one or more solvents selected from a polyether, a polyethylene glycol (e.g., PEG 400), a polyether alcohol (e.g., diethylene glycol monoethyl ether; Transcutol® P), an ether, and an alcohol; for example PEG 400 and diethylene glycol monoethyl ether (Transcutol® P). Further solvents include polyethers, lower polyhydroxy alcohols, ethanol, propylene glycol, isosorbide dimethyl ether, di(ethylene glycol) ethyl ether, mineral oil; light mineral oil; glycols, such as glycerol behenate and polyethylene glycol (PEG), and mixtures thereof. In some embodiments, the solvents can be selected from glycerin, polyethylene glycols, propylene glycol, and mixtures thereof. Suitable polyethylene glycols (PEGs) include all grades of PEGs, having molecular weights of from 300 to about 8000. In some embodiments, the solvents are selected from Transcutol P and polyethylene glycols of molecular weight about 300 to about 600, or from 300 to about 500, or about 400 Daltons.

Further examples of useful solvents include dialkylated mono- or poly-alkylene glycols, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol.

In some preferred embodiments, the topical composition includes a mixture of PEG 400 and Transcutol® P. In some embodiments, the PEG 400 is present in the composition in an amount of from about 20% to about 70% by weight of the composition, or about 35% to about 70% by weight of the composition; or about 35% to about 50% by weight of the composition, or about 40% to about 45% by weight of the composition, or about 55% to about 65% by weight of the composition; or about 40%, about 45%, about 50%, about 55%, or about 60% by weight of the composition. In some embodiments, the diethylene glycol monoethyl ether (Transcutol® P) is present in an amount of from about 10% to about 45% by weight of the composition, or about 10% to about 20% by weight of the composition; or about 20% to about 30% by weight of the composition, or about 10%, about 15%, about 20%, about 25%, about 30%, about 35%, about 40% or about 45% by weight of the composition.

In some embodiments, the topical composition is an aqueous gel, and the w/w ratio of PEG 400/Transcutol® P is from about 0.7 to about 1.1, for example from about 0.8 to about 1.0, for example about 0.9.

In some embodiments, the topical composition is an non-aqueous gel, and the w/w ratio of PEG 400/Transcutol® P is from about 2.2 to about 2.6, for example from about 2.3 to about 2.5, for example about 2.4.

In some embodiments, the topical composition is a cream, and the w/w ratio of PEG 400/Transcutol® P is from about 2.6 to about 3.2, for example from about 2.7 to about 3.1, for example about 2.9.

In some embodiments, the topical composition is an ointment, and the w/w ratio of PEG 400/Transcutol® P is from about 3.5 to about 4.5, for example from about 3.8 to about 4.2, for example about 4.

More detailed description of certain suitable excipients is described below. As will be appreciated, components of the pharmaceutical formulations described herein can possess multiple functions. For example, a given substance may act as both a viscosity increasing agent and as an emulsifying agent.

The skin (especially stratum corneum) provides a physical barrier to the harmful effects of the external environment. In doing so, it also interferes with the absorption or transdermal delivery of topical therapeutic drugs. Thus, a suitable dermatologically acceptable excipient may include one or more penetration enhancers (or permeation enhancers), which are substances that promote the diffusion of the therapeutic drugs (e.g., the IRAK4 inhibitors described herein) through the skin barrier. They typically act to reduce the impedance or resistance of the skin to allow improved permeation of the therapeutic drugs. In particular, substances which would perturb the normal structure of the stratum corneum are capable of disrupting the intercellular lipid organization, thus reducing its effectiveness as a barrier. These substances could include any lipid material which would partition into the stratum corneum lipids causing a direct effect or any material which would affect the proteins and cause an indirect perturbation of the lipid structure. Furthermore, solvents, such as ethanol, can remove lipids from the stratum corneum, thus destroying its lipid organization and disrupting its barrier function.

The topical compositions described herein typically contain one or more carriers, which preferably have a vapor pressure greater than or equal to 23.8 mm Hg at 25° C. Preferred concentration range of a single carrier or the total of a combination of carriers can be from about 0.1 wt. % to about 10 wt. %, more preferably from about 10 wt. % to about 50 wt. %, more specifically from about 50 wt. % to about 95 wt. % of the dermatological composition. Non-limiting examples of the solvent include water (e.g., deionized water) and lower alcohols, including ethanol, 2-propanol and n-propanol.

A dermatological composition of the invention can contain one or more hydrophilic co-solvents, which are miscible with water and/or lower chain alcohols and preferably have a vapor pressure less than water at 25° C. (~23.8 mm Hg). The carrier typically has a vapor pressure greater than or equal to the hydrophilic co-solvent as to concentrate the compound of Formula I, II (e.g., Compound 1, et seq.), or III (e.g., Compound 2, et seq.) on the skin. A hydrophilic co-solvent may be a glycol, specifically propylene glycol. In particular, the propylene glycol can be from the class of polyethylene glycols, specifically polyethylene glycols ranging in molecular weight from 200 to 20000. Preferably, the solvent would be part of a class of glycol ethers. More specifically, a hydrophilic co-solvent of the invention would be diethylene glycol monoethyl ether (transcutol). As used herein, "diethylene glycol monoethyl ether" ("DGME") or "transcutol" refers to 2-(2-ethoxyethoxy)ethanol {CAS NO 001893} or ethyoxydiglycol. Another preferred co-solvent is 1,3-dimethyl-2-imidazolidinone (DMI).

The topical compositions described herein may also contain one or more "humectant(s)" used to provide a moistening effect. Preferably the humectant remains stable in the composition. Any suitable concentration of a single humectant or a combination of humectants can be employed, provided that the resulting concentration provides the desired moistening effect. Typically, the suitable amount of humectant will depend upon the specific humectant or humectants employed. Preferred concentration range of a single humectant or the total of a combination of humectants can be from about 0.1 wt. % to about 70 wt. %, more preferably from about 5.0 wt. % to about 30 wt. %, more specifically from about 10 wt. % to about 25 wt. % of the dermatological composition, or about 10 wt. % to about 20 wt. % of the dermatological composition, or about 10 wt. % to about 15 wt. % of the dermatological composition, such as about 10 wt. %, or about 11 wt. %, or about 12 wt. %, or about 13 wt. %, or about 14 wt. %, or about 15 wt. % of the dermatological composition. Non-limiting examples for use herein include glycerin, polyhydric alcohols and silicone oils. More preferably, the humectant is glycerin, propylene glycol and/or cyclomethicone. Specifically, the filler would be glycerine and/or cyclomethicone.

In certain embodiments, the pharmaceutical compositions include a viscosity enhancing agent and/or an emulsifier. Gelling agents are used to increase the viscosity of the final composition. Emulsifiers are substances that stabilize an emulsion. The viscosity increasing agent can also act as an emulsifying agent. Typically, the concentration and combination of viscosity increasing agents will depend on the physical stability of the finished product. Preferred concentration range of a viscosity increasing agent can be from about 0.01 wt. % to about 20 wt. %, more preferably from about 0.1 wt. % to about 10 wt. %, more specifically from about 0.5 wt. % to about 5 wt. % of the dermatological composition. Non-limiting examples of viscosity increasing agents for use herein include classes of celluloses, acrylate polymers and acrylate crosspolymers, such as, hydroxypropyl cellulose, hydroxymethyl cellulose, (e.g., Benecel E4M), Pluronic PF127 polymer, carbomers (e.g., carbomer 980, carbomer 1342 and carbomer 940), more specifically hydroxypropyl cellulose (e.g., hydroxypropyl cellulose having a molecular weight between 850,000-1,150,000 daltons Klucel® EF, GF, MF and/or HF), Pluronic PF127, carbomer 980 and/or carbomer 1342 (Pemulen® TR-1, TR-2 and/or Carbopol® ETD 2020). Examples of emulsifiers for use herein include polysorbates, laureth-4, and potassium cetyl sulfate.

The topical compositions described herein may contain one or more anti-oxidants, radical scavengers, and/or stabilizing agents, preferred concentration range from about 0.001 wt. % to about 0.1 wt. %, more preferably from about 0.1 wt. % to about 5 wt. % of the dermatological composition. Examples of suitable antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as α-carotone, β-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, α-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as α-linolenic acid, linoleic acid, oleic acid, folic acid and derivatives thereof, ubiquinone and ubiquinol and derivatives thereof, vitamin C and derivatives thereof such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, α-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as zinc oxide, zinc sulfate, selenium and derivatives thereof such as selenium methionine, stilbene and derivatives thereof such as stilbene oxide, trans-stilbene oxide and the like. In particular exemplary embodiments, the one or more antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, and ascorbir stearate. butyl hydroxyanisole, and gallic esters, and in some embodiments, the one or more antioxidants may include BHT. In some embodiments, the antioxidant is selected from one or more of include butylated hydroxytoluene, sodium metabisulfite, butylated hydroxyanisole, ascorbyl palmitate, citric acid, vitamin E, vitamin E acetate, vitamin E-TPGS, ascorbic acid, tocophersolan and propyl gallate. More specifically the anti-oxidant can be metabisulfite, butylated hydroxyanisole, vitamin E, ascorbic acid and/or propyl gallate.

The topical compositions described herein may also contain preservatives that exhibit anti-bacterial and/or anti-fungal properties. Preservatives can be present in any of the gelled, cream ointment, etc. dermatological compositions of the invention to minimize bacterial and/or fungal over its shelf-life. Preservatives include glycerin, esters of parahydroxybenzoic acid such as methyl-, ethyl-, propyl and butyl-parabens, sodium benzoate, sorbic acid and salts thereof such as potassium sorbate, benzoic acid and its salts as sodium benzoate, diazolidinyl urea, alcohols having from 2-20 carbon atoms, including aliphatic alcohols such as ethanol, alcohols containing a saturated, unsaturated or aromatic ring such as benzyl alcohol or phenoxyethanol, chlorobutanol, phenolic compounds such as phenols, cresols such as m-cresol, or quaternary compounds such as benzalkonium chloride and benzethonium chloride, mercury-containing substances such as merfen and thiomerosal, stabilized chlorine dioxide, butylated hydroxytoluene (BHT), butylated hydroxyanisole, tocopherol, propyl gallate, tetrasodium EDTA, vitamin E TPGS, and derivatives thereof, and mixtures thereof. Preferred concentration range of preservatives in a dermatological composition of the invention can be from about 0.001% to about 20% by weight of the composition, or about 0.01% to about 10% by weight of the composition; or about 0.1% to about 5% by weight of the composition, or about 1% to about 3% by weight of the composition, or about 2% by weight of the composition;

The topical compositions described herein may optionally include one or more chelating agents. As used herein, the term "chelating agent" or "chelator" refers to those skin benefit agents capable of removing a metal ion from a system by forming a complex so that the metal ion cannot readily participate in or catalyze chemical reactions. The chelating agents for use herein are preferably formulated at concentrations ranging from about 0.001 wt. % to about 10 wt. %, more preferably from about 0.05 wt. % to about 5.0 wt. % of the dermatological composition. Non-limiting examples for use herein include EDTA, disodium edeate, dipotassium edeate, cyclodextrin, trisodium edetate, tetrasodium edetate, citric acid, sodium citrate, gluconic acid and potassium gluconate. Specifically, the chelating agent can be EDTA, disodium edeate, dipotassium edate, trisodium edetate or potassium gluconate.

The dermatological composition of the present disclosure may be of neutral to mildly acidic pH to allow for comfortable application to the subject's skin, particularly in light of the disease state or condition suffered by the subject. For example, in various embodiments, the pH of the creams may be from about 2.5 to about 7.0, preferably from about 4.0 to about 7.0, more preferably from about 5.0 to about 6.5 at room temperature. In other embodiments, the pH of such creams may be about 5.0, 5.1, 5.2, 5.3, 5.4, 5.5, 5.6, 5.7, 5.8, 5.9, 6.0, 6.1, 6.2, 6.3, 6.4 or 6.5 at room temperature. Any components or combination of components known and useful in the art may be used to achieve an appropriate pH such as, for example, pH adjusters including, but not limited to, lactic acid, citric acid, sodium citrate, glycolic acid, succinic acid, phosphoric acid, monosodium phosphate, disodium phosphate, oxalic acid, dl-malic acid, calcium carbonate, sodium hydroxide, magnesium hydroxide, sodium carbonate, sodium hydrogen carbonate, and ammonium hydrogen carbonate. In certain embodiments the pH regulators comprise a citrate buffer or a phosphate buffer. In some embodiments, the pH adjuster comprises an alkali or alkaline earth hydroxide, e.g. sodium hydroxide or magnesium hydroxide. In various embodiments, the total buffer capacity may be from about from about 0 mM to about 600 mM; from about 0 mM to about 600 mM; from about 5 mM to about 600 mM; from about 5 mM to about 400 mM; from about 5 mM to about 300 mM; from about 5 mM to about 200 mM; from about 200 mM to about 400 mM; about 0 mM, about 100 mM, about 200 mM, about 300 mM, about 400 mM, about 500 mM, or about 600 mM. In some embodiments the cream comprises each pH regulator in an amount of about 0.05%, about 0.1%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% by weight.

The topical compositions described herein may include one or more compatible cosmetically acceptable adjuvants commonly used, such as colorants, fragrances, emollients, and the like, as well as botanicals, such as aloe, chamomile, witch hazel and the like.

Alternatively, other pharmaceutical delivery systems may be employed for the pharmaceutical compositions of the invention. Liposomes and emulsions are well-known examples of delivery vehicles that may be used to deliver active compound(s) or prodrug(s). Certain organic solvents such as dimethylsulfoxide (DMSO) may also be employed.

The topical compositions described herein may be provided in any cosmetically suitable form, preferably as a lotion, a cream, a gel (aqueous or n on-aqueous gel) or a ointment, as well as a sprayable liquid form (e.g., a spray that includes the IRAK4 inhibitor in a base, vehicle or carrier that dries in a cosmetically acceptable way without the greasy appearance that a lotion or ointment would have when applied to the skin).

In treating the inflammatory dermatological disorders such as rosacea, the topical composition comprising a compound of Formula I, II (e.g., Compound 1, et seq.), or III (e.g., Compound 2, et seq.) is preferably administered directly to the affected area of the skin (e.g., rosacea lesion) of the human in need thereof. When such compositions are in use (e.g., when a dermatological composition comprising a compound of Formula I, II (e.g., Compound 1, et seq.), or III (e.g., Compound 2, et seq.) and a dermatologically acceptable excipient is placed upon the skin of the human in need thereof), the compound of Formula I, II (e.g., Compound 1, et seq.), or III (e.g., Compound 2, et seq.) is in continuous contact with the skin of the patient, thereby effecting penetration and treatment.

In topically administering the pharmaceutical compositions of the invention, the skin of the human to be treated can be optionally pre-treated (such as washing the skin with soap and water or cleansing the skin with an alcohol-based cleanser) prior to administration of the dermatological composition of the invention.

The pharmaceutical compositions of the invention may, if desired, be presented in a pack or dispenser device which may contain one or more unit dosage forms containing the active compound(s). The topical composition described herein may also be provided in a patch with the topical composition on the side of the patch that directly contacts the skin. Dermatologically acceptable adhesives may be used to affix the patch to the skin for an extended period of time.

The following Examples may be used by one skilled in the art to determine the effectiveness of the compounds of the invention in treating a human having a dermatological condition characterized by inflammation.

EXAMPLES

Example 1—Saturated Solubility of Compound 1 and Compound 2 in Selected Excipients A series of formulations were created to test the solubilities of two IRAK4 inhibitors according to the present disclosure. The formulations were created to a range of systems suitable for topical application (creams, PEG ointments, aqueous gels and non-aqueous gels).

Initially saturated solubility of both Compound 1 and Compound 2 was assessed in a range of twenty excipients suitable for topical application to determine solvents and non-solvents for further formulation development work. The results are presented in Table 1 and summarized as follows:

For Compound 1:

- The following solvents for Compound 1 were identified (solubility >0.2% w/w): benzyl alcohol (1.436% w/w), phenoxyethanol (0.442% w/w), Transcutol P (0.276% w/w), SR dimethyl isosorbide (0.267% w/w), PEG 400 (0.203% w/w).
- Relatively low Compound 1 solubility was observed in IPP (0.141% w/w), ethanol (0.072% w/w), propylene glycol (0.030% w/w), and isopropanol (0.017% w/w).
- Minimal solubility of T-Compound 1 was apparent in deionised water at both pH's assessed, with a marginally higher solubility observed at pH 7 (0.009% w/w) when compared to pH 4 (BLOQ).
- Minimal solubility of T-Compound 1 (≤0.009% w/w) was observed in the remaining excipients tested i.e. propylene glycol dicaprylate, mineral oil, castor oil, butyl stereate, oleyl alcohol, IPM, Miglyol 810, glycerin and diisopropyl adipate.

For Compound 2:

- The following solvents for T-Compound 2 were identified (solubility >2% w/w): Transcutol P (4.795% w/w), benzyl alcohol (4.795% w/w), PEG 400 (2.830% w/w), phenoxyethanol (2.650% w/w) and SR dimethyl isosorbide (2.613% w/w).
- Lower Compound 2 solubility was observed in propylene glycol (0.426% w/w), ethanol (0.193% w/w), isopropanol (0.159% w/w), IPP (1.141% w/w), ethanol (0.072% w/w), castor oil (0.064% w/w), and diisopropyl adipate (0.050% w/w).
- Compound 2 was found to be insoluble in deionized water (regardless of the pH).
- Minimal solubility of Compound 2 (≤0.013% w/w) was observed in propylene glycol dicaprylate, IPP, mineral oil, butyl stearate, oleyl alcohol, Miglyol 810 and glycerine.

TABLE 1

Saturated solubility of Compound 1 and Compound 2 (% w/w) in excipients suitable for topical application, determined by HPLC (mean of n = 2-3 (range)).

| Excipient | Saturated solubility of Compound 1 (% w/w) | Saturated solubility of Compound 2 (% w/w) |
|---|---|---|
| Deionised water pH 4 | BLOQ | BLOQ |
| Deionised water pH 7 | 0.009 (0.003-0.018) | BLOQ |
| Ethanol | 0.072 (0.054-0.090) | 0.193 (0.177-0.221) |
| PEG 400 | 0.203 (0.201-0.205) | 2.830 (2.828-2.835) |
| Transcutol P | 0.276 (0.274-0.278) | 4.795 (4.716-4.880) |
| Propylene glycol | 0.030 (0.030-0.030) | 0.426 (0.424-0.428) |
| Propylene glycol dicaprylate | 0.002 (0.002-0.002) | 0.002 (0.002-0.002) |

TABLE 1-continued

Saturated solubility of Compound 1 and Compound 2 (% w/w) in excipients suitable for topical application, determined by HPLC (mean of n = 2-3 (range)).

| Excipient | Saturated solubility of Compound 1 (% w/w) | Saturated solubility of Compound 2 (% w/w) |
|---|---|---|
| Isopropyl palmitate (IPP) | 0.141 (0.138-0.144) | BLOQ |
| Mineral oil (liquid paraffin) | BLOQ | BLOQ |
| Castor oil | 0.008 (0.008-0.008) | 0.064 (0.060-0.066) |
| Butyl stearate | BLOQ | BLOQ |
| Oleyl alcohol | 0.003 (0.003-0.003) | 0.012 (0.012-0.012) |
| Isopropyl myristate (IPM) | BLOQ | BLOQ |
| Miglyol 810 | 0.002 (0.002-0.002) | 0.003 (0.003-0.003) |
| Glycerin (Glycerol) | 0.001 (0.001-0.001) | 0.013 (0.013-0.013) |
| Diisopropyl adipate | 0.009 (0.009-0.009) | 0.050 (0.050-0.051) |
| Benzyl alcohol | 1.436 (1.428-1.446) | 4.795 (4.743-4.883) |
| Isopropanol (Isopropyl alcohol) | 0.017 (0.017-0.017) | 0.159 (0.154-0.162) |
| Phenoxyethanol | 0.442 (0.411-0.460) | 2.650 (2.623-2.669) |
| SR Dimethyl Isosorbide | 0.267 (0.264-0.268) | 2.163 (2.131-2.188) |

In summary, various solvents and non-solvents for both Compound 1 and Compound 2 were identified and the pH was not found to have a significant impact on the solubility of these compounds in water. Compound 2 overall demonstrated higher solubility in majority of the excipients tested in comparison to Compound 1. The only exceptions were IPP (0.141% w/w for Compound 1 vs BLOQ for Compound 2) and deionised water pH 7 (0.009% w/w for Compound 1 vs BLOQ for Compound 2).

Example 2—Excipient Compatibility

Based on the results of Example 1, and forced degradation experiments, a range of excipients and binary systems were selected for short-term Compound 1 and screening. For example, systems with and without BHT were assessed to further confirm the requirement for antioxidants. Additionally, assessed were binary systems consisting of PEG400 and water due to limited solubility of Compound 1 and Compound 2 in water. These binary systems were also pH adjusted (pH 5, 6 and 7 reflecting typical range for topical formulations) to determine any impact that pH might have on stability of these compounds.

The tested excipients were PEG 400, Transcutol® P, 50:50 v/v ethanol:Transcutol® P, PEG 400+0.1% BHT, 80:20 v/v PEG 400:water, benzyl alcohol, Super Refined™ Arlasolve™ DMI (SR DMI), 80:20 v/v Transcutol® P:glycerol, 80:20 v/v Transcutol® P:glycerol+0.1% BHT, 80:20 v/v Transcutol® P:propylene glycol, 80:20 v/v Transcutol® P:propylene glycol+0.1% BHT, 80:20 v/v PEG 400:water+0.1% BHT pH 5, 80:20 v/v PEG 400:water+0.1% BHT pH 6, 80:20 v/v PEG 400:water+0.1% BHT pH 5, 80:20 v/v Transcutol® P:isopropanol, 80:20 v/v Transcutol® P:isopropanol+0.1% BHT. The percentage recovery and peak purity (% area) of Compound 1 and Compound 2 was assessed at T=0 and following storage for 2 and 4 weeks at 40 and 50° C. The results are summarized as follows:

A decrease in Compound 1 peak purity and corresponding decrease in drug recovery was observed in PEG 400 and 80:20 v/v PEG 400:water following 4 weeks at 50° C. (Compound 1 peak purity of 91.33% area and 66.87% area, respectively). A slight decrease in peak purity and drug recovery following storage at 50° C. in PEG 400 was also observed for T-Compound 2 (Compound 2 peak purity of 96.58% area). Inclusion of BHT was observed to improve the stability of both compounds in PEG 400, with no/marginal decrease in Compound 1/Compound 2 peak purity and drug recovery reported for PEG 400+0.1% BHT.

A gradual decreasing trend in Compound 1 and Compound 2 peak purity and recovery was observed to continue over the storage period for SR DMI (Compound 1 peak purity of 21.62% area and Compound 2 peak purity of 36.35 area following 4 weeks at 50° C.).

The impact of pH on the stability of both T-Compound 1 and T-Compound 2 in water-based systems containing PEG400, water and BHT was also assessed but no difference between stability of the compounds over the 4 weeks storage period was observed (possibly due to the stabilizing effect of BHT).

Compound 1 and Compound 2 peak purity remained consistent over the T=4 weeks storage period in the remaining excipients and binary systems tested indicating their suitability for incorporation into formulations containing the drugs. While minor variations in the recovery values have been observed over the testing period, it is important to note that the extraction procedure employed was generic and as such has not been optimized.

In summary, both Compound 1 and Compound 2 exhibited chemical stability in majority of the excipients and binary systems tested, allowing for identification of excipients suitable for incorporation into topical formulations and confirming the need for inclusion of an antioxidant (such as BHT).

Example 3—Solvent Systems (Saturated Solubility)

To give an indication of feasible formulation types and to understand the achievable drug concentration, the saturated solubility of Compound 1 and Compound 2 was determined in solvent systems including aqueous gels (SSA1-SSA9), creams (SSC1-SSC2), non-aqueous gels (SSNA1-SSNA5) and PEG ointments (SSPO1-SSPO2, SSPO4). The compositions of solvent systems are presented in Table 2.

TABLE 2

Compositions (% w/w) of solvent systems developed for IRAK4 inhibitors

| Excipient | A1 | A2 | A3 | A4 | SSA5 | SSA6 | SSA8 | SSA9 | C1 |
|---|---|---|---|---|---|---|---|---|---|
| PEG 400 | 69.90 | 62.90 | 42.90 | 52.90 | 47.90 | 67.90 | 52.90 | 32.90 | 32.90 |
| Diethylene Glycol Monoethyl Ether (Transcutol P) | 15.00 | 25.00 | 45.00 | 15.00 | 25.00 | — | 25.00 | 45.00 | 15.00 |
| Water | 13.00 | 10.00 | 10.00 | 10.00 | 10.00 | 10.00 | 20.00 | 20.00 | 30.00 |
| Ethanol | — | — | — | — | — | — | — | — | — |
| Benzyl Alcohol | 2.00 | 2.00 | 2.00 | 2.00 | 2.00 | 2.00 | 2.00 | 2.00 | 2.00 |
| Glycerol | — | — | — | 20.00 | — | — | — | — | — |
| Propylene Glycol | — | — | — | — | 15.00 | 20.00 | — | — | — |
| Butylated Hydroxytoluene (BHT) | 0.10 | 0.10 | 0.10 | 0.10 | 0.10 | 0.10 | 0.10 | 0.10 | 0.10 |
| Total | 100.00 | 100.00 | 100.00 | 100.00 | 100.00 | 100.00 | 100.00 | 100.00 | 80.00 |
| Excipient | C2 | NA1 | NA2 | NA3 | NA4 | NA5 | PO1 | PO2 | PO4 |
| PEG 400 | 52.90 | 64.90 | 69.90 | 67.90 | 64.90 | 54.90 | 59.90 | 52.90 | 52.90 |
| Diethylene Glycol Monoethyl Ether (Transcutol P) | — | 25.00 | 10.00 | — | 25.00 | 45.00 | 15.00 | 10.00 | — |
| Water | 25.00 | — | — | — | — | — | — | 10.00 | 10.00 |
| Ethanol | — | 10.00 | — | — | — | — | — | — | — |
| Benzyl Alcohol | 2.00 | — | — | 2.00 | — | — | — | 2.00 | 2.00 |
| Glycerol | — | — | 20.00 | 10.00 | 10.00 | — | — | — | — |
| Propylene Glycol | — | — | — | 20.00 | — | — | — | — | 10.00 |
| Butylated Hydroxytoluene (BHT) | 0.10 | 0.10 | 0.10 | 0.10 | 0.10 | 0.10 | 0.10 | 0.10 | 0.10 |
| Total | 80.00 | 100.00 | 100.00 | 100.00 | 100.00 | 100.00 | 75.00 | 75.00 | 75.00 |

Aqueous Gel Solvent Systems

A range of aqueous gel solvent systems (SSA1-SSA5) with varying amount of PEG400 (32.90-69.90% w/w; solvent for the drugs) and Transcutol P (0=45% w/w; solvent for the drugs and penetration enhancer) were designed. Due to no/limited solubility of Compound 1 and Compound 2 in water, low levels of water (10-20% w/w) were included in these solvent systems. All aqueous gel solvent systems contained BHT (antioxidant to mitigate oxidative degradation as seen during previous experiments) and benzyl alcohol (solvent for the drugs and preservative). Glycerol (humectant) was additionally included in SSA4 and propylene glycol (alternative penetration enhancer) was included in SSA5 and SSA6. The results can be summarized as follows:

For Compound 1:

Saturated solubility of Compound 1 in aqueous solvent systems ranged from 0.14% w/w (SSA6; 10% water, 0% Transcutol P) to 0.38% w/w (SSA3, 10% water, 45% w/w Transcutol P).

Saturated solubility of Compound 1 was observed to decrease with an increase in the water content (compare SSA3 and SSA9) and to increase with an increase in the Transcutol P content (compare SSA1, SSA2 and SSA3).

Saturated solubility of Compound 1 in systems containing propylene glycol was observed to be in the range of 0.14%-0.20% w/w.

For Compound 2:

Across the aqueous solvent systems, Compound 2 displayed greater solubility than to Compound 1 and followed a comparable trend. Systems with low Transcutol P (SSA1

15%, SSA4—15% and SSA6—0%), resulted in the lowest solubility of Compound 2 at 0.34% w/w (SSA1) and 0.26% w/w (SSA4 and SSA6).

The inclusion of propylene glycol (SSA5 and SSA6) and glycerol (SAA4) at the expense of Transcutol P lowered the solubility (as seen with Compound 1).

Non-Aqueous Gel Solvent Systems

A range of non-aqueous gel solvent systems (SSNA1-SSNA5) with varying amount of PEG400 (54.90-69.90% w/w; solvent for the drugs) and Transcutol P (0-45% w/w; solvent for the drugs and penetration enhancer) were designed. All non-aqueous gel solvent systems contained BHT (antioxidant to mitigate oxidative degradation as seen during previous experiments). Benzyl alcohol (solvent for the drugs and preservative) was additionally included in SSNA3, glycerol (humectant) was included in SSNA2-SSNA4 and propylene glycol (alternative penetration enhancer) was included in SSNA3. The results can be summarized as follows:

For Compound 1:

Saturated solubility of Compound 1 in non-aqueous solvent systems ranged from 0.13% w/w (SSNA3) to 0.24% w/w (SSNA1).

Glycerol was included in both SSNA2 and SSNA3 and propylene glycol in SSNA3 at the expense of Transcutol P, which resulted in low solubility for Compound 1.

For Compound 2:

Saturated solubility of Compound 2 in non-aqueous systems was observed to be much greater than that of Compound 1. The solubility ranged from 3.39% w/w (SSNA3) to 5.26% w/w (SSNA1).

As with the solubility pattern of Compound 1 in non-aqueous solvent systems, similar trends were observed for Compound 2. The introduction of propylene glycol and glycerol at the expense of Transcutol P negatively impacted the solubility.

The inclusion of ethanol increased the saturated solubility of Compound 2 (SSNA1; 5.26% w/w) in comparison to a system with no ethanol but higher levels of Transcutol P and lower levels of PEG 400 (SSNA5; 4.52% w/w).

Cream Solvent Systems

Two solvent systems suitable for use in emulsion-based cream formulations were designed (SSC1-SSC2)—with and without Transcutol P and containing low water amounts (25-30%). The solvent systems represent the aqueous phase of the emulsion and, as such, components do not sum to 100%. The results can be summarized as follows:

Low saturated solubility of both Compound 1 and Compound 2 was observed in SSC1 and SSC2 i.e. 0.07-0.08% w/w for Compound 1 and 0.04% w/w for T-3774394.

The inclusion of Transcutol P (SSC1) did not have an impact on the solubility of Compound 1 and Compound 2, with both SSC1 and SSC2 solvent systems analysed displaying near identical results. SSC2 contained higher PEG 400 levels (solvent for the drugs) and lower water levels (non-solvent for the drugs).

PEG Ointment Solvent Systems

PEG ointment solvent systems (SSPO1-SSPO2 and SSPO4) with varying amount of PEG400 (52.90-59.90% w/w; solvent for the drugs) and Transcutol P (0-15% w/w; solvent for the drugs and penetration enhancer) were designed. Propylene glycol (alternative penetration enhancer) was included in SSPO4. Water at a level of 10% was included in SSPO2 and SSPO4, while no water was included in SSPO1. The results can be summarized as follows:

The saturated solubility of Compound 2 was found to be low in the PEG ointment solvent systems containing either water and/or propylene glycol (<0.3% w/w), however Compound 2 was found to be highly soluble (5.08% w/w) in the PEG ointment solvent system (SSPO1).

TABLE 3

Saturated solubility of Compound 1 and Compound 2 (% w/w) in solvent systems, determined by HPLC

| Solvent system | Saturated solubility of Compound 1 (% w/w) | Saturated solubility of Compound 2 (% w/w) |
|---|---|---|
| SSA1 | 0.28 (0.26-0.30) | 0.34 (0.34-0.34) |
| SSA2 | 0.31 (0.31-0.32) | 0.47 (0.47-0.47) |
| SSA3 | 0.38 (0.37-0.38) | 0.49 (0.49-0.49) |
| SSA4 | 0.16 (0.16-0.17) | 0.26 (0.26-0.26) |
| SSA5 | 0.20 (0.20-0.20) | 0.32 (0.32-0.32) |
| SSA6 | 0.14 (0.14-0.14) | 0.26 (0.26-0.26) |
| SSA8 | 0.22 (0.22-0.22) | N/A |
| SSA9 | 0.28 (0.28-0.29) | N/A |
| SSC1 | 0.08 (0.08-0.08) | 0.04 (0.04-0.04) |
| SSC2 | 0.07 (0.06-0.08) | 0.04 (0.04-0.04) |
| SSNA1 | 0.24 (0.24-0.24) | 5.26 (5.24-5.28) |
| SSNA2 | 0.14 (0.14-0.15) | 4.11 (4.09-4.12) |
| SSNA3 | 0.13 (0.13-0.13) | 3.39 (3.27-3.48) |
| SSNA4 | N/A | 4.56 (4.55-4.57) |
| SSNA5 | N/A | 4.52 (4.51-4.54) |
| SSPO1 | 0.23 (0.20-0.27) | 5.08 (5.06-5.10) |
| SSPO2 | N/A | 0.29 (0.29-0.29) |
| SSPO4 | N/A | 0.20 (0.19-0.20) |

Example 4—Short Term Stability of Solvent Systems

The short term stability of six solvent systems (SSA1, SSA2, SSA3, SSC1, SSNA1 and SSPO1) containing 0.1% w/w of Compound 1 and Compound 2 (where feasible; concentration reflecting the greatest ratio of excipients to the drugs (worst case scenario) rather than the maximum solubility level) was determined where Compound 1 and Compound 2 content and purity were assessed at T=0 and following storage at 40 and 50° C. for T=2 and 4 weeks. The results can be summarized as follows:

For Compound 1: At T=0 a peak purity of 99.94-99.95% area was reported for Compound 1 for all solvent systems assessed. By the end of the stability testing period Compound 1 peak purity remained consistent with T=0, with the highest, albeit still minor, peak purity decrease (ca. 1% area) reported for SSNA1 and SSPO1 following storage at 50° C. for 4 weeks. Consistent peak purity indicates that Compound 1 solvent systems were chemically stable over the assessed period. Minor variations to Compound 1 recovery (95.95-98.67%) were observed through the testing period, which is thought to be linked to a not fully optimised extraction procedure.

For Compound 2: At T=0 a peak purity of 99.88-99.92% area was reported for Compound 2 for all solvent systems assessed. No obvious deviation from the T=0 results was observed following storage for 4 weeks, with minor Compound 2 peak purity decrease (ca.1% area) reported at 50° C. for SSC1, confirming chemical stability of Compound 2 solvent systems over the assessed period. As for Compound 1, minor variations to Compound 2 recovery (98.38-101.78%) were observed.

Example 5—Additional Formulations

A further selection of formulation types (aqueous and non-aqueous gels, creams and PEG ointments) were prepared. All formulations contained the Compound 1 or Compound 2 at 80% of saturated solubility in the relevant solvent system. The aqueous gels and cream formulations were the primary focus of Compound 1 (shown in Table 4) and non-aqueous formulations were the primary focus for Compound 2 (shown in Table 5).

TABLE 4

Compositions (% w/w) of Compound 1 aqueous gel and cream formulations

| Description | Compound 1 formulation composition (% w/w) | | | | | | | |
|---|---|---|---|---|---|---|---|---|
| | AG1 | AG2 | A3G | AG4 | AG5 | AG6 | CR3 | CR4 |
| PEG 400 | 69.90 | 62.90 | 42.90 | 52.90 | 47.90 | 67.90 | 52.90 | 32.90 |
| Diethylene Glycol Monoethyl Ether (Transcutol ® P) | 15.00 | 25.00 | 45.00 | 15.00 | 25.00 | — | 25.00 | 45.00 |
| Water | 13.00 | 10.00 | 10.00 | 10.00 | 10.00 | 10.00 | 20.00 | 20.00 |
| Benzyl Alcohol | 2.00 | 2.00 | 2.00 | 2.00 | 2.00 | 2.00 | 2.00 | 2.00 |
| Butylated Hydroxytoluene (BHT) | 0.10 | 0.10 | 0.10 | 0.10 | 0.10 | 0.10 | 0.10 | 0.10 |
| Carbopol 980 NF | 1.00 | | 1.00 | — | 1.00 | — | — | — |
| Carbopol 974 NF | — | 1.00 | — | 1.00 | — | 1.00 | — | — |
| Cetyl alcohol | — | — | — | — | — | — | 10.00 | — |
| Brij S2 | — | — | — | — | — | — | 0.71 | — |
| Liquid Paraffin | — | — | — | — | — | — | 5.00 | — |
| Brij S20 | — | — | — | — | — | — | 4.29 | — |
| Stearic acid | — | — | — | — | — | — | — | 13.94 |
| Cetomacrogol 1000 | — | — | — | — | — | — | — | 4.23 |
| Span 60 | — | — | — | — | — | — | — | 0.77 |
| Diamethicone 350 cst | — | — | — | — | — | — | — | 1.00 |
| Compound 1 | 0.30 | 0.30 | 0.25 | 0.25 | 0.23 | 0.23 | 0.05 | 0.06 |
| Total | 100.00 | 100.00 | 100.00 | 100.00 | 100.00 | 100.00 | 100.00 | 100.00 |

TABLE 5

Compositions (% w/w) of Compound 2 cream, non-aqueous gel and aqueous gel formulations

| Description | Compound 2 formulation composition (% w/w) | | | | | | | | |
|---|---|---|---|---|---|---|---|---|---|
| | CR3 | CR4 | NAG1 | NAG3 | NAG4 | PO1 | PO2 | PO3 | PO4 |
| PEG 400 | 52.85 | 32.90 | 59.70 | 60.25 | 50.28 | 55.84 | 54.84 | 52.67 | 52.74 |
| Diethylene Glycol Monoethyl Ether (Transcutol ® P) | — | 15.00 | 25.00 | 25.00 | 45.00 | 15.00 | 15.00 | 10.00 | — |
| Propylene glycol | — | — | — | — | — | — | — | 10.00 | — |
| Water | 25.00 | 30.00 | — | — | — | — | — | 10.00 | 10.00 |
| Benzyl Alcohol | 2.00 | 2.00 | | | | | | 2.00 | 2.00 |
| Ethanol | — | — | 10.00 | — | — | — | — | — | — |
| Glycerol | — | — | — | 10.00 | — | — | — | — | — |
| Butylated Hydroxytoluene (BHT) | 0.10 | 0.10 | 0.10 | 0.10 | 0.10 | 0.10 | 0.10 | 0.10 | 0.10 |

TABLE 5-continued

| Compositions (% w/w) of Compound 2 cream, non-aqueous gel and aqueous gel formulations | | | | | | | | | |
|---|---|---|---|---|---|---|---|---|---|
| | Compound 2 formulation composition (% w/w) | | | | | | | | |
| Description | CR3 | CR4 | NAG1 | NAG3 | NAG4 | PO1 | PO2 | PO3 | PO4 |
| HPC-HF | — | — | 1.00 | 1.00 | 1.00 | — | — | — | — |
| Cetyl alcohol | 10.00 | — | — | — | — | — | — | — | — |
| Brij S2 | 0.71 | — | — | — | — | — | — | — | — |
| Liquid Paraffin | 5.00 | — | — | — | — | — | — | — | — |
| Brij S20 | 4.29 | — | — | — | — | — | — | — | — |
| PEG 4000 | — | — | — | — | — | — | 25.00 | 25.00 | — |
| IPM | — | — | — | — | — | — | 1.00 | — | — |
| PEG 3350 | — | — | — | — | — | 25.00 | — | — | 25.00 |
| Stearic acid | — | 13.97 | — | — | — | — | — | — | — |
| Cetomacrogol 1000 | — | 4.23 | — | — | — | — | — | — | — |
| Span 60 | — | 0.77 | — | — | — | — | — | — | — |
| Diamethicone 350 cst | — | 1.00 | — | — | — | — | — | — | — |
| Compound 2 | 0.03 | 0.03 | 4.20 | 3.65 | 3.62 | 4.06 | 4.06 | 0.23 | 0.16 |
| Total | 100.00 | 100.00 | 100.00 | 100.00 | 100.00 | 100.00 | 100.00 | 100.00 | |

Macroscopic and accelerated stability assessment (centrifugation at high speed until phase separation was observed) was performed for the formulations. The results can be summarized as follows.

Aqueous Gel Formulations (Compound 1)

Then aqueous gel formulations were based on the solvent system with the highest Compound 1 saturated solubility and containing 25-45% Transcutol P (SSA2, SSA3 and SSA9). The following polymers at a level of 1% were investigated: Carbopol 980 NF and Carbopol 974 NF. The development activities are summarised below:

All active aqueous gels (AG1-AG6) were observed to be pourable with low to medium viscosity, thus suggesting that the type of the polymer (at 1.0% level) did not greatly differ the visual viscosity of the gels.

The gels containing Carbopol 980 NP (AG1, AG3 and AG5) appeared transparent whereas those containing Carbopol 974 NF (AG2, AG4 and AG6) appeared slightly turbid.

Aqueous gel formulations were successfully developed with a Compound 1 concentration ranging from 0.23% w/w to 0.30% w/w.

Cream Formulations (Compound 1 and Compound 2)

The Cream formulations for both Compound 1 and Compound 2 employed two previously assessed cream solvent systems (SSC1 and SSC2), and different oil phases (cetyl alcohol, liquid paraffin, Brij S2 and Brij S20 in CR3; stearic acid, Cetomacrogol 1000, Span 60 and diamethicone 350 CST in CR4). While low concentrations of both Compound 1 and Compound 2 (up to 0.06% w/w) were achievable in cream formulations, the development work showed indications of formulation stability and desirable aesthetic properties. Furthermore, cream solvent system (SSC1) was observed to perform well in the sRICA efficacy assay (specifically for Compound 1, see Example 17 below). The results are summarized below:

The Compound 1 active cream formulations (CR3 and CR4) were non-pourable, viscous, white in appearance and smooth upon application. CR3 and CR4 were observed to phase separate after centrifugation for 8 and 10 min, respectively.

The Compound 2 active cream formulations (CR3 and CR4) were both non-pourable, viscous, white in appearance and smooth upon application. No phase separation of CR3 and CR3 was observed after centrifugation for 10 min.

The differing compositions of the creams made no significant impact on the macroscopic characteristics of the creams. However, the selection of Compound 1 or Compound 2 did impact the accelerated stability of the creams, with the Compound 2 cream formulations appearing more stable under accelerated stability testing (centrifugation).

Non-aqueous gel formulations (Compound 2)

Active gel formulations were prepared employing the non-aqueous gel solvent systems with the highest Compound 2 saturated solubility and containing 25-45% Transcutol P (SSNA1, SSNA4 and SSNA5). HPC-HF, a cellulose-based polymer, was used as a gelling agent (at a level of 1%). The results are summarised below:

The Compound 2 active non-aqueous gel formulations (NAG1, NAG3 and NAG4) were all pourable, transparent, with the inherent slightly tacky feel of HPC where NAG1 appeared more viscous than NAG3/4.

The tacky nature of the non-aqueous gels is an inherent characteristic of the gelling agent (HPC-HF) employed in these formulations.

Non-aqueous gel formulations were successfully developed with a Compound 2 concentration ranging from 3.62% w/w to 4.20% w/w.

PEG ointment formulations (Compound 2)

PEG ointment formulations were prepared for Compound 2 employing the three previously assessed PEG ointment solvent systems—i.e. SSPO1, SSPO2 and SSPO4. Different high molecular weight PEGs were assessed—PO1 and PO4 formulations included PEG 3550, while PO2 and PO4 formulations included PEG 4000. Dimethicone 350 cst (skin conditioner) was additionally included in PO2 to enhance the cosmetic properties of the developed formulation. The results are summarized below:

The Compound 2 active PEG ointment formulations (PO1-PO4) all displayed the same physical characteristics being off white, opaque and viscous, suggesting that the differing compositions (different solvent systems and high molecular PEGs) made no significant impact on the macroscopic characteristics of the ointments.

No phase separation was observed for any of the ointments after 16 min of centrifugation.

The major difference between the developed ointments was that formulations based on water-free SSPO1 (PO1 and PO2) had Compound 2 loading of 4.06% w/w, whereas formulations based on SSPO2 (PO3) and SSPO4 (PO4), containing water, had API loading of 0.23% w/w and 0.16% w/w, respectively.

Example 6—Additional Excipients and Solvent Systems

Saturated solubility of both Compound 1 and Compound 2 was assessed in an additional 16 excipients/systems suitable for topical application. The results are shown below in Table 6:

TABLE 6

| Excipient | Saturated solubility of Compound 1 (% w/w) | Saturated solubility of Compound 2(% w/w) |
|---|---|---|
| Dimethicone 350 cst | 0.001 (0.001-0.001) * | BLOQ |
| Dimethicone 20 cst | 0.002** | BLOQ |
| Octyldodecanol (Kollicream OD) | 0.003 (0.002-0.004) *** | 0.005 (0.005-0.006) |
| Isostearic acid | 0.005 (0.004-0.006) | 0.098 (0.097-0.100) |
| Crodamol GTCC | 0.003 (0.002-0.003) | BLOQ |
| Dipropylene Glycol | 0.070 (0.070-0.071) * | 1.287 (1.283-1.292) |
| Water for irrigation (pH 6.16) | 0.007 (0.002-0.012) *** | 0.004** |
| Labrasol | 0.099 (0.098-0.099) | 3.445 (3.223-3.580) |
| 0.6% w/v Myrj S40 in water | 0.003 (0.002-0.003) | BLOQ |
| 5% v/v Tween 80 in water | 0.005 (0.005-0.005) | BLOQ |
| 4% w/v Brij S20 in water | 0.009 (0.008-0.009) | 0.004 (0.003-0.004) |
| 1% w/v Brij L23 in water | 0.002 (0.002-0.003) | 0.004** |
| 1% w/v Poloxamer 407 in water | 0.003 (0.002-0.004) *** | BLOQ |
| 1% w/v Brij O10 in water | 0.002 (0.001-0.002) | BLOQ |

TABLE 6-continued

| Excipient | Saturated solubility of Compound 1 (% w/w) | Saturated solubility of Compound 2(% w/w) |
|---|---|---|
| 8% w/v Cetomacrogol 1000 in water | 0.020 (0.019-0.021) | 0.006 (0.006-0.006) |
| Hexylene Glycol | 0.015 (0.015-0.015) | 0.266 (0.263-0.271) |

These data are summarized as follows:

Compound 1 was found to be relatively insoluble across all the excipients assessed with the highest saturated solubility observed for Labrasol (surfactant) at 0.099% w/w.

A number of the excipients (dimethicone 350 cst and 20 cst, octyldodecanol, Crodamol GTCC, water for irrigation, 0.6% w/v Myrj S40 in water, 5% v/v Tween 80 in water, 4% w/v Brij S20 in water, 1% w/v Brij L23 in water, 1% w/v Poloxamer 407 in water, 1% w/v Brij 010 in water and 8% w/v Cetomacrogol 1000 in water) were identified as non-solvents for Compound 2 (BLOQ or close to LOQ). Limited Compound 2 solubility was reported for isostearic acid, and hexylene glycol (≥0.098% w/w). In comparison high Compound 2 saturated solubility was observed in Labrasol and dipropylene glycol (3.445% w/w and 1.287% w/w, respectively).

Inclusion of a wide range of surfactants did not appear to increase the aqueous solubility of either of the APIs.

Example 7—Further Solvent Systems

The following additional solvent systems were prepared based on the solvents systems described in the preceding Examples, varying in the levels and type of surfactants, penetration enhancers and skin conditioners. The focus for Compound 1 was on aqueous systems (aqueous gels and creams) with lower drug loading, and for Compound 2 on water free gel systems allowing for higher drug loading, and cream and ointments. The compositions are shown in Table 7 below:

TABLE 7

Compositions (% w/w) of Additional Solvent Systems

| Excipient | Solvent System composition (% w/w) | | | | | | | | |
|---|---|---|---|---|---|---|---|---|---|
| | SSA10 | SSA11 | SSA12 | SSA13 | SSA14 | SSC3 | SSC4 | SSC5 | SSC6 |
| PEG400 | 45.00 | 65.00 | 59.90 | 59.90 | 34.95 | 32.90 | 32.90 | 22.90 | 32.90 |
| Diethylene Glycol Monoethyl Ether (Transcutol ® P) | 45.00 | 25.00 | 25.00 | 25.00 | 25.00 | 15.00 | 15.00 | 25.00 | 15.00 |
| Water | 10.00 | 10.00 | 5.00 | 5.00 | 5.00 | 30.00 | 30.00 | 30.00 | 30.00 |
| Benzyl Alcohol | — | — | — | — | — | 2.00 | 2.00 | 2.00 | 2.00 |
| Glycerol | — | — | — | — | — | — | — | — | — |
| Butylated Hydroxytoluene (BHT) | — | — | 0.10 | 0.10 | 0.10 | 0.10 | 0.10 | 0.10 | 0.10 |
| Brij S20 | — | — | — | — | — | 4.00 | — | — | — |
| Tween 80 | — | — | — | — | — | — | 5.00 | — | — |
| Diamethicone 350 cst | — | — | — | — | — | — | — | — | 1.00 |
| Propylene Glycol | — | — | 10.00 | — | — | — | — | — | — |
| Dipropylene glycol | — | — | — | 10.00 | — | — | — | — | — |
| Diisopropyl adipate | — | — | — | — | — | — | — | — | — |

TABLE 7-continued

Compositions (% w/w) of Additional Solvent Systems

| | | | | | | | | | |
|---|---|---|---|---|---|---|---|---|---|
| PEG 300 | — | — | — | — | 34.95 | — | — | — | — |
| Oleyl alcohol | — | — | — | — | — | — | — | — | — |
| Total | 100.00 | 100.00 | 100.00 | 100.00 | 100.00 | 100.00 | 100.00 | 100.00 | |

| | Solvent System composition (% w/w) | | | |
|---|---|---|---|---|
| Excipient | SSC8 | SSNA6 | SSNA7 | SSNA9 |
| PEG400 | 44.90 | 65.00 | 64.90 | 69.90 |
| Diethylene Glycol Monoethyl Ether (Transcutol ® P) | 15.00 | 25.00 | 25.00 | 25.00 |
| Water | 20.00 | — | — | — |
| Benzyl Alcohol | — | — | — | — |
| Glycerol | — | 10.00 | — | — |
| Butylated Hydroxytoluene (BHT) | 0.10 | — | 0.10 | 0.10 |
| Brij S20 | — | — | — | — |
| Tween 80 | — | — | — | — |
| Diamethicone 350 cst | — | — | — | — |
| Propylene Glycol | — | — | — | — |
| Dipropylene glycol | — | — | — | — |
| Diisopropyl adipate | — | — | 10.00 | — |
| PEG 300 | — | — | — | — |
| Oleyl alcohol | — | — | — | 5.00 |
| Total | 100.00 | 100.00 | 100.00 | 100.00 |

The results of saturated solubility studies of the formulations in Table 7 are summarized below:

Aqueous Gel Solvent Systems (A10-A14):

For Compound 1:

The solubility of Compound 1 fell as the level of Transcutol P was reduced (SSA10; 45% w/w-SSA11; 25% w/w) while maintaining 10% w/w water content.

The inclusion of propylene glycol (SSA12), dipropylene glycol (SSA13) and PEG 300 (SSA14) while reducing the water and PEG 400 content, raised the solubility of Compound 1. These three solvent systems resulted in a saturated solubility between 0.25% w/w and 0.30% w/w for Compound 1, which was marginally lower than both SSA10 (0.36% w/w) and SSA11 (0.31% w/w).

For Compound 2:

Compound 2 displayed slightly better solubility in these systems (SSA12, SSA13 and SSA14) resulting a solubility between 0.68% w/w and 0.76% w/w.

In summary, the aqueous gel solvent systems in Table 7 followed a similar trend to that observed with the solvent systems prepared in the prior Examples, whereby relatively low solubility was observed for both Compound 1 (maximum, 0.36% w/w) and Compound 2 (maximum, 0.76% w/w). The inclusion of water as observed previously reduced the solubility of both APIs.

Non-Aqueous Gel Solvent Systems (SSNA6, SSNA7, SSNA9).

The solubility Compound 1 and Compound 2 in the non-aqueous compositions of Table 7 were also assessed. SSNA6 and SSNA7 contained two different skin conditioners (Glycerol and Diisopropyl adipate), and SSNA9 contained a penetration enhancer (Oleyl Alcohol), while maintaining the levels of Transcutol P at 25% w/w. The results are summarized below:

For Compound 1, as seen in the preceding Examples, the non-aqueous gel solvent systems were found to have low API solubility, 0.21% w/w (SSNA6) and 0.19% w/w (SSNA7).

For Compound 2, similar to as seen in the preceding Examples, the non-aqueous gel solvent systems proved to have a higher API loading capacity than for Compound 1. Solubility ranged from 2.63% w/w (SSNA9) to 4.24% w/w (SNA7).

The inclusion of the lower MW PEG (300, included at the request of the Sponsor) in SSA14 did not appear to improve drug solubility.

These data show that while the systems assessed had a low API loading for Compound 1 and a higher loading for Compound 2, depending on the target concentration, a non-aqueous gel can be formulated with either Compound 1 or Compound 2.

Cream Solvent Systems (SSC3, SSC4, SSC5, SSC6, SSC8)

The solvent systems were designed with SSC1 as a base, maintaining the water level at 30% w/w in order to mitigate chemical and physical stability issues (phase separation). A solvent system with 20% w/w water and no benzyl alcohol was also assessed (SSC8).

The results are summarized below:

Varying surfactants Brij S20 (SSC3) and Tween 80 (SSC4) and skin conditioners Dimethicone 350 cst (SSC6) were included to assess the impact on solubility of both Compound 1 and Compound 2. For all these systems, Compound 1 resulted in a solubility of ≤0.15% w/w and Compound 2 resulted in a solubility of ≤0.11% w/w (SSC3 and SSC8 only).

The assessment of varying excipient levels and inclusion of other excipients such as surfactants and skin conditioners, made no significant impact to the solubility of either Compound 1 or Compound 2.

Example 8—Further Solvent Systems

A selection of formulation types (creams, PEG ointments, aqueous and non-aqueous gels) were prepared, with aqueous gels and cream formulation being the primary focus for Compound 1 (as shown in Table 8 45) and non-aqueous formulations being the focus for Compound 2 (as shown in Table 9 46):

TABLE 8

Composition (% w/w) of Additional Solvent Systems for Compound 1

| Phase | Excipient | Theoretical Composition (% w/w) | | | | | | | | |
|---|---|---|---|---|---|---|---|---|---|---|
| | | AG1 SSA3 | AG7 SSA10 | AG8 SSA11 | AG9 SSA13 | AG10 SSA14 | AG11 SSA3 | NAG3 SSNA4 | PO5 SSPO1 | CR5 SSC8 |
| Aqueous Phase | Compound 1 | 0.30 | 0.29 | 0.25 | 0.22 | 0.24 | 0.30 | 0.17 | 0.18 | 0.10 |
| | PEG400 | 41.60 | 43.71 | 63.75 | 58.68 | 34.46 | 40.85 | 63.73 | 58.72 | 43.80 |
| | Diethylene Glycol Monoethyl Ether (Transcutol ® P) | 45.00 | 45.00 | 25.00 | 25.00 | 25.00 | 45.00 | 25.00 | 15.00 | 15.00 |
| | Water | 10.00 | 10.00 | 10.00 | 5.00 | 5.00 | 10.00 | — | — | 20.00 |
| | Benzyl Alcohol | 2.00 | — | — | — | — | 2.00 | — | — | — |
| | Glycerol | — | — | — | — | — | — | 10.00 | — | — |
| | Butylated Hydroxytoluene (BHT) | 0.10 | — | — | 0.10 | 0.10 | 0.10 | 0.10 | 0.10 | 0.10 |
| | Dipropylene glycol | — | — | — | 10.00 | — | — | — | — | — |
| | PEG 300 | — | — | — | — | 34.46 | — | — | — | — |
| Oil Phase/ Surfactants | PEG 3550 | — | — | — | — | — | — | — | 25.00 | — |
| | IPM | — | — | — | — | — | — | — | — | — |
| | Cetostearyl Alcohol | — | — | — | — | — | — | — | — | 5.00 |
| | Crodamol GTCC | — | — | — | — | — | — | — | — | 10.00 |
| | Dimethicone 350 | — | — | — | — | — | 0.75 | — | — | 1.00 |
| | Brij S2 (Brj 72) | — | — | — | — | — | — | — | — | 1.898 |
| | Brj S20 | — | — | — | — | — | — | — | — | 3.11 |
| Polymers | Carbopol 980NF | 1.00 | 1.00 | 1.00 | 1.00 | 0.75 | 1.00 | — | — | — |
| | HPC-HF | — | — | — | — | — | — | 1.00 | — | — |
| | Total | 100.00 | 100.00 | 100.00 | 100.00 | 100.00 | 100.00 | 100.00 | 100.00 | 100.00 |

TABLE 9

Composition (% w/w) of Additional Solvent Systems for Compound 2

| Phase | Excipient | Theoretical Composition (% w/w) | | | | | |
|---|---|---|---|---|---|---|---|
| | | NAG3 SSNA4 | NAG5 SSNA4* | NAG6 SSNA7 | NAG7 SSNA3 | PO5 SSPO1 | CR5 SSC8 |
| Aqueous Phase | Compound 2 | 3.65 | 3.65 | 3.39 | 2.71 | 4.06 | 0.07 |
| | PEG 400 | 60.25 | 60.35 | 60.51 | 64.19 | 55.84 | 43.83 |
| | Transcutol P | 25.00 | 25.00 | 25.00 | — | 15.00 | 15.00 |
| | Water | — | — | — | — | — | 20.00 |
| | Benzyl alcohol | — | — | — | 2.00 | — | — |
| | Glycerol | 10.00 | 10.00 | — | 10.00 | — | — |
| | BHT | 0.10 | — | 0.10 | 0.10 | 0.10 | 0.10 |
| | Propylene glycol | — | — | — | 20.00 | — | — |
| | Diisopropyl adipate | — | — | 10.00 | — | — | — |
| Oil Phase/ Surfactants | PEG 3550 | — | — | — | — | 24.00 | — |
| | IPM | — | — | — | — | 1.00 | — |
| | Cetostearyl Alcohol | — | — | — | — | — | 5.00 |
| | Crodamol GTCC | — | — | — | — | — | 10.00 |
| | Dimethicone 350 | — | — | — | — | — | 1.00 |
| | Brij S2 (Brij 72) | — | — | — | — | — | 1.89 |
| | Brij S20 | — | — | — | — | — | 3.11 |
| Polymers | HPC-HF | 1.00 | 1.00 | 1.00 | 1.00 | — | — |
| | Total | 100.00 | 100.00 | 100.00 | 100.00 | 100.00 | 100.00 |

Aqueous Gel Formulations

The aqueous gels were prepared with 1% w/w of gelling agent (Carbopol 980NF). A single formulation (AG10) containing 0.75% w/w Carbopol 980NF was also prepared.

Compound 1:

- AG1, AG9, AG10 and AG11 all incorporated BHT, as the antioxidant was shown to increase the stability of the API in this excipient during the pre-formulation experiments.
- Benzyl alcohol was only included in two of the formulations (AG1 and AG11).
- Formulations were designed with water levels maintained at 10% w/w for AG1, AG7, AG8 and AG11, the water content was then dropped to 5% w/w in both AG9 and AG10 to assess the impact on drug solubility and formulation physical stability.

Aqueous gel formulations were successfully prepared and possessed desirable organoleptic properties (low viscosity). These formulations were evaluated for short-term stability as described below.

Non-Aqueous Gel Formulations

A series of non-aqueous gel formulations were designed to include various additional components, a summary of which is presented below:

- As with the non-aqueous gel formulations of the prior Examples, HPC-HF was again employed in these formulations at 1% w/w.
- NAG3 and 5 were designed to assess the antioxidant, BHT and the humectant, glycerol.
- NAG6 replaced glycerol with dipropylene glycol and NAG7 included benzyl alcohol, BHT and propylene glycol.

Non-aqueous gels were prepared utilizing the solvent systems with the greatest API loading for both Compound 1 and Compound 2, and evaluated for short-term stability (see below).

Cream Formulations

A single cream formulation based on SSC8 solvent system was prepared to evaluate the surfactants assessed in the prior Examples. This cream formulation was prepared with both Compound 1 and Compound 2, and was assessed for short term stability as discussed below.

PEG Ointment Formulations

Utilizing the solvent system SSPO1, a single ointment formulation (PO5) was prepared including PEG 3350 and IPM (isopropyl myristate; skin conditioner and penetration enhancer). This formulation assessed the addition of the lower molecular weight PEG 3350. PEG 400 in conjunction with IPM and SSPO1 had previously been prepared in formulation PO2 (Table 2). This PEG ointment formulation was prepared with both Compound 1 and Compound 2, and was assessed for short term stability as discussed below.

Example 9—Short Term Stability of Further Solvent Systems

The short term stability of the formulations prepared in Example 8 was determined, where both active and placebo formulations were assessed at T=0, T=2 weeks and T=4 weeks (25° C. and 40° C.) for the following parameters:

- API content and purity (Section 8.6.1);
- Macroscopic observations (Section 8.6.2);
- Microscopic observations (Section 8.6.3);
- Apparent pH (Section 8.6.4).

Aliquots of all formulations were also used in an sRICA efficacy assessment, discussed, below in Example 17.

The content and purity of both Compound 1 and Compound 2 formulations of Table 8 and 9 are outlined in Tables 10-13 below:

TABLE 10

Percentage recovery of Compound 1 at T = 0 and following 2 and 4 weeks storage at 25 °C and 40 °C

| | Mean percentage recovery (%) of Compound 1 (as a percentage of the theoretical concentration) | | | | |
|---|---|---|---|---|---|
| | | T = 2 weeks | | T = 4 weeks | |
| Formulation | T = 0 | 25 °C | 40 °C | 25 °C | 40 °C |
| AG1 | 98.49 | 99.98 | 99.26 | 98.36 | 98.30 |
| AG7 | 98.40 | 97.84 | 98.65 | 96.93 | 96.76 |
| AG8 | 98.18 | 98.32 | 97.31 | 96.85 | 96.27 |
| AG9 | 99.76 | 101.87 | 101.01 | 97.90 | 98.51 |
| AG10 | 98.87 | 100.45 | 100.67 | 97.19 | 97.56 |
| AG11 | 99.86 | 101.48 | 100.62 | 97.31 | 97.38 |
| NAG3 | 97.98 | 101.46 | 101.52 | 97.57 | 97.72 |
| PO5 | 98.84 | 100.48 | 101.67 | 98.48 | 97.56 |
| CR5 | 102.39 | 103.35 | 105.60 | 100.11 | 104.45 |

TABLE 11

Percentage recovery of Compound 2 at T = 0 and following 2 and 4 weeks storage at 25 °C and 40 °C

| | Mean percentage recovery (%) of Compound 2 (as a percentage of the theoretical concentration) | | | | |
|---|---|---|---|---|---|
| | | T = 2 weeks | | T = 4 weeks | |
| Formulation | T = 0 | 25 °C | 40 °C | 25 °C | 40 °C |
| NAG3 | 100.75 | 98.88 | 98.82 | 98.69 | 97.98 |
| NAG5 | 100.32 | 98.30 | 98.51 | 98.23 | 97.20 |
| NAG6 | 102.54 | 97.34 | 97.93 | 97.45 | 96.19 |
| NAG7 | 100.14 | 97.66 | 96.87 | 95.30 | 96.85 |
| PO5 | 101.79 | 98.90 | 98.88 | 98.73 | 99.59 |
| CR5 | 97.58 | 105.69 | 103.14 | 98.69 | 105.42 |

TABLE 12

Percentage peak purity (% area) of Compound 1 at T = 0 and following 2 and 4 weeks storage at 25 °C and 40 °C

| | Mean percentage recovery (%) of Compound 1 | | | | |
|---|---|---|---|---|---|
| | | T = 2 weeks | | T = 4 weeks | |
| Formulation | T = 0 | 25 °C | 40 °C | 25° C. | 40 °C |
| AG1 | 99.93 | 99.94 | 99.93 | 99.90 | 99.90 |
| AG7 | 99.93 | 99.92 | 99.91 | 99.91 | 99.50 |
| AG8 | 99.94 | 99.93 | 99.89 | 99.90 | 99.52 |
| AG9 | 99.82 | 99.13 | 99.67 | 99.89 | 99.95 |
| AG10 | 99.93 | 99.94 | 99.95 | 99.91 | 99.91 |
| AG11 | 99.93 | 99.95 | 99.96 | 99.66* | 99.94 |
| NAG3 | 95.19** | 95.34** | 95.27** | 95.16** | 95.09** |
| PO5 | 95.10** | 95.30** | 96.16** | 95.12** | 95.07** |
| CR5 | 99.94 | 99.63 | 99.52 | 99.95 | 99.94 |

*Probable contamination peak (0.79% a/a) at TR 12.3 min detected in n = 1 replicate only.

**Probable contamination peak (ca. 4.50-4.90% a/a) at TR 24.5 min detected in n = 3 replicates throughout the stability testing period.

TABLE 13

Percentage peak purity (% area) of Compound 2 at T = 0 and following 2 and 4 weeks storage at 25 °C and 40 °C

| | Mean percentage recovery (%) of Compound 2 | | | | |
|---|---|---|---|---|---|
| | | T = 2 weeks | | T = 4 weeks | |
| Formulation | T = 0 | 25 °C | 40 °C | 25 °C | 40 °C |
| NAG3 | 99.85 | 99.69 | 99.90 | 99.86 | 99.78 |
| NAG5 | 99.88 | 99.67 | 99.90 | 99.88 | 99.82 |
| NAG6 | 99.21 | 99.95 | 99.94 | 99.84 | 99.69 |
| NAG7 | 99.76 | 99.96 | 99.95 | 99.88 | 99.85 |
| PO5 | 99.88 | 99.74 | 99.87 | 99.72 | 99.67 |
| CR5 | 99.64 | 99.49 | 99.56 | 99.83 | 99.69 |

The results can be summarized as follows:

For Compound 1:

For all formulations the recovery observed during the 4 weeks stability study did not deviate by more than 3% from the T=0 result.

At T=0 the percentage recovery of T-Compound 1 in all formulations was between 97% and 103%, After 4 weeks at 40° C. the percentage recovery remained consistent ranging between 96% and 105%, no significant drop in recovery was observed.

While no obvious change in recovery was observed, for all formulations containing Compound 1 a slight downward trend in recovery was observed. The largest change in recovery was observed with AG11 where a drop of 2.48% between T=0 (99.86%) and T=4 weeks (40° C.; 97.38%).

It should be noted that for CR5, slight variability with the percentage recovery of Compound 1 was observed however no consistent trend was observed. The T=0 recovery was 102.39% whereas the T=4 week, 40° C. the recovery had risen to 104.45%. A likely explanation for this is variability in recovery efficiency from a more complex matrix system (emulsion) leading to more variable data.

The peak purity remained largely consistent over the 4 weeks stability study for all formulations at all conditions. There was a very slight decrease following storage at T=4 weeks, 40° C. for AG7 where the purity dropped from 99.93% area to 99.50% area. It should be noted that purity of ca. 95% area was observed for NAG3 and PO5 at each time point (including T=0) suggesting sample contamination (no major changes to the area of the contamination peak was seen over the stability testing period at both storage conditions).

For Compound 2:

Formulations containing Compound 2 were observed to have a more variable percentage recovery when compared to the Compound 1 formulations where the largest change was 7.84% between T=0 and T=4 weeks at 40° C. (CR5).

At T=0 the percentage recovery of Compound 2 in all formulations was between 97% and 103%, after 4 weeks at 40° C. the percentage recovery ranged between 96% and 106%.

For all formulations aside from CR5, a downward trend in recovery was observed where at the end of the 4 weeks, recovery fell by an average of 3.5%. However, there was no obvious impact of temperature which suggests that such differences may have been attributable to analytical variation.

While the recovery proved to be slightly variable, the purity of Compound 2 remained consistent throughout the 4 weeks at all conditions for all formulations.

These data suggest that chemical stability of both Compound 1 and Compound 2 was achieved at 25 and 40° C. in a number of formulations, where the purity remained consistent. The inclusion of BHT in the formulations did not make a significant difference to the recovery or purity of either API over the course of the stability assessment. For example NAG3 (with BHT) and NAG5 (without BHT) both had very similar recoveries and purities at the end of the 4 weeks at 40° C. (NAG3—recovery: 97.98% a/a, purity: 99.78%; NAG5-recovery: 97.20% a/a, purity: 99.82%).

Example 10—Macroscopic and Microscopic Observations for Compound 1 and Compound 2 in the Formulations of Table 8 and 9

The macroscopic observations for Compound 1 and Compound 2 formulations of Table 8 and 9 are outlined in Tables 14 and 15:

TABLE 14

Macroscopic appearance of placebo and active Compound 1 formulations at T = 0 and following 2 and 4 weeks storage at 25 °C and 40 °C

| | | | Macroscopic appearance of Compound 1 formulations | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 40 °C | |
| Formulation | Placebo | Active | Placebo | Active | Placebo | Active | Placebo | Active | Placebo | Active |
| AG1 | Transparent, colourless, pourable, low viscosity | Transparent, colourless, pourable, low viscosity | No obvious change from T = 0 | | | | No obvious change from T = 0 | | | |
| AG7 | Transparent, colourless, pourable, low viscosity | Transparent, colourless, pourable, low viscosity | No obvious change from T = 0 | | | | No obvious change from T = 0 | | | |
| AG8 | Transparent, colourless, pourable, low viscosity | Transparent, colourless, pourable, low viscosity | No obvious change from T = 0 | | | | No obvious change from T = 0 | | | |

TABLE 14-continued

Macroscopic appearance of placebo and active Compound 1 formulations at T = 0 and following 2 and 4 weeks storage at 25 °C and 40 °C

| | | | Macroscopic appearance of Compound 1 formulations | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 40 °C | |
| Formulation | Placebo | Active | Placebo | Active | Placebo | Active | Placebo | Active | Placebo | Active |
| AG9 | Transparent, colourless, pourable, low viscosity | Transparent, colourless, pourable, low viscosity | No obvious change from T = 0 | | | | No obvious change from T = 0 | | | |
| AG10 | Transparent, colourless, pourable, low viscosity | Transparent, colourless, pourable, low viscosity | No obvious change from T = 0 | | | | No obvious change from T = 0 | | | |
| AG11 | Transparent, colourless, pourable, low viscosity | Transparent, colourless, pourable, low viscosity | No obvious change from T = 0 | | | | No obvious change from T = 0 | | | |
| NAG3 | Transparent, colourless, pourable, medium viscosity, stringy | Transparent, colourless, non-pourable, high viscosity, stringy | No obvious change from T = 0 | | | Visual viscosity change to medium | No obvious change from T = 0 | Visual viscosity change to medium | No obvious change from T = 0 | No obvious change from T = 2 weeks |
| PO5 | White, opaque, smooth application, non-pourable | White, opaque, smooth application, non-pourable | No obvious change from T = 0 | | | | No obvious change from T = 0 | | | |
| CR5 | Off-white, opaque, smooth application, non-pourable, high viscosity | Off-white, opaque, smooth application, non-pourable, high viscosity | No obvious change from T = 0 | | | | No obvious change from T = 0 | | | |

TABLE 15

Macroscopic appearance of placebo and active Compound 2 formulations at T = 0 and following 2 and 4 weeks storage at 25 °C and 40 °C

| | | | Macroscopic appearance of Compound 1 formulations | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 40 °C | |
| Formulation | Placebo | Active | Placebo | Active | Placebo | Active | Placebo | Active | Placebo | Active |
| NAG3 | Transparent, colourless, pourable, medium viscosity, stringy | Transparent, slight yellow tint, pourable, medium viscosity, stringy | No obvious change from T = 0 | | | | No obvious change from T = 0 | | | |
| NAG5 | Transparent, colourless, pourable, medium viscosity, stringy | Transparent, slight yellow tint, pourable, medium viscosity, stringy | No obvious change from T = 0 | | | | No obvious change from T = 0 | | | |
| NAG6 | Transparent, colourless, pourable, medium viscosity | Transparent, slight yellow tint, pourable, medium viscosity | No obvious change from T = 0 | | | | No obvious change from T = 0 | | | |

TABLE 15-continued

Macroscopic appearance of placebo and active Compound 2 formulations at T = 0 and following 2 and 4 weeks storage at 25 °C and 40 °C

| | | | Macroscopic appearance of Compound 1 formulations | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 40 °C | |
| Formulation | Placebo | Active | Placebo | Active | Placebo | Active | Placebo | Active | Placebo | Active |
| NAG7 | Transparent, colourless, non-pourable, high viscosity, stringy | Transparent, slight yellow tint, pourable, medium viscosity, stringy | No obvious change from T = 0 | | | Visual viscosity change from medium to high | No obvious change from T = 0 | | | No obvious change from T = 2 weeks |
| PO5 | White, opaque, smooth application, non-pourable | White, opaque, smooth application, non-pourable | No obvious change from T = 0 | | | | No obvious change from T = 0 | | | |
| CR5 | Off-white, opaque, smooth application, non-pourable, high viscosity | Off-white, opaque, smooth application, non-pourable, high viscosity | No obvious change from T = 0 | | | | No obvious change from T = 0 | | | |

The results can be summarized as follows:

The aqueous gel formulations (active and placebo) containing Compound 1 were observed to be transparent, colourless, low viscosity pourable gels at T=0 and this was maintained through the 4 weeks of stability testing at both 25° C. and 40° C. While displaying the majority of the macroscopic properties as the other aqueous gel formulations, AG11 was observed to be turbid from T=0 and throughout the stability testing.

The non-aqueous placebo formulations were observed to be transparent, colourless, pourable, medium viscosity with the inherent stringy appearance typically observed for HPC gels at T=0 and this was maintained through the 4 weeks of stability testing at both 25° C. and 40° C.

The non-aqueous active formulations containing Compound 1 was observed to be a transparent, colourless, non-pourable, stringy high viscosity gel at T=0. However, following 2 and 4 weeks at 40° C. the viscosity was observed as medium viscosity rather than the high viscosity observed at T=0.

The non-aqueous active formulations containing Compound 2 was observed to be transparent, slightly yellow, pourable, medium viscosity and stringy at T=0 and this was maintained through all subsequent timepoints for NAG3, 5 and 6. The viscosity for NAG7 however, was observed to become higher following the 2 and 4 week storage at 40° C.

The PO5 formulations (active and placebo) for each of Compound 1 and Compound 2 were observed to be white, opaque, smooth, non-pourable ointments at T=0 and this was maintained through the 4 weeks of stability testing at both 25° C. and 40° C.

The CR5 formulations (active and placebo) for each of Compound 1 and Compound 2 were observed to be off-white, opaque, smooth, non-pourable and high viscosity creams at T=0 and this was maintained through the 4 weeks of stability testing at both 25° C. and 40° C.

It should also be noted that the viscosity measurements were performed visually based on the pourability of the formulation, as such are subjective measurements of the viscosity. The results do however suggest that the formulations appear physically stable.

Microscopic Observations

The microscopic observations for Compound 1 and Compound 2 formulations of Table 8 and 9 are summarized below.

The aqueous gel formulations (active and placebo) containing Compound 1 were observed to be free from API crystals at T=0 and this was maintained through the 4 weeks of stability testing at both 25° C. and 40° C.

AG11 (active and placebo) however was observed to have widespread droplets at T=0 and this was observed at every subsequent timepoint, such droplets were attributed to the dimethicone present in the AG11 formulation.

The non-aqueous formulations (active and placebo) for both Compound 1 and Compound 2 were observed to be free from API crystals at all timepoint throughout the stability testing.

While no API crystals were observed at any timepoint for the PO5 formulation (for both Compound 1 and Compound 2), PEG crystals (typical of this type of formulation) were observed from T=0 and throughout the stability testing.

The CR5 formulation for both Compound 1 and Compound 2 was also observed to have no API crystals throughout the stability testing, however medium/irregular sized droplets were observed from T=0 which are typical of this type of cream formulation. Following storage at and 40° C. for 4 weeks, excipient crystals were observed in both the active and placebo prototypes, which were attributed to stearic acid (from cetostearyl alcohol). These crystals often appear during the rapid cooling of the oil phases during manufacture.

These data suggests that physical stability of both Compound 1 and Compound 2 was achieved in the formulations tested.

Example 11—Apparent pH for Compound 1 and Compound 2 in the Formulations of Table 8 and 9

The apparent pH was assessed on the aqueous gel formulations containing Compound 1. For all formulations at T=0 both the active and placebo prototypes were within 0.5 pH units of each other, this remained the case throughout. The pH of the placebo formulations ranged between pH 5.9 to pH 6.05 at T=0 and following storage for 4 weeks at 40° C. they ranged from pH 5.83 to pH 6.17. A similar trend was observed with the active formulations, where at T=0 the pH ranged from pH 5.86 to pH 6.17 and at T=4 weeks (40° C.) the pH ranged between pH 5.83 to pH 6.20. Overall, for both the active and placebo AG 1, 7 and 8 formulations there was a slight downward trend where the pH decreased over the 4 weeks stability testing, whereas the AG9, 10 and 11 formulations all displayed consistent pH throughout the 4 weeks stability testing.

Example 12—Further Solvent Systems

The following further solvent systems that could be utilized in a variety of formulation types were also prepared (Table 16):

observed as with the previous formulations. The solubility ranged from 0.09% (SSAG21) to 0.36% (SSAG15), as expected the systems with high Transcutol P content and/or no glycerol resulted in the highest solubility of Compound 1.

Systems 15, 18 and 19 all without glycerol but ranging levels of Transcutol P, water and PEG 400 resulted in solubility levels of 0.36%, 0.35% and 0.31% respectively. While glycerol was included to improve the aesthetic properties of the gel, it was observed to have a negative impact on the solubility of Compound 1, where systems including glycerol had a maximum solubility of 0.26%.

Non-Aqueous Gel Solvent Systems

The solubility of both Compound 1 and Compound 2 was assessed in the non-aqueous gel solvent systems. The inclusion of IPM was assessed in SSNA10 to assess impact on formulation aesthetics and its potential to be incorporated into a formulation as a penetration enhancer. Glycerol and propylene glycol, both at 20% w/w were included in SSNA12 while lowering the PEG400 content to approx. 15%. Diisopropyl adipate was also included in the non-aqueous gels as a skin conditioner and potential penetration enhancer to confirm physical stability and the impact on drug solubility.

As expected, the solubility of Compound 1 remained low in the non-aqueous gel solvent systems, where a maximum solubility of 0.19% in SSNA10 was observed. This is consistent with what was observed in the previous Examples.

Previously it was observed that the solubility of Compound 2 in the non-aqueous gel solvent systems was good

TABLE 16

| | Solvent systems compositions (% w/w) | | | | | | | | | | | |
|---|---|---|---|---|---|---|---|---|---|---|---|---|
| Excipient | SSA15 | SSA16 | SSA17 | SSA18 | SSA19 | SSA20 | SSA21 | SSC9 | SSC11 | SSNA10 | SSNA11 | SSNA12 |
| PEG400 | 44.70 | 32.90 | 53.90 | 37.90 | 57.90 | 44.90 | 24.90 | 22.90 | 24.70 | 59.90 | 69.90 | 14.90 |
| Transcutol P | 45.00 | 45.00 | 25.00 | 45.00 | 25.00 | 25.00 | 25.00 | 15.00 | 15.00 | 25.00 | 10.00 | 25.00 |
| Water | 10.00 | 10.00 | 10.00 | 10.00 | 10.00 | 10.00 | 10.00 | 20.00 | 20.00 | — | — | — |
| Benzyl Alcohol | — | 2.00 | — | 2.00 | 2.00 | — | — | 2.00 | — | — | — | — |
| Benzalkonium chloride | 0.20 | — | — | — | — | — | — | — | — | — | — | — |
| Phenoxyethanol | — | — | 1.00 | — | — | — | — | — | 1.00 | — | — | — |
| Glycerol | — | 10.00 | 10.00 | — | — | 15.00 | 20.00 | 20.00 | 20.00 | — | — | 20.00 |
| BHT | 0.10 | 0.10 | 0.10 | — | — | — | 0.10 | 0.10 | 0.10 | 0.10 | — | 0.10 |
| Propylene glycol | — | — | — | — | — | — | 20.00 | — | — | — | — | 20.00 |
| Dipropylene glycol | — | — | — | — | — | — | — | — | — | — | — | — |
| Diisopropyl adipate | — | — | — | 5.00 | 5.00 | 5.00 | — | — | — | 10.00 | 20.00 | 20.00 |
| Isopropyl myristate | — | — | — | — | — | — | — | — | — | 5.00 | — | — |
| Total | 100.00 | 100.00 | 100.00 | 100.00 | 100.00 | 100.00 | 100.00 | 80.00 | 80.80 | 100.00 | 100.00 | 100.00 |

Saturated solubility experiments were performed with both Compound 1 and Compound 2.

Aqueous Gel Solvent Systems

The impact of different preservatives benzalkonium chloride, benzyl alcohol and phenoxyethanol was assessed in SSA15, SSA16 and SSA17, respectively. To mitigate the greasy feel of the aqueous gels (caused by the high PEG 400 content), the inclusion of glycerol to reduce the PEG 400 content was assessed in SSAG16 and SSAG21. Glycerol was also included in SSAG17 and SSAG 20 in place of Transcutol P. The water content was maintained at 10% w/w to maintain a balance between API solubility and the necessary aesthetic properties of the gel to allow inclusion of a polymer other than HPC (which is needed to maintain physical stability in non-aqueous gel systems).

Saturated solubility in the aqueous gel solvent systems was assessed for Compound 1, where a similar trend was (approx. 2-5%), however the inclusion of diisopropyl adipate greatly reduced the drug solubility to between 0.60 and 0.78% w/w for both SSNA11 and SSNA12 suggesting that the addition of diisopropyl adipate in SSNA11 and diisopropyl adipate/propylene glycol/glycerol in SSNA12 greatly impacted the solubility of T-3774394.

Cream Solvent Systems

The solubility of both Compound 1 and Compound 2 was assessed in the cream solvent systems. Both SSC9 and 11 included glycerol at 20% w/w in a bid to improve the aesthetic properties of the resulting cream. The inclusion of the preservatives benzyl alcohol or phenoxyethanol as the preservative system was assessed in SSC9 and SSC11 respectively. The same trend of drug solubility in cream systems was observed where low solubility in the cream solvent systems for both Compound 1 and Compound 2 was evident. The inclusion of glycerol, also had a detrimental effect on the solubility of both APIs to where values ≤0.07% were observed.

Example 13—Further Formulations

Table 17 shows the composition of AG11 and NAG6 which were used as the basis further placebo formulations to assess various factors leading to improved stability, aesthetic qualities and optimization of excipient levels. The formulations are shown in Table 18.

TABLE 17

| Theoretical composition (% w/w) of active formulations containing Compound 1 and Compound 2 | | | |
|---|---|---|---|
| Phase | Excipient | Theoretical composition (% w/w) of Compound 1 active formulations AG11 SSA3 | Theoretical composition (% w/w) of Compound 2active formulations NAG6 SSNA7 |
| Aqueous Phase | Compound 1 | 0.30 | 3.39 |
| | PEG 400 | 40.85 | 60.51 |
| | Transcutol P | 45.00 | 25.00 |
| | Water | 10.00 | — |
| | Benzyl alcohol | 2.00 | — |
| | Glycerol | — | — |
| | BHT | 0.10 | 0.10 |
| | Dipropylene glycol | — | — |
| | PEG 300 | — | 10.00 |
| Oil Phase/ Surfactants | PEG 3550 | — | — |
| | IPM | — | — |
| | Cetostearyl Alcohol | — | 1 |
| | Crodamol GTCC | — | — |
| | Dimethicone 350 | 0.75 | — |
| | Brij S2 | — | — |
| | Brij S20 | — | — |
| Polymers | Carbopol 980NF | 1.00 | — |
| | HPC-HF | — | — |
| | Total | 100.00 | 100.00 |

TABLE 18

Theoretical composition (% w/w) of placebo aqueous gel formulations

| | | Theoretical composition (% w/w) of placebo aqueous gel formulations | | | | | | | |
|---|---|---|---|---|---|---|---|---|---|
| Phase | Excipient | AG11 SSA3 | AG12 SSA3 | AG13 SSA3 | AG15 SSA3 | AG16 SSA3 | AG17 SSA18 | AG18 SSA18 | AG19 SSA18 |
| | PEG 400 | 41.15 | 41.40 | 41.15 | 38.15 | 38.15 | 36.90 | 36.90 | 35.40 |
| | Transcutol P | 45.00 | 45.00 | 45.00 | 45.00 | 45.00 | 45.00 | 45.00 | 45.00 |
| | Water | 10.00 | 10.00 | 10.00 | 10.00 | 10.00 | 10.00 | 10.00 | 10.00 |
| | Benzyl alcohol | 2.00 | 2.00 | 2.00 | 2.00 | 2.00 | 2.00 | 2.00 | 2.00 |
| | BHT | 0.10 | 0.10 | 0.10 | 0.10 | 0.10 | 0.10 | 0.10 | 0.10 |
| | Etocas 35 | — | — | — | 3.00 | — | — | — | — |
| | Dimethicone 350 | 0.75 | 0.50 | 0.75 | 0.75 | — | — | — | — |
| | Cyclomethicone 5-NF | — | — | — | — | 3.00 | — | — | — |
| | Diisopropyl adipate | — | — | — | — | — | 5.00 | 5.00 | 5.00 |
| Polymers | Carbopol 980NF | 1.00 | 1.00 | 1.00 | 1.00 | 1.00 | 1.00 | — | — |
| | HPC-JF | — | — | — | — | — | — | 1.00 | — |
| | Sapineo 600 | — | — | — | — | — | — | — | 2.50 |
| Total | | 100.00 | 100.00 | 100.00 | 100.00 | 100.00 | 100.00 | 100.00 | 100.00 |

| | | Theoretical composition (% w/w) of placebo aqueous gel formulations | | | | | | | | |
|---|---|---|---|---|---|---|---|---|---|---|
| Phase | Excipient | AG20 SSA18 | AG21 SSA18 | AG22 SSA18 | AG23 SSA18 | AG24 SSA18 | AG25 SSA18 | AG26 SSA19 | AG27 SSA19 | AG28 SSA19 |
| | PEG 400 | 36.90 | 35.90 | 33.40 | 33.90 | 34.90 | 36.90 | 54.90 | 54.90 | 56.40 |
| | Transcutol P | 45.00 | 45.00 | 45.00 | 45.00 | 15.00 | 45.00 | 25.00 | 25.00 | 25.00 |
| | Water | 10.00 | 10.00 | 10.00 | 10.00 | 10.00 | 10.00 | 10.00 | 10.00 | 10.00 |
| | Benzyl alcohol | 2.00 | 2.00 | 2.00 | 2.00 | 2.00 | 2.00 | 2.00 | 2.00 | 2.00 |
| | BHT | 0.10 | 0.10 | 0.10 | 0.10 | 0.10 | 0.10 | 0.10 | 0.10 | 0.10 |
| | Etocas 35 | — | — | — | — | — | — | — | — | — |
| | Dimethicone 350 | — | — | — | — | — | — | — | — | — |
| | Cyclomethicone 5-NF | — | — | — | — | — | — | — | — | — |
| | Diisopropyl adipate | 5.00 | 5.00 | 5.00 | 5.00 | 5.00 | 5.00 | 5.00 | 5.00 | 5.00 |
| Polymers | Carbopol 980NF | 1.00 | — | — | — | — | — | — | — | — |
| | HPC-HF | — | — | — | — | — | 1.00 | — | — | 1.50 |
| | HPC-JF | — | 2.00 | — | 4.00 | — | — | — | 3.00 | — |
| | HPC-MF | — | — | — | — | 3.00 | — | 3.00 | — | — |
| | Sapineo 600 | — | — | 4.50 | — | — | — | — | — | — |
| pH adjustment | | 6-6.5 | — | — | — | — | — | — | — | — |
| Total | | 100.00 | 100.00 | 100.00 | 100.00 | 100.00 | 100.00 | 100.00 | 100.00 | 100.00 |

Aqueous Gel Formulations

Utilizing AG11 as a base for all the aqueous gel formulations, the following modifications were made and assessed:

The turbidity of AG11 was investigated, utilizing SSA3/AG11 as a base and various approaches were assessed (Table 61) as below.

In order to reduce the turbidity of the aqueous gels, the dimethicone 350 content was lowered to 0.5% in AG12, however the formulation remained turbid. The manufacturing process was altered in AG13 to reduce the turbidity. The order in which the excipients were originally combined in AG.11, was altered to the following:

1. Dimethicone 350+PEG400+TransP, resulted in a turbid gel with oily droplets.
2. Dimethicone+TransP+PEG400, resulted in a less turbid gel however the gel remained turbid.

The inclusion of a surfactant to reduce the turbidity was assessed in AG15, where Etocas 35 was included along with dimethicone 350, however the gel remained turbid. The inclusion Cyclomethicone 5-NF in place of dimethicone was assessed in AG16, however this had no beneficial impact on the turbidity of the gel as it remained turbid.

Different gelling agents were evaluated utilizing SSA18 and SSA19 as the solvent system base, to assess the turbidity and viscosity of the resulting formulations (Table 61).

Diisopropyl adipate and Carbopol 980NF (1% w/w) were included in SSA18 where the resultant formulation AG17 appeared slightly turbid and slightly oily, with a low viscosity (pourable). Diisopropyl adipate and HPC-JF (1% w/w) were included in SSA18 where the resultant formulation AG18 appeared to be very low viscosity (easily pourable) and transparent. Diisopropyl adipate and Sapineo 600 (2.5% w/w) were included in SSA18 where the resultant formulation AG19 appeared to be very low viscosity (easily pourable) and Turbid. AG17 was then re-prepared including a pH adjustment step (target pH 6-6.5), this resulted in a transparent, medium viscosity gel (AG20). AG18 was re-developed twice raising the HPC-JF content to 2% w/w then 4% w/w to produce a higher viscosity gel (AG21 & AG23). However, both formulations while remaining transparent, were still observed to be low in viscosity. AG19 was re-developed raising the Sapineo 600 content from 2.5% w/w to 4.5% w/w however the resultant formulation (AG22) remained low in viscosity and turbid. HPC-HF and HPC-MF were assessed in AG24 and AG25 respectively, however the resultant formulations were both observed to be colourless, slightly turbid and medium viscosity (pourable). SSA19 was also assessed in combination with three gelling agents, HPC-HF, HPC-JF and HPC-MF resulting the AG26, AG27 and AG28 respectively. AG26 and AG28 were colourless, slightly turbid and high viscosity (non-pourable). AG27 on the other hand was clear, colourless and low viscosity (pourable).

Non-Aqueous Gel Formulations

Building upon NAG6, the non-aqueous gel formulations were designed to assess different gelling agents, the inclusion of IPM, glycerol and propylene glycol. The compositions of the non-aqueous gel formulations are detailed in Table 19:

TABLE 19

Theoretical composition (% w/w) of placebo non-aqueous gel formulations

| | | Theoretical composition (% w/w) of placebo non-aqueous gel formulations | | | | | | |
|---|---|---|---|---|---|---|---|---|
| Phase | Excipient | NAG6 SSNA7 | NAG8 SSNA7 | NAG9 SSNA11 | NAG10 SSNA7 | NAG11 SSNA11 | NAG12 SSNA12 | NAG13 SSNA10 |
| | PEG 400 | 63.90 | 63.90 | 68.90 | 60.90 | 68.90 | 13.90 | 58.90 |
| | Transcutol P | 25.00 | 25.00 | 10.00 | 25.00 | 10.00 | 25.00 | 25.00 |
| | BHT | 0.10 | 0.10 | 0.10 | 0.10 | 0.10 | 0.10 | 0.10 |
| | Diisopropyl adipate | 10.00 | 10.00 | 20.00 | 10.00 | 20.00 | 20.00 | 10.00 |
| | Glycerol | — | — | — | — | — | 18.50 | — |
| | Propylene glycol | — | — | — | — | — | 20.00 | — |
| | Isopropyl myristate | — | — | — | — | — | — | 5.00 |
| Polymers | HPC-HF | 1.00 | — | — | — | 1.00 | — | 1.00 |
| | HPC-JF | — | 1.00 | 1.00 | 4.00 | — | 2.50 | — |
| Total | | 100.00 | 100.00 | 100.00 | 100.00 | 100.00 | 100.00 | 100.00 |

NAG8 and NAG10 both incorporated the alternate gelling agent HPC-JF at 1% and 4% w/w respectively. HPC-JF at 1% w/w, the formulation remained transparent and was observed to be very low in viscosity (pourable). At 4% w/w, the formulation remained transparent, but the was observed to be of medium viscosity (pourable).

NAG9 and NAG11 both included diisopropyl adipate (skin conditioner) and lowered the Transcutol P content, however differed in the gelling agents employed, HPC-JF was used in NAG9 and HPC-HF was used in NAG11. NAG9 was observed to be transparent and of, very low viscosity (pourable) where as NAG11 was observed to be colourless, slightly turbid, and of medium viscosity (pourable).

NAG12 was designed to include the skin conditioners diisopropyl adipate and glycerol and the penetration enhancer propylene glycol. NAG12 also included HPC-JF at 2.5% w/w, which resulted in a transparent, low viscosity (pourable gel).

NAG13 included the skin conditioner IPM in place of IPP, initially formulations including IPP were observed to be oily, a trait undesired by the sponsor. Thus, IPM was incorporated into the formulation which resulted in colourless, slightly turbid, medium viscosity (pourable) gel however it was observed to be slightly oily.

Cream Formulations

The cream formulations were assessed in addition to both the aqueous and non-aqueous gels developed. CR5 (SSC8) was utilized as the starting point for the development of the creams discussed below. The compositions of the cream formulations assessed are detailed in Table 20 below:

TABLE 20

Theoretical composition (% w/w) of placebo cream formulations

| Phase | Excipient | CR5 SSC8 | CR6 SSC9 | CR7 SSC9 | CR8 SSC8 | CR9 SSC8 |
|---|---|---|---|---|---|---|
| Aqueous Phase | PEG 400 | 43.90 | 22.90 | 21.90 | 47.71 | 44.90 |
| | Transcutol P | 15.00 | 15.00 | 15.00 | 15.94 | 15.00 |
| | Water | 20.00 | 20.00 | 20.00 | 21.25 | 20.00 |
| | Benzyl alcohol | — | 2.00 | 2.00 | — | — |
| | Glycerol | — | 20.00 | 20.00 | — | — |
| | BHT | 0.10 | 0.10 | 0.10 | 0.11 | 0.10 |
| Oil Phase/ Surfactants | Diispropyl adipate | — | — | — | — | 9.00 |
| | Cetyl alcohol | — | 5.00 | 5.00 | — | — |
| | Liquid paraffin | — | 10.00 | 10.00 | — | — |
| | Etocas 35 | — | 4.72 | 4.72 | — | — |
| | Glycerol Monostearate (Kolliwax GMS type II) | — | 0.28 | 0.28 | — | — |
| | Dimethicone 350 | 1.00 | — | 1.00 | 1.00 | 1.00 |
| | Cetostearyl Alcohol | 5.00 | — | — | 2.50 | 5.00 |
| | Crodamol GTCC | 10.00 | — | — | 6.50 | — |
| | Brij S2 | 1.89 | — | — | 2.28 | 2.14 |
| | Brij S20 | 3.11 | — | — | 2.72 | 2.86 |
| Total | | 100.00 | 100.00 | 100.00 | 100.00 | 100.00 |

Theoretical composition (% w/w) of placebo cream formulations

| Phase | Excipient | CR10 SSC8 | CR11 SSC8 | CR12 SSC8 | CR13 SSC8 | CR14 SSC8 |
|---|---|---|---|---|---|---|
| Aqueous Phase | PEG 400 | 44.90 | 44.90 | 44.90 | 43.90 | 43.90 |
| | Transcutol P | 15.00 | 15.00 | 15.00 | 15.00 | 15.00 |
| | Water | 20.00 | 20.00 | 20.00 | 20.00 | 20.00 |
| | BHT | 0.10 | 0.10 | 0.10 | 0.10 | 0.10 |
| Oil Phase/ Surfactants | Diispropyl adipate | 4.50 | 4.50 | — | — | — |
| | Isopropyl myristate | — | 4.50 | 4.50 | — | — |
| | Dimethicone 350 | 1.00 | 1.00 | 1.00 | 1.00 | 1.00 |
| | Cetostearyl Alcohol | 5.00 | 5.00 | 5.00 | 2.00 | 2.00 |
| | Crodamol GTCC | 4.50 | — | 4.50 | 13.00 | — |
| | Cyclomethicone 5NF | — | — | — | — | 13.00 |
| | Brij S2 | 1.99 | — | — | 2.39 | 3.38 |
| | Brij S20 | 3.01 | — | — | 2.61 | 1.62 |
| | Span 60 | — | 1.63 | 1.48 | — | — |
| | Tween 80 | — | 3.37 | 3.52 | — | — |
| Total | | 100.00 | 100.00 | 100.00 | 100.00 | 100.00 |
| Comments | | Formulation similar to CR9, but containing equal amount of GTCC and DIPA | Alternative oil phase (inclusion of DIPA, IPM, Span 60 and Tween 80) | Alternative oil phase (inclusion of IPM, Span 60 and Tween 80) | Formulation similar to CR5, but high content of GTCC | Alternative oil phase (inclusion of cyclomethicone) |
| Observations | | Off-white cream, high viscosity, smooth application, greasy; phase separation after 18 min centrifugation. | Off-white cream, high viscosity, smooth application, slightly greasy, phase separation. | Off-white cream, high viscosity, smooth application, greasy; phase separation. | Off-white cream, high viscosity, smooth application, greasy, phase separation after 20 min centrifugation. | Off-white cream, medium viscosity, smooth application, slightly greasy; phase separation after 2 min centrifugation. |

CR6 and CR7 both based on SSC9 includes an oil phase that differ from the original CR5, CR7 also includes the skin conditioner Dimethicone 350. Both formulations were observed to be white in appearance, medium viscosity (non-pourable) creams, which phase separated after 2 minutes of centrifugation. It was noted however that the CR7 was visibly more viscous that the CR6.

CR8, CR9 and CR10 are all based on CR5, CR8 was developed with 15% oil phase (originally 20%), CR9 was developed with diisopropyl adipate in place of GTCC and CR10 was developed with equal parts diisopropyl adipate and GTCC. All three formulations were observed to have the same macroscopic properties: Off-white, high viscosity cream and slightly greasy. The formulations differed during the accelerated stability via centrifugation where CR8 and CR10 (both including GTCC) saw phase separation after 20 and 18 minutes respectively, whereas CR9 phase separated after 2 minutes of centrifugation.

CR11, CR12, CR13 and CR14 all employed the same aqueous phase however varied the oil phase composition in comparison to CR5. Both CR11 and CR12 included IPM, Span 60 and Tween 80, with diisopropyl adipate also being present in CR11. CR13 contained 13% w/w GTCC compared to the 10% found in CR5 and CR14 included cyclomethicone-5NF. All four of the formulations were observed to be off-white in appearance and slightly greasy. CR14 was the only formulation observed to be of medium viscosity, all others were of high viscosity. During accelerated stability, all four formulations phase separated, with those containing higher GTCC content surviving longer centrifugation periods before phase separating.

Example 14—Short-Term Formulation Stability

The formulations shown in Table 64 and Table 65 were prepared and their short term stability was assessed.

The formulations for Compound 1 (shown in Table 21) were as follows: AG1 (which was assessed previously), AG11 (similar to AG1 however contains dimethicone 350), AG 20/23 (based on SSA18, containing different gelling agents), AG29 (based on SSA19 with reduced levels of Transcutol P), NAG6 (based on SSNA7 with lower level of Transcutol P) and CR8/14 (based on SSC8 with reduced oil phase and containing cyclomethicone, respectively).

For Compound 2 (shown in Table 22), the following non-aqueous gels were selected: NAG6 (was assessed previously in addition to the same formulation with reduced drug level: 0.5% w/w Compound 2), NAG10 (similar to NAG6 but containing alternative gelling agent) and NAG14 (based on SSNA12 containing glycerol and propylene glycol), AG11 (based on SSA3), CR8 (reduced amount of oil phase) and CR14 (containing cyclomethicone) were also selected for Compound 2.

TABLE 21

Theoretical composition (% w/w) of active formulations containing Compound 1

| | | Theoretical composition (% w/w) of Compound 1 active formulations | | | | | | | |
|---|---|---|---|---|---|---|---|---|---|
| Phase | Excipient | AG1-Cpd1 SSA3 | AG11-Cpd1 SSA3 | AG20 SSA18 | AG23 SSA18 | AG29 SSA19 | NAG8-Cpd1 SSNA7 | CR8-Cpd1 SSC8 | CR14-Cpd1 SSC8 |
| Aqueous Phase | Compound 1 | 0.30 | 0.30 | 0.28 | 0.28 | 0.25 | 0.15 | 0.10 | 0.10 |
| | PEG 400 | 41.60 | 40.85 | 36.62 | 33.62 | 53.65 | 63.73 | 45.61 | 41.80 |
| | Transculol P | 48.00 | 48.00 | 45.00 | 45.00 | 25.00 | 25.00 | 15.94 | 15.00 |
| | Water | 10.00 | 10.00 | 10.00 | 10.00 | 10.00 | — | 21.25 | 20.00 |
| | Benzyl alcohol | 2.00 | 2.00 | 2.00 | 2.00 | 2.00 | — | 2.00 | 2.00 |
| | Glycerol | — | — | — | — | — | — | — | — |
| | BHT | 0.10 | 0.10 | 0.10 | 0.10 | 0.10 | 0.10 | 0.10 | 0.10 |
| | Propylene glycol | — | — | — | — | — | — | — | — |
| | Diisopropyl adipate | — | — | 5.00 | 5.00 | 5.00 | 10.00 | — | — |
| Oil phase/ Surfactants | Cetostearyl Alcohol | — | — | — | — | — | — | 2.50 | 2.00 |
| | Crodamol GTCC | — | — | — | — | — | — | 5.50 | — |
| | Dimethicone 350 | — | 0.75 | — | — | — | — | 1.00 | 1.00 |
| | Cyclomethicone 5NF | — | — | — | — | — | — | — | 13.00 |
| | Brij S2 (Brij 72) | — | — | — | — | — | — | 2.28 | 3.38 |
| | Brij S20 | — | — | — | — | — | — | 2.72 | 1.62 |
| Polymers | Carbopol 980NF | 1.00 | 1.00 | 1.00 | — | — | — | — | — |
| | HPC-JF | — | — | — | 4.00 | 4.00 | — | — | — |
| | HPC-HF | — | — | — | — | — | 1.00 | — | — |
| | Total | 100.00 | 100.00 | 1000.00 | 100.00 | 100.00 | 100.00 | 100.00 | 100.00 |

TABLE 22

Theoretical composition (% w/w) of active formulations containing Compound 2

| | | Theoretical composition (% w/w) of Compound 2 active formulations | | | | | | |
|---|---|---|---|---|---|---|---|---|
| Phase | Excipient | NAG6-Cpd2 SSNA7 | NAG6-Cpd2 (0.5%) SSNA7 | NAG10 SSNA7 | NAG14 SSNA12 | AG11-Cpd2 SSA3 | CR8-Cpd2 SSC8 | CR14-Cpd2 SSC8 |
| Aqueous Phase | Compound 2 | 3.39 | 0.50 | 3.39 | 0.48 | 0.39 | 0.07 | 0.07 |
| | PEG 400 | 60.51 | 63.40 | 57.51 | 13.42 | 40.76 | 45.64 | 41.83 |
| | Transcutol P | 25.00 | 25.00 | 25.00 | 25.00 | 45.00 | 15.94 | 15.00 |
| | Water | — | — | — | — | 10.00 | 21.25 | 20.00 |
| | Benzyl alcohol | — | — | — | — | 2.00 | 2.00 | 2.00 |
| | Glycerol | — | — | — | 19.00 | — | — | — |
| | BHT | 0.10 | 0.10 | 0.10 | 0.10 | 0.10 | 0.10 | 0.10 |
| | Propylene glycol | — | — | — | 19.00 | — | — | — |
| | Diisopropyl adipate | 10.00 | 10.00 | 10.00 | 19.00 | — | — | — |
| Oil phase/ Surfactants | Cetostearyl Alcohol | — | — | — | — | — | 2.50 | 2.00 |
| | Crodamol GTCC | — | — | — | — | — | 6.50 | — |
| | Dimethicone 350 | — | — | — | — | 0.75 | 1.00 | 1.00 |
| | Cyclomethicone 5NF | — | — | — | — | — | — | 13.00 |
| | Brij S2 (Brij 72) | — | — | — | — | — | 2.28 | 3.38 |
| | Brij S20 | — | — | — | — | — | 2.72 | 1.62 |
| Polymers | Carbopol 980NF | — | — | — | — | 1.00 | — | — |
| | HPC-JF | — | — | 4.00 | 4.00 | — | — | — |
| | HPC-HF | 1.00 | 1.00 | — | — | — | — | — |
| Total | | 100.00 | 100.00 | 100.00 | 100.00 | 100.00 | 100.00 | 100.00 |

The content and purity of Compound 1 and Compound 2 in the formulations of Tables 64 and 65 are shown in Tables 23-25.

TABLE 23

Percentage recovery of Compound 1, presented as a percentage of the theoretical concentration, in Compound 1 active formulations at T = 0 and following 2 and 4 weeks storage at 25 °C and 40 °C

| | Mean percentage recovery (%) of Compound 1 | | | | |
|---|---|---|---|---|---|
| | | T = 2 weeks | | T = 4 weeks | |
| Formulation | T = 0 | 25 °C | 40 °C | 25 °C | 40 °C |
| AG1-Compound 1 | 98.49 | 99.98 | 99.26 | 98.36 | 98.30 |
| AG11-Compound 1 | 99.88 | 101.48 | 100.62 | 97.31 | 97.38 |
| AG20 | 98.43 | 98.74 | 98.03 | 96.79 | 97.09 |
| AG23 | 99.17 | 99.67 | 99.88 | 97.87 | 97.75 |
| AG29 | 99.24 | 100.43 | 98.61 | 97.82 | 97.60 |
| NAG6-Compound 1 | 100.75 | 100.33 | 101.30 | 97.61 | 98.64 |
| CR8-Compound 1 | 101.71 | 100.95 | 100.78 | 98.53 | 108.72 |
| CR14-Compound 1 | 105.32= | 104.71 | 109.40 | 100.10 | 105.82 |

TABLE 24

Percentage recovery of Compound 2, presented as a percentage of the theoretical concentration, in Compound 2 active formulations at T = 0 and following 2 and 4 weeks storage at 25 °C and 40 °C

| | Mean percentage recovery (%) of Compound 2 | | | | |
|---|---|---|---|---|---|
| | | T = 2 weeks | | T = 4 weeks | |
| Formulation | T = 0 | 25 °C | 40 °C | 25 °C | 40 °C |
| NAG6-Compound 2 | 102.54 | 97.34 | 97.83 | 97.45 | 98.19 |
| NAG6-Compound 2 (0.5%) | 100.84 | 101.75 | 99.48 | 97.15 | 97.24 |
| NAG10 | 98.59 | 98.68 | 98.07 | 95.87 | 96.05 |
| NAG14 | 108.12 | 110.20 | 109.95 | 107.06 | 107.60 |
| AG11-Compound 2 | 100.71 | 100.80 | 99.28 | 96.78 | 98.08 |
| CR8-Compound 2 | 98.38 | 98.58 | 111.07 | 94.92 | 99.67 |
| CR14-Compound 2 | 99.81 | 99.31 | 108.29 | 95.72 | 103.33 |

TABLE 25

Percentage peak purity (% area) of Compound 2 in developed Compound 2 active formulations at T = 0 and following 2 and 4 weeks storage at 25 °C and 40 °C

| | Percentage area (% area) of Compound 2 | | | | |
|---|---|---|---|---|---|
| | | T = 2 weeks | | T = 4 weeks | |
| Formulation | T = 0 | 25 °C | 40 °C | 25 °C | 40 °C |
| AG1-Compound 2 | 99.93 | 99.94 | 99.93 | 99.80 | 99.90 |
| AG11-Compound 2 | 99.93 | 99.95 | 99.96 | 99.66 | 99.94 |
| AG20 | 99.94 | 99.94 | 99.83** | 99.94 | 99.92 |
| AG23 | 99.94 | 99.94 | 99.93 | 99.94 | 99.92 |
| AG29 | 99.94 | 99.94 | 99.94 | 99.94 | 99.93 |
| NAG6-Compound 2 | 99.94 | 99.78 | 99.86** | 99.93 | 99.82**** |
| CR8-Compound 2 | 99.94 | 99.90** | 99.84** | 99.83*** | 99.94 |
| CR14-Compound 2 | 99.89 | 99.91 | 99.94 | 99.94 | 99.94 |

*Impurity peak (0.79% a/a) at TR 12.33 min detected in n = 1 replicate only.
**Impurity peak at TR ca. 12.10-12.21 min detected in one of the replicates only.
***Impurity peak (0.17% a/a) at TR 14.96 min detected in n = 1 replicate only.
***Impurity peak (0.36% a/a) at TR 12.20 min detected in n = 3 replicate only.

TABLE 26

Percentage peak purity (% a/a) of Compound 2 in developed Compound 2 active formulations at T = 0 and following 2 and 4 weeks storage at 25 ° and 40 °C

| | Percentage area (% area) of Compound 2 | | | | |
|---|---|---|---|---|---|
| | | T = 2 weeks | | T = 4 weeks | |
| Formulation | T = 0 | 25 °C | 40 °C | 25 °C | 40 °C |
| NAG6-Compound 2 | 99.21 | 99.95 | 99.94 | 99.84 | 99.69 |
| NAG6-Compound 2 (0.5%) | 99.91 | 99.88 | 99.80 | 99.86 | 99.85 |
| NAG10 | 99.84 | 99.58 | 99.75* | 99.83 | 99.79 |
| NAG14 | 99.84 | 99.85 | 99.78* | 99.84 | 99.84 |
| AG11-Compound 2 | 99.85 | 99.64 | 99.89 | 99.65 | 99.61 |
| CR8-Compound 2 | 99.91 | 99.58 | 99.94 | 99.82** | 99.87 |
| CR14-Compound 2 | 99.92 | 99.87 | 99.97 | 99.89 | 99.84 |

*Impurity peak at TR ca. 12.10-12.21 min detected in one of the replicates only.
**Impurity peak (0.16 % a/a) at TR 12.22 min detected in n = 2 replicate only.

The recovery of Compound 1 (Table 23) remained largely consistent throughout the 4 week stability testing. The recovery at T=0 ranged between 98% and 106%, with the higher recoveries being observed in the cream formulations (CR8—101.71% and CR14-105.32%). As described earlier, this is likely due to poor recovery efficiency from a more complex matrix system (emulsion).

Following the T=4 weeks timepoint, both the aqueous and non-aqueous gel formulation maintained recovery between 97%-99%, however, a slight downward trend in recovery was observed. Higher variability in recovery was observed for the cream formulations. CR8 remained consistent through the 2 week timepoint and the 25° C./4 week conditions (98-101%), however at the 40° C./4 week condition the recovery was 108.72%. Similar variability was observed for the CR14 formulation where at the 40° C./2 week condition the recovery was 109.40%, however by the 40° C./4 week condition the recovery was 105.82%.

The recovery of Compound 2 followed the same trend as the Compound 1, whereby the recovery remained largely consistent throughout the 4 weeks stability. At T=0 the recovery for all formulations ranged between 98% to 109%, with the higher recoveries being observed in NAG6 (102.54%) and NAG14 (108.12%).

While no major changes were observed a slight downward trend in recovery was observed for all formulations by the end of the 4 weeks stability testing, resulting in recoveries ranging between 96-107%. The purity of both Compound 1 (Table 68) and Compound 2 (Table 69) remained >99.6% are throughout the 4 week stability at all conditions for all formulations. There was no obvious drop in purity observed for any formulations at any of the conditions which was in line with that observed in similar formulations as discussed above.

The data generated during this study for Compound 1 highlighted that chemical stability was achieved at 25 and 40° C. for all the formulations. While variable recovery was observed for the cream formulations, the purity remained >99% and no degradation trends were observed. Similar conclusions can be made for the Compound 2 formulations where a slight downward trend and slight variability in recovery was observed, however the purity maintained consistent throughout indicating that drug chemical stability was achieved.

Example 15—Macroscopic Observations

The macroscopic observations (i.e. colour, clarity and visual viscosity) of the formulations are detailed in Table 27 and Table 28 and the results are summarized below.

TABLE 27

Macroscopic appearance of placebo and active Compound 1 formulations at T = 0 and following 2 and 4 weeks storage at 25 °C and 40 °C

| | Macroscopic appearance of Compound 1 formulations | | | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 45 °C | |
| Formulation | Placebo | Active | Placebo | Active | Placebo | Active | Placebo | Active | Placebo | Active |
| AG1-Compound 1 | Transparent, colourless, low viscosity | Transparent, colourless, low viscosity | No obvious change from T = 0 | | | | No obvious change from T = 0 | | | |
| AG11-Compound 1 | Turbid, colourless, low viscosity | Turbid, colourless, low viscosity | No obvious change from T = 0 | | | | No obvious change from T = 0 | | | |
| AG20 | Transparent, colourless, low viscosity | Transparent, colourless, low viscosity | No obvious change from T = 0 | | | | No obvious change from T = 0 | | | |
| AG23 | Transparent, colourless, low viscosity | Transparent, colourless, low viscosity | No obvious change from T = 0 | | | | No obvious change from T = 0 | | | |
| AG29 | Transparent, colourless, low viscosity | Transparent, colourless, low viscosity | No obvious change from T = 0 | | | | No obvious change from T = 0 | | | |
| NAG6-Compound 1 | Transparent, colourless, medium viscosity, stringy | Transparent, colourless, medium viscosity, stringy | No obvious change from T = 0 | | | | No obvious change from T = 0 | | | |
| CR8-Compound 1 | White, opaque, high viscosity, smooth application | White, opaque, high viscosity, smooth application | No obvious change from T = 0 | | Molen, potential phase separation | | No obvious change from T = 0 | | Phase separation | |
| CR14-Compound 1 | White, opaque, low viscosity, smooth application | White, opaque, low viscosity, application | No obvious change from T = 0 | | Molen, potential phase separation | | No obvious change from T = 0 | | | |

TABLE 28

Macroscopic appearance of placebo and active Compound 2 formulations at T = 0 and following 2 and 4 weeks storage at 25 °C and 40 °C

| | Macroscopic appearance of Compound 2 formulations | | | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 45 °C | |
| Formulation | Placebo | Active | Placebo | Active | Placebo | Active | Placebo | Active | Placebo | Active |
| NAG6-Compound 2 | Transparent, colourless, pourable, medium viscosity | Transparent, slight yellow tint, medium pourable, medium viscosity | No obvious change from T = 0 | | | | No obvious change from T = 0 | | | |
| NAG6 - Compound 2 (0.5%) | Transparent, colourless, medium viscosity, stringy | Transparent, faint yelow tint, medium viscosity, stringy | No obvious change from T = 0 | | | | No obvious change from T = 0 | | | |
| NAG10 | Transparent, colourless, low viscosity | Transparent, yellow tint, low viscosity | No obvious change from T = 0 | | | | No obvious change from T = 0 | | | |
| NAG14 | Transparent, colourless, low viscosity | Transparent, colourless, low viscosity | No obvious change from T = 0 | | | | No obvious change from T = 0 | | | |
| AG11 - Compound 2 | Turbid, colourless, low viscosity | Turbid, colourless, low viscosity | No obvious change from T = 0 | | | | No obvious change from T = 0 | | | |

TABLE 28-continued

Macroscopic appearance of placebo and active Compound 2 formulations at T = 0 and following 2 and 4 weeks storage at 25 °C and 40 °C

| | Macroscopic appearance of Compound 2 formulations | | | | | | | | | |
|---|---|---|---|---|---|---|---|---|---|---|
| | | | T = 2 weeks | | | | T = 4 weeks | | | |
| | T = 0 | | 25 °C | | 40 °C | | 25 °C | | 45 °C | |
| Formulation | Placebo | Active | Placebo | Active | Placebo | Active | Placebo | Active | Placebo | Active |
| CR8-Compound 2 | White, opaque, high viscosity, smooth application | White, opaque, high viscosity, smooth application | No obvious change from T = 0 | | Molten, potential phase separation | | No obvious change from T = 0 | | Phase Separation | |
| CR14-Compound 2 | White, opaque. Box viscosity, smooth application | White, opaque, low viscosity, smooth application | No obvious change from T = 0 | | Molten, potential phase separation | | No obvious change from T = 0 | | No obvious change from T = 0 | Viscosity change to medium otherwise as T = 0 |

Following the 4 weeks stability storage the aqueous gel formulations for both Compound 1 and Compound 2 did not change from the characteristics observed at T=0. Regardless of the gelling agent employed, all the aqueous gel formulations were observed to be of low viscosity. All aqueous gels were colourless and transparent aside from AG11 which was observed to be turbid. The active and placebo aqueous gel formulations were both observed to be the same throughout the stability study.

The non-aqueous gel formulations followed the same trend as the aqueous gels where no observable change was documented following the initial T=0 result. On key noticeable observation was the difference in colour between the active and placebo formulations for NAG6 and NAG10. The active versions were observed to have a slight yellow colour whereas the relevant placebo was colourless. The other characteristics matched in both the active and placebo formulation i.e. all non-aqueous gel formulations were observed to be transparent throughout the stability study. The cream formulations were observed to show the most significant changes throughout the stability study, The active and placebo formulations were observed to be the same throughout, as such any changes observed in the placebo formulation were also observed in the active counterpart. CR8 (for both Compound 1 and Compound 2) was observed to phase separate following storage at 40° C. for 4 weeks. CR14 containing Compound 1 was-observed to remain similar to the T=0 result, whereas CR14 containing Compound 2 was observed to increase in visual viscosity from low to medium. Phase separation at elevated temperatures is not uncommon for cream formulations as the higher temperature can cause the solid oil phase components to melt which then changes the physical characteristics of the formulation both pre and post cooling.

It should also be noted that the viscosity measurements were performed visually based on the pourability of the formulation, as such are subjective measurements of the viscosity. The results do however suggest that the formulations are physically stable.

Example 16—Microscopic Observations and Apparent pH

The microscopic observations of formulations containing both Compound 1 and Compound 2 in the formulations of Tables 64 et seq. are discussed below.

The aqueous gel formulations were observed to have no API crystals present at T=0 and this remained consistent throughout the 4 week stability study. AG11 was also observed to contain widespread small to medium sized droplets which was attributed to the presence of dimethicone in the formulation. The non-aqueous gel formulations largely remained consistent throughout the stability study, with no API crystals observed in any formulation at any timepoint or condition. However, NAG14 was observed to inconsistently contain few widespread droplets, NAG14 contains DIPA (at 19%) which is lipophilic and therefore can have the tendency to form droplets.

The cream formulations as with the other formulation types were not observed to contain any API crystals throughout the stability study. This was consistent through all timepoints and conditions for both-Compound 1 and Compound 2. CR14 was however observed to contain excipient crystals at the 40° C. conditions, which was most likely due to cetostearyl alcohol which has the tendency to crystallize upon cooling i.e. during removal from stability storage to ambient room temperature for analysis. In summary, no major changes were observed in any formulation containing either Compound 1 and Compound 2, indicating that physical stability of the formulations was achieved.

Apparent pH

The apparent pH was only assessed on the aqueous gel formulations containing Compound 1 and Compound 2. Following 4 weeks of storage at both 25° C. and 40° C. a slight downward trend in pH was observed for all formulations (active and placebo). At t=0 the pH varied between formulation, AG11 and AG20 both were subject to pH adjustment to ensure proper hydration of the Carbopol resulting in pH at approx. pH 6. Whereas AG 23 and AG29 both employed HPC as such their pH was not adjusted resulting in pH approx. pH 8.

The active and placebo formulations differed slightly in the pH, with the active formulations of Compound 1 displaying slightly lower pH values whereas the Compound 2 active gel formulation was slightly higher than its placebo counterpart. The pH of all the aqueous gel formulations was subject to only very slight changes in pH throughout the 4 week stability testing.

Example 17: Performance of Compounds 1 and 2 Test Formulations in sRICA

The anti-inflammatory activity of the IRAK4/TrkA inhibitors was determined in a skin resident immune cell assay (sRICA). In this model, human surgical skin waste was cultured in a transwell system, with the dermis in contact with cell culture media and the stratum corneum exposed to air. To perform the assay, each human skin sample was defatted and dermatomed to 750 μm. Next, 8 mm punch biopsies were obtained and placed in a membrane transwell. The biopsies were prepared with a barrier ring to contain the formulation and prevent leakage of the formulation. The transwells were inserted into culture wells with complete media, and a cocktail of cytokines and antibodies and/or inflammatory stimuli were added to promote skin resident immune cell polarization and/or elicitation of a specific inflammatory response. The transwells were treated with LPS as a positive control, a vehicle as a negative control, and various dual IRAK/TrkA inhibitors. TNFα protein expression was measured and the mean TNFα protein level in the LPS treated samples was set to 100%.

The Compounds were formulated at 80% saturated solubility. 10 ul of the test solvent system or prototype formulation was applied to topically prepared sRICA samples and allowed to penetrate the skin overnight. LPS was added the next day and media was harvest 48 hours after activation. N=6 per group. An unpaired, two-tailed students T-test was used to determined statistical significance.

The performance of the two IRAK4 inhibitors in Formulations representative of creams ("C" and "CR" formulations), aqueous gels ("AG" formulations), non-aqueous gels ("NAG" formulations), and ointments ("PO" Formulations) were evaluated in two rounds of the sRICA. Table 29 and Table 30 provide the composition of the formulations evaluated in the first round, and Table 31 and Table 32 provide the composition of the formulations evaluated in the second round.

TABLE 29

The formulation composition of Aqueous and Non-Aqueous Gels Compound 1 and 2 formulations at 80% of the saturation solubility determined in the corresponding solvent system evaluated in the first round of sRICA

| | Formulation Prototype | | | | | | | | | | |
|---|---|---|---|---|---|---|---|---|---|---|---|
| | AG1 | AG7 | AG8 | AG9 | AG10 | AG11 | NAG3 | NAG3 | NAG5 | NAG6 | NAG7 |
| | Solvent System | | | | | | | | | | |
| | SSA3 | SSA10 | SSA11 | SSA13 | SSA14 | SSA3 | SSNA4 | SSNA4 | SSNA4a | SSNA7 | SSNA3 |
| PEG 400 | 41.60 | 43.71 | 63.75 | 58.68 | 34.46 | 40.85 | 63.73 | 60.25 | 60.35 | 60.51 | 64.19 |
| Transcutol P | 45.00 | 45.00 | 25.00 | 25.00 | 25.00 | 45.00 | 25.00 | 25.00 | 25.00 | 25.00 | — |
| Water | 10.00 | 10.00 | 10.00 | 5.00 | 5.00 | 10.00 | — | — | — | — | — |
| Dipropylene glycol | — | — | — | 10.00 | — | — | — | — | — | — | — |
| PEG 300 | — | — | — | — | 34.46 | — | — | — | — | — | — |
| Glycerol | — | — | — | — | — | — | 10.00 | 10.00 | 10.00 | — | 10.00 |
| Propylene glycol | — | — | — | — | — | — | — | — | — | — | 20.00 |
| Diisopropyl adipate | — | — | — | — | — | — | — | — | — | 10.00 | — |
| Dimethicone 350 | — | — | — | — | — | 0.75 | — | — | — | — | — |
| Benzyl alcohol | 2.00 | — | — | — | — | 2.00 | — | — | — | — | 2.00 |
| BHT | 0.10 | — | — | 0.10 | 0.10 | 0.10 | 0.10 | 0.10 | — | 0.10 | 0.10 |
| Carbopol 980NF | 1.0 | 1.00 | 1.00 | 1.00 | 0.75 | 1.00 | — | — | — | — | — |
| HPC-HF | — | — | — | — | — | — | 1.00 | 1.00 | 1.00 | 1.00 | 1.00 |
| Compound 1 | 0.30 | 0.29 | 0.25 | 0.22 | 0.24 | 0.30 | 0.17 | — | — | — | — |
| Compound 2 | — | — | — | — | — | — | — | 3.65 | 3.65 | 3.39 | 2.71 |
| Total (% w/w) | 100 | 100 | 100 | 100 | 100 | 100 | 100 | 100 | 100 | 100 | 100 |

TABLE 30

The formulation composition of Cream and Ointment formulations at 80% of the saturation solubility determined in the corresponding solvent system evaluated in the first round of sRICA.

| Formulation Prototype | PO5 | CR5 | PO5 | CR5 |
|---|---|---|---|---|
| Solvent System | SSPO1 | SSC8 | SSPO1 | SSC8 |
| PEG 400 | 58.72 | 43.80 | 55.84 | 43.83 |
| Transcutol P | 15.00 | 15.00 | 15.00 | 15.00 |
| Water | — | 20.00 | — | 20.00 |
| BHT | 0.10 | 0.10 | 0.10 | 0.10 |
| PEG 3550 | 25.00 | — | 24.00 | — |
| IPM | 1.00 | — | 1.00 | — |
| Cetostearyl alcohol | — | 5.00 | — | 5.00 |
| Crodamol GTCC | — | 10.00 | — | 10.00 |
| Dimethicone 350 | — | 1.00 | — | 1.00 |
| Brij 52 (Brij 72)I | — | 1.89 | 1 | 1.89 |
| Brij S20 | — | 3.11 | — | 3.11 |
| Compound 1 | 0.18 | 0.10 | — | — |
| Compound 2 | — | — | 4.06 | 0.07 |
| Total (% w/w) | 100 | 100 | 100 | 100 |

TABLE 31

The formulation composition of Aqueous and Non-Aqueous Gels at 80% of the saturation solubility determined in the corresponding solvent system evaluated in the second round of sRICA

| | Formulation Prototype | | | | | | | | | | |
|---|---|---|---|---|---|---|---|---|---|---|---|
| | AG1 | AG11 | AG20 | AG23 | AG29 | NAG6 | NAG6 | NAG6-0.5% | NAG10 | NAG14 | AG11 |
| | Solvent System | | | | | | | | | | |
| | SSA3 | SSA3 | SSA18 | SSA18 | SSA19 | SSNA7 | SSNA7 | SSNA7 | SSNA7 | SSNA1 | SSA3 |
| PEG 400 | 41.60 | 40.85 | 36.62 | 33.62 | 53.65 | 63.75 | 60.51 | 63.40 | 57.51 | 13.42 | 40.76 |
| Transcutol P | 45.00 | 45.00 | 45.00 | 45.00 | 25.00 | 25.00 | 25.00 | 25.00 | 25.00 | 25.00 | 45.00 |
| Water | 10.00 | 10.00 | 10.00 | 10.00 | 10.00 | — | — | — | — | — | 10.00 |
| Dipropylene glycol | — | — | — | — | — | — | — | — | — | — | — |
| PEG 300 | — | — | — | — | — | — | — | — | — | — | — |
| Glycerol | — | — | — | — | — | — | — | — | — | 19.00 | — |
| Propylene glycol | — | — | — | — | — | — | — | — | — | 19.00 | — |
| Diisopropyl adipate | — | — | 5.00 | 5.00 | 5.00 | 10.00 | 10.00 | 10.00 | 10.00 | 19.00 | — |
| Dimethicone 350 | — | 0.75 | — | — | — | — | — | — | — | — | 0.75 |
| Benzyl alcohol | 2.00 | 2.00 | 2.00 | 2.00 | 2.00 | — | — | — | — | — | 2.00 |
| BHT | 0.10 | 0.10 | 0.10 | 0.10 | 0.10 | 0.10 | 0.10 | 0.10 | 0.10 | 0.10 | 0.10 |
| Carbopol 980NF | 1.00 | 1.00 | 1.00 | — | — | — | — | — | — | — | 1.00 |
| HPC-JF | — | — | — | 4.00 | 4.00 | — | — | — | 4.00 | 4.00 | — |
| HPC-HF | — | — | — | — | — | 1.00 | 1.00 | 1.00 | — | — | — |
| Compound 1 | 0.30 | 0.30 | 0.28 | 0.28 | 0.25 | 0.15 | — | — | — | — | — |
| Compound 2 | — | — | — | — | — | — | 3.39 | 0.50 | 3.39 | 0.48 | 0.39 |
| Total (% w/w) | 100 | 100 | 100 | 100 | 100 | 100 | 100 | 100 | 100 | 100 | 100 |

TABLE 32

The formulation composition of Cream and Ointments at 80% of the saturation solubility determined in the corresponding solvent system evaluated in the second round of sRICA

| Formulation Prototype | CR8 | CR14 | CR8 | CR14 |
|---|---|---|---|---|
| Solvent System | SSC8 | SSC8 | SSC8 | SSC8 |
| PEG 400 | 45.61 | 41.80 | 45.64 | 41.83 |
| Transcutol P | 15.94 | 15.00 | 15.94 | 15.00 |
| Water | 21.25 | 20.00 | 21.25 | 20.00 |
| Benzyl alcohol | 2.00 | 2.00 | 2.00 | 2.00 |
| BHT | 0.10 | 0.10 | 0.10 | 0.10 |
| Cetostearyl alcohol | 2.50 | 2.00 | 2.50 | 2.00 |
| Crodamol GTCC | 6.50 | — | 6.50 | — |
| Dimethicone 350 | 1.00 | 1.00 | 1.00 | 1.00 |
| Cyclomethicone 5NF | — | 13.00 | — | 13.00 |
| Brij 52 (Brij 72)I | 2.28 | 3.38 | 2.28 | 3.38 |
| Brij S20 | 2.72 | 1.62 | 2.72 | 1.62 |
| Compound 1 | 0.10 | 0.10 | — | — |
| Compound 2 | — | — | 0.07 | 0.07 |
| Total (% w/w) | 100 | 100 | 100 | 100 |

Figure 2:
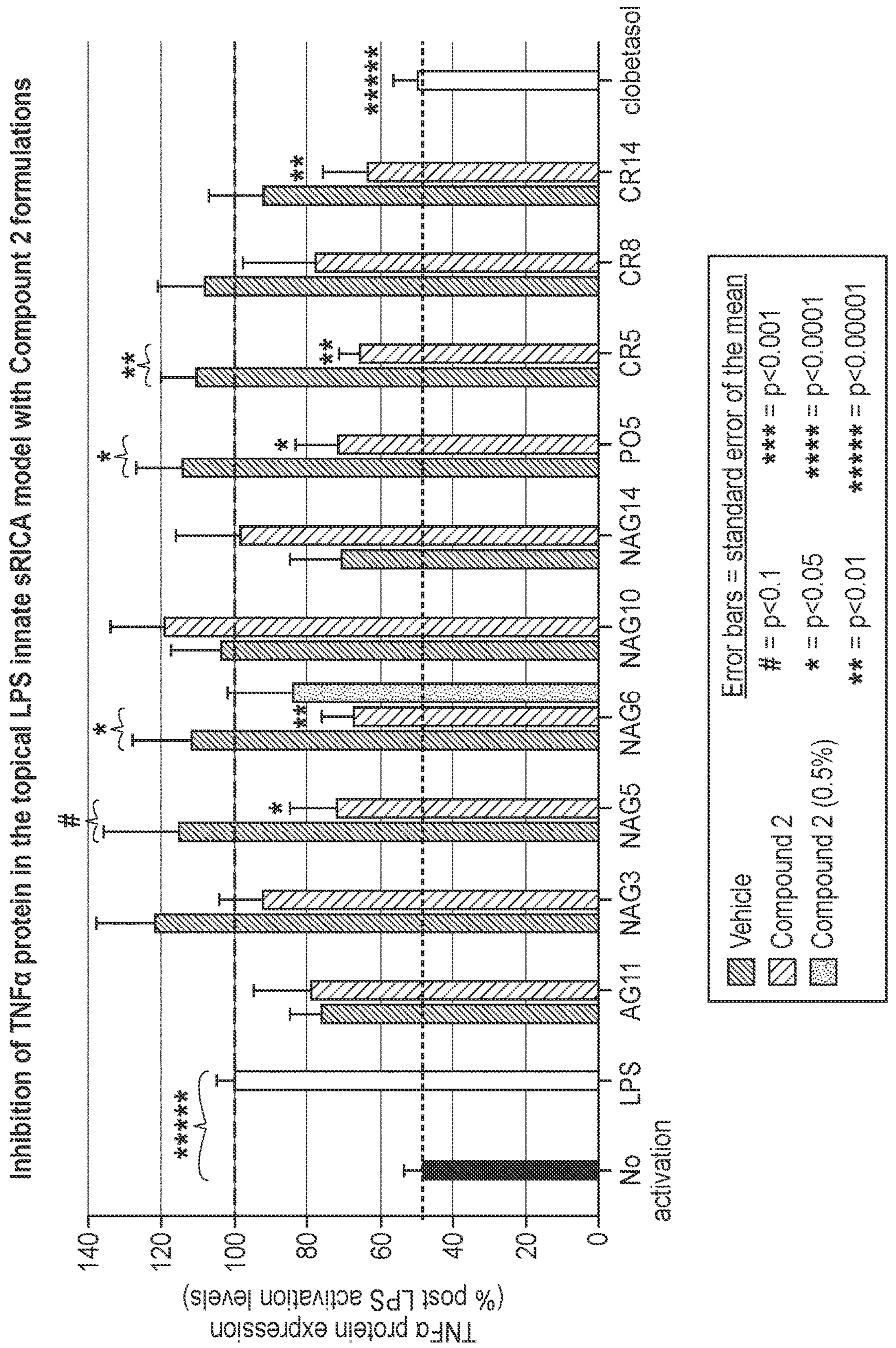
FIG. 2 illustrates the performance of a IRAK4 inhibitor (Compound 2) according to the present disclosure in various vehicle formulations in sRICA. The prepared vehicles are summarized in Tables 29-32.

The combined results for these studies are shown in FIG. 1 (for Compound 1) and FIG. 2 (for Compound 2).

For Compound 1 (FIG. 1):

All Compound 1 formulations were prepared at 80% saturation (active formulation=blue bars, vehicle formulations=yellow bars). The combined results of 6 independent studies (6 different skin donors) are shown. Each study was normalized to the % max of TNFα production (i.e. the average TNFα concentration of LPS activated skin alone was set to 100%, all other values (untreated no activation and treated samples) were obtained as a percentage of this. N=9-18 per group. Formulated Clobetasol (Dermovate) was utilized for these studies, serving as a positive control for suppression of inflammation (dark blue bar on far right). An unpaired student, 2-tailed, students-T-test was used to determine statistical significance from LPS activation alone. Error bars=standard error of the mean. #p<0.1, *p<0.05, p<0.01, *p<0.001, **p<0.0001, ***p<0.00001.

For Compound 2 (FIG. 2):

All Compound 2 formulations prepared as at 80% saturation (active formulation at 80% saturation=blue bars), with the exception of Compound 1/NAG6 0.5 which was prepared at a 0.5% formulation (grey bar). The 80% saturated Compound 1/NAG6 is a 3.4% formulation. Vehicle alone treated inflamed skin=yellow bars. The combined results of 6 independent studies (6 different skin donors) are shown. Each study was normalized to the % max of TNFα production (i.e. the average TNFα concentration of LPS activated skin alone was set to 100%, all other values (untreated no activation and treated samples) were obtained as a percentage of this. N=9-18 per group. Formulated Clobetasol (Dermovate) was utilized for these studies, serving as a positive control for suppression of inflammation (dark blue bar on far right). An unpaired student, 2-tailed, students-T-test was used to determine statistical significance from LPS activation alone. Error bars=standard error of the mean. #p<0.1, *p<0.05, p<0.01, *p<0.001, **p<0.0001, ***p<0.00001.

Results from Round 1:

There was a statistically significant ($p<0.0001$) induction of TNFα protein upon LPS activation of the skin in this model, demonstrating successful induction of inflammation in this study. Additionally, topical Clobetasol (*Dermovate), significantly reduced inflammation back to baseline levels, indicating that a powerful topical anti-inflammatory can prevent inflammation in this model. Many of the IRAK4/TrkA topical prototypes significantly inhibited TNFα production, both versus LPS stimulation alone and versus their respective vehicle.

AG1, AG7 and AG11 all contain 45% Transcutol P, whereas AG8, AG9, and AG10 only contain 25% Transcutol P. Only the formulations with 45% Transcutol P (AG1, AG7, and AG11) resulted in significant reduction in inflammation versus LPS stimulation alone. This is in accord with the Examples above, which similarly indicate an increase in efficacy with increasing levels of Transcutol P. However, the vehicles on their own for AG1, AG7, and AG11 also had a slight anti-inflammatory activity, resulting in a lack statistical significance for the active versus placebo AG1, AG7, and AG11 formulations in this study.

Significance from both LPS and LPS stimulated vehicle was found for several of the formulations, including non-aqueous gel, ointment, and cream. Of note, the creams (Compounds 1 and 2 in CR5) obtained strong statistical significance from both LPS and vehicle. This was an unexpected finding, as both compounds are poorly soluble in water and thus the CR5 formulation only contains 0.1% of API. While not wishing to be bound by a particular theory, it is believed that the thermodynamic properties of Compound 1 or Compound 2 in this type of formulation 'encourages' penetration of the compound into the skin and thus results in the superior efficacy, even though the formulation contains a low total percentage (w/w) of API.

In sum, the results show that many prototype formulations of Compound 1 or Compound 2 could penetrate human skin in sufficient quantities to significantly repress LPS mediate inflammation. In parallel, we also assessed the aesthetic quality of the prototype formulations, with rosacea patient interviews and round. In general, all formulations were acceptable to a rosacea patient, but there was a preference towards the gels (specifically AG11 and NAG6). The cream formulation (specifically CR5) was also favored, but it was suggested by the rosacea patients that perhaps it could be more 'lotion-like'. From an aesthetic perspective, patients felt the ointment formulation was the least attractive formulation for a topical program. The aesthetic feedback, in combination with the topical LPS sRICA results provided the rationale for creating additional prototype formulations (Round 2).

Round 2 of the sRICA Study

Regarding aqueous gels for Compound 1, additional prototypes with 25% Transcutol P were explored. In Round 1, only prototypes with 45% Transcutol P demonstrated significant reduction in inflammation. However, 45% is the maximal Transcutol P allowed in formulations, and thus additional prototypes with only 25% Transcutol P were explored. Furthermore, vehicles containing 45% Transcutol P also presented with mild-anti-inflammatory vehicle effects, which prevented a statistically significant reduction of active versus vehicle treated skin.

Regarding Compound 2 in the non-aqueous gels, additional prototypes were explored to see if the efficacy from NAG6 could be improved upon. A 0.5% T-394 NAG6 formulation was also evaluated to determine if efficacy is lost compared to the original 3.4% T-394 NAG6 formulation (this is 80% saturation for this API in this vehicle).

Lastly, due to the impressive performance of both Compound 1 and Compound 2 with the original cream (CR5), additional cream prototypes were created with both compounds. These new formulations were made more 'lotion-like' and in line with the request from the rosacea patients.

Except for the 0.5% Compound 1/NAG6 formulations, all Round 2 formulations were manufactured at 80% saturation. Compound 1/AG1, Compound 1/AG11, Compound 1/NAG6 were included again in this study to serve as benchmarks from Round 1 formulations. The topical LPS sRICA was prepared as previously described. 10 ul of the prototype formulation was applied topically, 12-24 hours prior to LPS stimulation. Conditioned cell media was collected and assessed for expression of inflammatory proteins after 48 hours of exposure to LPS stimulation.

In the sRICA studies performed with Round 2 prototype formulations, there was highly significant induction of TNFα, demonstrating the successful elicitation of inflammation in these studies. Similar to previous studies, topical Clobetasol completely inhibited TNFα induction in this model.

Results for Compound 1 Round 2 Formulations:

In alignment with the results from Round 1, Compound 1 in AG1 and AG11, resulted in about a 50-75% inhibition of inflammation (Compound 1/AG1 performed a bit better than in the Round 1 studies, Compound 1/AG 11 performed a bit worse than in the Round 1 studies). None of the new aqueous gel prototypes (AG20, AG23, and AG29), nor the nonaqueous gel (NAG6 prototype), demonstrated improved efficacy compared to round 1 Compound 1 aqueous gel prototypes with 45% Transcutol P.

One unexpected and significant finding from the Round 2 formulation study was the impressive efficacy of Compound 1 in the 'lotion-like' cream formulations (CR8 and CR14), demonstrating significant inhibition of inflammation versus both LPS and placebo. Both formulations reduced inflammation down to baseline levels, on par with the potent topical steroid Clobetasol.

Regarding results for Compound 2, none of the gel formulations AG11, NAG10, or NAG14 performed better than the NAG6 from Round 1. Furthermore, reducing the concentration of Compound 2 from 3.4% to a 0.5% solution prevented significant suppression of inflammation in this model, suggesting a topical dose-response.

The results for Compound 1 and Compound 2 in the second sRICA round are shown in FIGS. 1 and 2, respectively. Black bar and line indicates level of TNFα at baseline (no inflammation), red bar and line indicates maximal inflammation induced by LPS, blue bars indicate formulations with API, and yellow bars indicate vehicles alone. Topical Clobetasol (Dermovate) is used as a positive drug control for the assay and is the dark blue bar on the far right of the graphs.

Regarding Compound 1 formulations (FIG. 1), although the aqueous gels with 45% Transcutol P significantly inhibited induction of TNFα in the LPS sRICA versus untreated skin, they did not statistically significantly separate from their respective vehicles. Reduction of Transcutol P levels to 25% did alleviate the vehicle alone effects, but efficacy with the API was lost (see AG8, AG9, and AG10). Compound 1 in NAG3 did demonstrate significant anti-inflammatory activity versus untreated and vehicle treated inflamed skin, but NAG3 was highly disliked from an aesthetic perspective (described as 'snotty and stringy'). NAG6 (the most preferred non-aqueous gel formulation), did not deliver enough Compound 1 to significantly reduce inflammation in this model.

Overall, the ointment and cream formulations of Compound 1 performed very well. All cream and ointment prototype formulation (for both Compound 1 and Compound 2) demonstrated statistical significance from untreated inflamed skin and vehicle treated inflamed skin. Of note, Compound 1 in CR14 completely abolished TNFα induction by LPS in this model, performing on par with Clobetasol. These results highlighted that creams (and CR14 in particular), as effective vehicles for delivering Compound 1.

Regarding the Compound 2 formulations (FIG. 2), several of the formulations also prevented TNFα induction by LPS. Compound 2 at a 3.4% concentration in NAG6 achieved statistical separation from both untreated and vehicle treated LPS stimulated skin. Dropping the concentration of Compound 2 to 0.5% in NAG6 resulted in loss of statistical significance (see grey bar), serving as a beginning investigation of the dose-response.

Other notable prototypes included the ointment (PO5), and two of the creams (CR5 and CR14), in regard to statistically significant inhibition of TNFα versus untreated and vehicle treated inflamed skin. However, unlike the results with Compound 1, none of the formulations with Compound 2 could completely suppress inflammation back down to baseline, nor performed on-par with topical Clobetasol.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A topical composition comprising:

a pharmaceutically effective amount of a compound selected from the group consisting of:

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, 2-(2-((2,2-difluoroethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide, N-(3-((3S,4S)-4-hydroxy-3-methyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide, N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide, 2-(2-((cyclopropylmethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide, N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3-isopropyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(3-(2-hydroxypropyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, N-(3-(4-((cyclopropylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide, and N-(3-(3,3-dimethyl-2-oxopyrrolidin-1-yl)-1-(oxetan-3-yl)-1H-pyrazol-4-yl)-2-(2-((2,2,2-trifluoroethyl)amino)pyridin-4-yl)-1,3-oxazole-4-carboxamide, or a stereoisomer, a tautomer, or a pharmaceutically acceptable salt thereof, a solvent system comprising PEG 400 and diethylene glycol monoethyl ether; and an antioxidant comprising butylated hydroxytoluene (BHT), wherein the solvent system comprises diethylene glycol monoethyl ether in an amount of from 15% to 25% by weight of the composition, wherein the solvent system comprises PEG 400 in an amount of from about 35% to about 70% by weight of the composition.

2. The topical composition of claim 1, wherein the solvent system further comprises one or more solvents selected from a polyether, a polyethylene glycol, a polyether alcohol, an ether, and an alcohol.

3. The topical composition of claim 1, wherein the solvent system comprises PEG 400 in an amount of about 35% to about 50% by weight of the composition, or about 40% to about 45% by weight of the composition, or about 55% to about 65% by weight of the composition; or about 40%, about 45%, about 50%, about 55%, or about 60% by weight of the composition.

4. The topical composition of claim 1, wherein the solvent system comprises diethylene glycol monoethyl ether in an amount of about 15%, about 20%, or about 25% by weight of the composition.

5. The topical composition of claim 1, wherein the solvent system further comprises one or more preservatives selected from alcohols having from 2-10 carbon atoms.

6. The topical composition of claim 1, wherein the solvent system further comprises one or more preservatives in an amount of from about 0.01% to about 20% by weight of the composition, or about 0.1% to about 10% by weight of the composition; or about 0.5% to about 5% by weight of the composition, or about 1% to about 3% by weight of the composition, or about 2% by weight of the composition.

7. The topical composition of claim 1, wherein the solvent system is present in an amount of from about 50% to about 90% by weight of the composition, or about 75% to about 90% by weight of the composition; or about 80% to about 90% by weight of the composition, or about 85% to about 90% by weight of the composition, or about 55% to about 65% by weight of the composition; or about 55% to about 60% by weight of the composition.

8. The topical composition of claim 1, wherein the antioxidant is present in an amount of about 0.001 wt. % to about 1 wt. % based on the total weight of the composition.

9. The topical composition of claim 1, wherein the composition further comprises a nonsolvent.

10. The topical composition of claim 9, wherein the nonsolvent is water, a silicone oil, or a mixture thereof.

11. The topical composition of claim 10, wherein the water is present in an amount of from about 5% to about 30% by weight of the composition, or about 5% to about 15% by weight of the composition; or about 15% to about 25% by weight of the composition, or about 10%, or about 15%, or about 20% by weight of the composition; and the silicone oil is dimethicone 350, and is present in an amount of from about 0.01% to about 2% by weight of the composition, or about 0.1% to about 1.5% by weight of the composition; or about 0.5% to about 1% by weight of the composition, or about 0.75% by weight of the composition.

12. The topical composition of claim 1, wherein the composition further comprises a polymer gelling agent selected from one or both of a crosslinked polyacrylic acid and a non-ionic cellulose ether, wherein the gelling agent is present in an amount of from 0.01% to about 5% by weight of the composition, or about 0.1% to about 3% by weight of the composition; or about 0.5% to about 2% by weight of the composition, or about 0.75% to about 1.25% by weight of the composition or about 1% by weight of the composition.

13. The topical composition of claim 1, further comprising a skin conditioner selected from diisopropyl adipate and a silicone oil, wherein the skin conditioner is present in an amount of from 0.1% to about 15% by weight of the composition, or about 0.1% to about 5% by weight of the composition; or about 0.1% to about 2% by weight of the composition, or about 5% to about 15% by weight of the composition, or about 1% by weight of the composition, or about 10% by weight of the composition.

14. The topical composition of claim 1, further comprising an emollient; wherein the emollient is a triglyceride, wherein the emollient is present in an amount of from 0.1% to about 15% by weight of the composition, or about 0.1% to about 5% by weight of the composition; or about 0.1% to about 2% by weight of the composition, or about 5% to about 15% by weight of the composition, or about 1% by weight of the composition, or about 10% by weight of the composition.

15. The topical composition of claim 1, further comprising a viscosity enhancing agent, selected from one or more $C_{14}$-$C_{30}$ fatty alcohols, a cellulose, an acrylate polymer or crosspolymer, a carbomer, or a poloxamer; wherein the viscosity enhancing agent is present in an amount of from 0.1% to about 15% by weight of the composition, or about 1% to about 10% by weight of the composition; or about 3% to about 7% by weight of the composition, or about 5% by weight of the composition.

16. The topical composition of claim 1, further comprising a surfactant; wherein the surfactant is selected from one or more of polyoxyethylene fatty ethers; nonoxynols, polysorbates, polyoxylene alcohols, polyoxylene fatty acid esters, sodium lauryl sulfate, and sorbitan monostearate; wherein the surfactant is present in an amount of from 0.1% to about 15% by weight of the composition, or about 1% to about 5% by weight of the composition; or about 1%, about 2%, about 3%, about 4%, about 5%, about 7%, or about 10% by weight of the composition.

17. The topical composition of claim 1, further comprising an additional excipient; wherein the additional excipient is selected from $C_{1-20}$ alkanols, oleyl alcohol, benzyl alcohol, a saturated or unsaturated fatty acid ester, a polyoxythylene fatty ether, a polyoxylene fatty acid ester, diethylene glycol monoethyl ether, 1,3-dimethyl-2-imidazolidinone, dimethyl isosorbide, stearic acid, magnesium stearate, and propylene glycol; wherein the additional excipient is present in an amount of from 0.1% to about 20% by weight of the composition, or about 1% to about 15% by weight of the composition; or about 5% to about 15% by weight of the composition, or about 10% by weight of the composition.

18. The topical composition of claim 1, wherein the composition is in the form of a cream, a lotion, a foam, an aqueous gel, a non-aqueous gel, a spray or an ointment.

19. The topical composition of claim 1, wherein the composition has an apparent pH of about 3.5 to about 7.5, about 4 to about 7, about 4.5 to about 6.5 or about 5 to about 6.5, or about 5.5 to about 6.5, or about 6.

20. The topical composition of claim 1, wherein the topical composition is for application to a skin, wherein the skin is mammalian skin or human skin.

21. The topical composition of claim 1, wherein the topical composition is an aqueous gel; and the solvent system comprises PEG 400 and diethylene glycol monoethyl ether, wherein the w/w ratio of PEG 400/diethylene glycol monoethyl ether is about 0.7 to about 1.1, about 0.8 to about 1.0, or about 0.9.

22. The topical composition of claim 1, wherein the topical composition is a non-aqueous gel; and the solvent system comprises PEG 400 and diethylene glycol monoethyl ether, wherein the w/w ratio of PEG 400/diethylene glycol monoethyl ether is about 2.2 to about 2.6, about 2.3 to about 2.5, or about 2.4.

23. The topical composition of claim 1, wherein the topical composition is a cream; the solvent system comprises PEG 400 and diethylene glycol monoethyl ether, wherein the w/w ratio of PEG 400/diethylene glycol monoethyl ether is about 2.6 to about 3.2, about 2.7 to about 3.1, or about 2.9.

24. The topical composition of claim 1, wherein the topical composition is an ointment; and the solvent system comprises PEG 400 and diethylene glycol monoethyl ether, wherein the w/w ratio of PEG 400/diethylene glycol monoethyl ether is about 3.5 to about 4.5, about 3.8 to about 4.2, or about 4.

25. A method for treating an inflammatory dermatological disorder, the method comprising topically administering to a subject in need thereof a topical composition according to claim 1 wherein the inflammatory dermatological disorder is rosacea, psoriasis, atopic dermatitis, hidradenitis suppurativa, seborrheic dermatitis, contact dermatitis, urticaria, dermatitis herpetiformis, nummular dermatitis, lichen planus, *Pityriasis rosea*, cutaneous lupus, acne, cancers of the skin, or miliaria.

* * * * *